United States Patent
Naganawa et al.

(10) Patent No.: US 10,835,520 B2
(45) Date of Patent: Nov. 17, 2020

(54) PHENYL DERIVATIVE

(71) Applicant: ONO PHARMACEUTICAL CO., LTD., Osaka (JP)

(72) Inventors: Atsushi Naganawa, Osaka (JP); Kensuke Kusumi, Osaka (JP); Kazuhiro Otsuki, Osaka (JP); Tetsuya Sekiguchi, Osaka (JP); Akito Kakuuchi, Osaka (JP); Koji Shinozaki, Osaka (JP); Hiroshi Yamamoto, Osaka (JP); Shigeyuki Nonaka, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/148,647

(22) Filed: Oct. 1, 2018

(65) Prior Publication Data
US 2019/0030010 A1  Jan. 31, 2019

Related U.S. Application Data

(60) Division of application No. 15/784,376, filed on Oct. 16, 2017, now Pat. No. 10,117,861, which is a division of application No. 15/089,690, filed on Apr. 4, 2016, now Pat. No. 9,820,980, which is a division of application No. 14/592,100, filed on Jan. 8, 2015, now Pat. No. 9,340,499, which is a continuation of application No. 14/347,178, filed as application No. PCT/JP2012/074968 on Sep. 27, 2012, now Pat. No. 8,975,409.

(30) Foreign Application Priority Data

Sep. 29, 2011  (JP) .................. 2011-213987

(51) Int. Cl.
| | |
|---|---|
| A61K 31/445 | (2006.01) |
| C07D 405/12 | (2006.01) |
| C07D 207/16 | (2006.01) |
| C07D 211/52 | (2006.01) |
| C07D 205/04 | (2006.01) |
| C07D 211/48 | (2006.01) |
| C07D 207/12 | (2006.01) |
| C07D 401/12 | (2006.01) |
| A61K 31/397 | (2006.01) |
| A61K 31/40 | (2006.01) |
| A61K 31/4523 | (2006.01) |
| A61K 31/453 | (2006.01) |
| A61K 31/454 | (2006.01) |
| A61K 31/4545 | (2006.01) |

(52) U.S. Cl.
CPC .......... *A61K 31/445* (2013.01); *A61K 31/397* (2013.01); *A61K 31/40* (2013.01); *A61K 31/453* (2013.01); *A61K 31/454* (2013.01); *A61K 31/4523* (2013.01); *A61K 31/4545* (2013.01); *C07D 205/04* (2013.01); *C07D 207/12* (2013.01); *C07D 207/16* (2013.01); *C07D 211/48* (2013.01); *C07D 211/52* (2013.01); *C07D 401/12* (2013.01); *C07D 405/12* (2013.01)

(58) Field of Classification Search
CPC .................................................... A61K 31/445
USPC ......................................................... 546/221
See application file for complete search history.

(56) References Cited

U.S. PATENT DOCUMENTS

| | | | |
|---|---|---|---|
| 8,975,409 B2 * | 3/2015 | Naganawa | C07D 405/12 546/221 |
| 9,340,499 B2 * | 5/2016 | Naganawa | C07D 405/12 |
| 9,676,719 B2 | 6/2017 | Kusumi et al. | |

(Continued)

FOREIGN PATENT DOCUMENTS

| | | |
|---|---|---|
| CN | 1590378 A | 3/2005 |
| EP | 0643076 A1 | 3/1995 |

(Continued)

OTHER PUBLICATIONS

Dorwald F. A. Side Reactions in Organic Synthesis, 2005, Wiley: VCH, Weinheim p. IX of Preface pp. 1-15.*

(Continued)

*Primary Examiner* — Nizal S Chandrakumar
(74) *Attorney, Agent, or Firm* — Sughrue Mion, PLLC

(57) ABSTRACT

The compound of the formula (I-1):

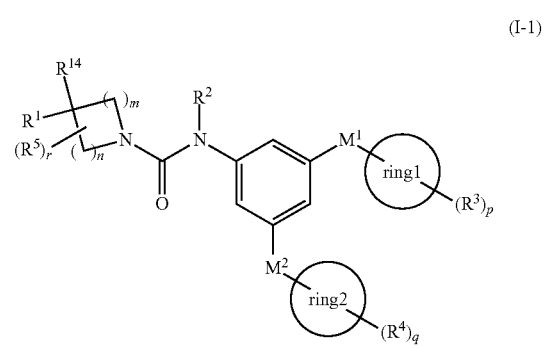

wherein all the symbols have the same meanings as described in the specification, has two cyclic groups, particularly phenoxy groups at specific substitution positions and thus has high human S1P$_2$ antagonistic activity. The compound may therefore be used as a therapeutic agent for S1P$_2$-mediated diseases such as diseases resulting from vascular constriction, fibrosis, and respiratory diseases.

9 Claims, 6 Drawing Sheets

(56) References Cited

U.S. PATENT DOCUMENTS

| | | |
|---|---|---|
| 9,820,980 B2 | 11/2017 | Naganawa et al. |
| 2006/0148844 A1 | 7/2006 | Nakade et al. |
| 2007/0135402 A1 | 6/2007 | Habashita et al. |
| 2010/0121052 A1 | 5/2010 | Jain et al. |
| 2010/0216767 A1 | 8/2010 | Aikawa et al. |
| 2011/0269244 A1 | 11/2011 | Petter et al. |
| 2012/0136002 A1 | 5/2012 | Goswami et al. |

FOREIGN PATENT DOCUMENTS

| | | |
|---|---|---|
| JP | 6-234797 A | 8/1994 |
| JP | 2009-534440 A | 9/2009 |
| JP | 2010-514693 A | 5/2010 |
| JP | 2011-524881 A | 9/2011 |
| RU | 2390519 C2 | 5/2010 |
| WO | 01/98301 A1 | 12/2001 |
| WO | 2004/002531 A1 | 1/2004 |
| WO | 2005/020882 A2 | 3/2005 |
| WO | 2005/063704 A1 | 7/2005 |
| WO | 2007/125049 A1 | 11/2007 |
| WO | 2010/133748 A1 | 11/2010 |
| WO | 2011/082285 A1 | 7/2011 |

OTHER PUBLICATIONS

Adada, et al., "Sphingosine-1-phosphate receptor 2", The FEBS Journal, Issue No. 280, 2013, pp. 6354-6366.

Proia, et al. "Emerging biology of sphingosine-1-phosphate: its role in pathogenesis and therapy", The Journal of Clinical Investigation, vol. 125, Issue No. 4, Apr. 2015, pp. 1379-1387.

United States Patent and Trademark Office, Communication dated Aug. 16, 2016 issued in co-pending U.S. Appl. No. 14/780,152.

European Patent Office, Communication dated Oct. 21, 2016, in counterpart European Patent Application No. 14775353.7.

Russian Intellectual Property Office, Decision to Grant dated Jan. 24, 2017 issued in counterpart Russian Application No. 2014117170/04(027155).

State Intellectual Property Office of the People's Republic of China, Communication dated Mar. 30, 2017, issued in counterpart Chinese Application No. 201480017929.3.

Freshney (Culture of Animal Cells, a Manual of Basic Technique, Alan R. Liss, Inc., 1983, New York, p. 4.

Roviezzo et al, Journal of Pharmacology and Experimental Therapeutics 337:830-837, 2011.

Kusumi et al. Bioorganic & Medicinal Chemistry Letters 26 (2016) 1209-1213 and Bioorg. Med. Chem. Lett. 25 (2015) 4387-4392.

Bolli et al., "Synthetic Sphingosine 1-Phosphate Receptor Modulators—Opportunities and Potential Pitfalls", Current Topics in Medicinal Chemistry, Mar. 1, 2011, 9 pages total, vol. 11 No. 6, Allschwil, Switzerland XP055110362.

Bromidge et al.; "Biarylcarbamoylindolines are Novel and Selective 5-HT2c Receptor Inverse Agonists: Identification of 5-Methyl-1-[[2-[(2-methyl-3-pyridypoxy]-5-pyridylkarbamoyl]-6-trifluoromethylindoline (SB-243213) as a Potential Antidepressant/Anxiolytic Agent"; Journal of Medicinal Chemistry, 2000, vol. 43, No. 6; pp. 1123-1134; 2000 American Chemical Society; Published on Web Feb. 25, 2000.

National Office of Intellectual Property of Vietnam, Communication dated of Jan. 27, 2016, issued in counterpart Vietnamese Patent Application No. 1-2014-01021.

European Patent Office, Extended European Search Report dated Apr. 20, 2015, issued in counterpart European Application No. 12837524.3.

Intellectual Property Office of Singapore, Communication dated Feb. 1, 2016 issued in counterpart Singapore Patent Application No. 11201400954R.

International Searching Authority, International Search Report dated Oct. 23, 2012, issued in counterpart International Application No. PCT/JP2012/074968.

Venkatesh et al., J. Pharm. Sci. 89, 145-54 (2000).

Wolff, Burger's medicinal Chemistry and Drug Discovery, vol. 1, Principles and Practice, John Wiley & sons, New York, 1997.

West, Solid-State Chemistry and Its Applications, 1984, John Wiley & Sons.

Ramsey et al. Drug Therapy vol. 335 No. 3 179-188.

Kusumi et al. Bioorganic & Medicinal Chemistry Letters 26 (2016) 1209-1213.

Kusumi et al. Bioorganic & Medicinal Chemistry Letters 25 (2015) 4387-4392.

\* cited by examiner

[Fig.1]
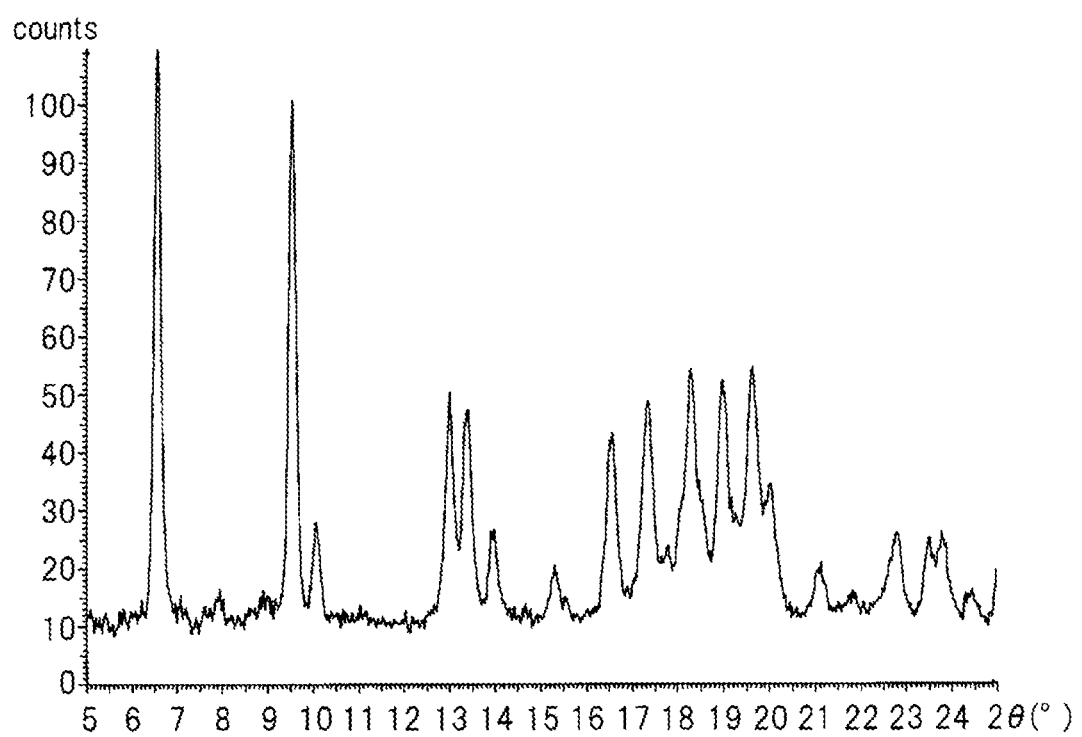

[Fig.2]
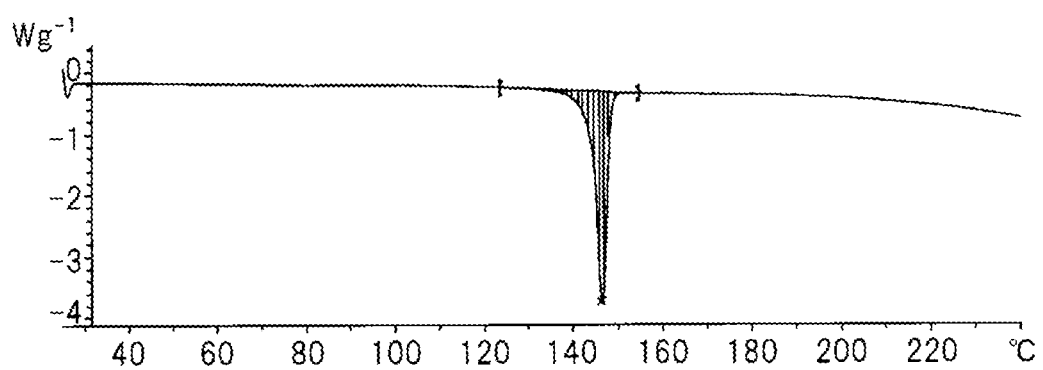

[Fig.3]
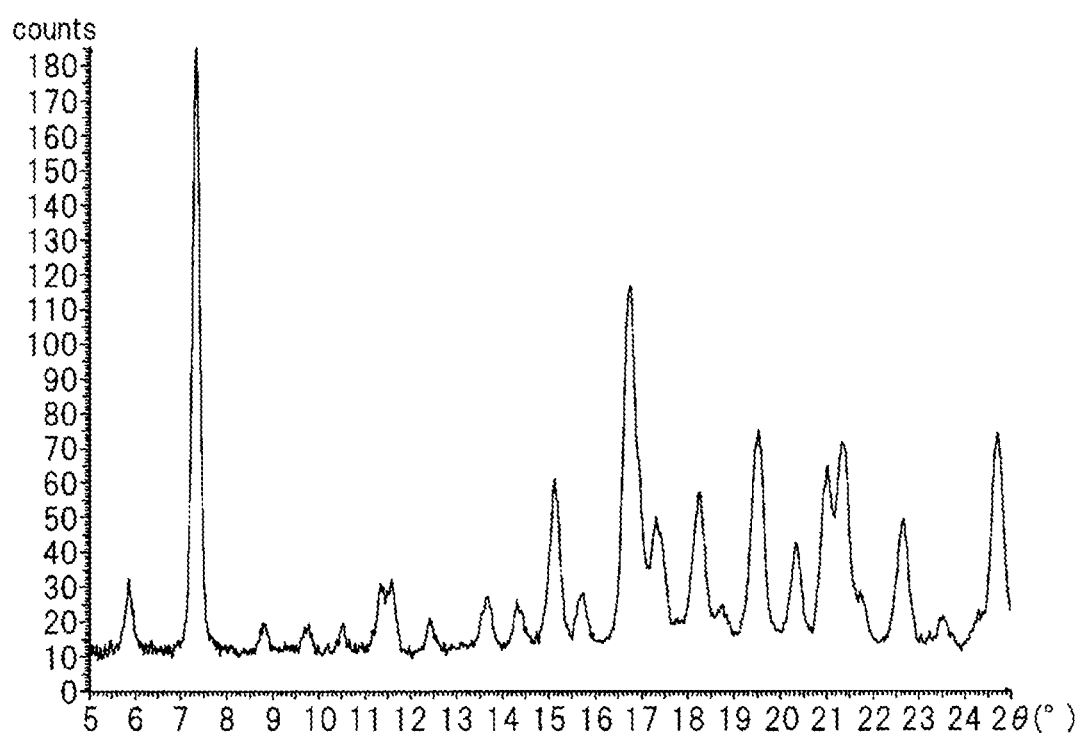

[Fig.4]
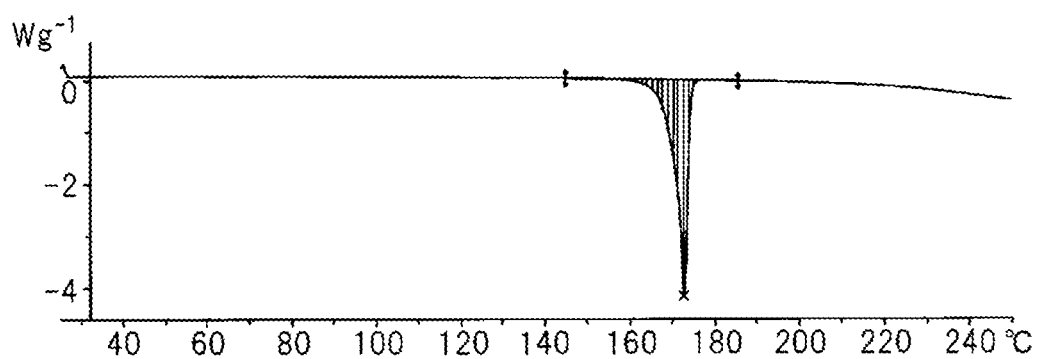

[Fig.5]
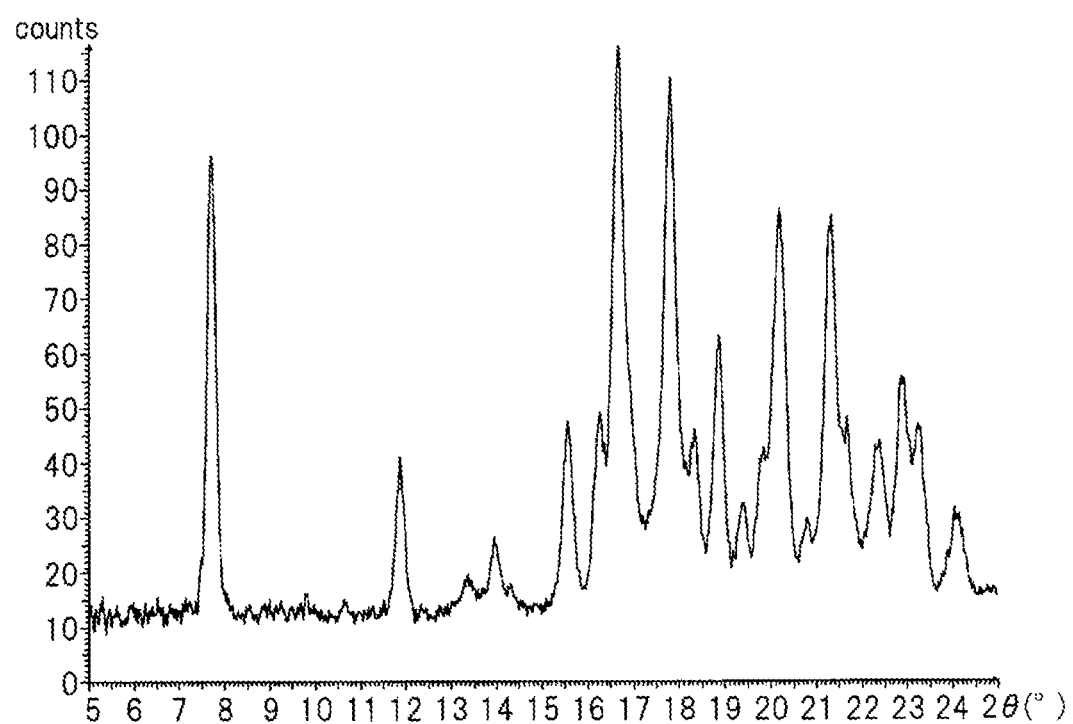

[Fig.6]
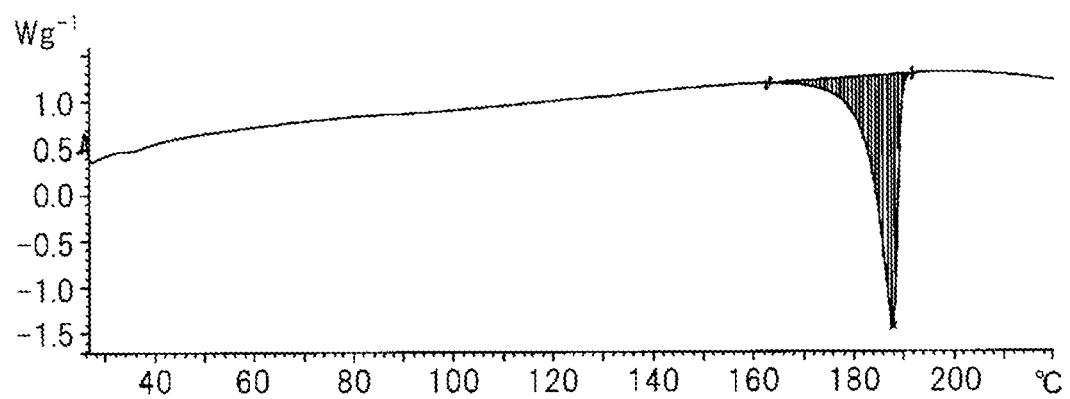

PHENYL DERIVATIVE

CROSS REFERENCE TO RELATED APPLICATION

This is a Division of U.S. patent application Ser. No. 15/784,376 filed Oct. 16, 2017 (allowed), which is a Divisional of U.S. patent application Ser. No. 15/089,690 filed Apr. 4, 2016 (issued as U.S. Pat. No. 9,820,980 on Nov. 21, 2017) which is a Divisional of U.S. patent application Ser. No. 14/592,100 filed Jan. 8, 2015 (issued as U.S. Pat. No. 9,340,499 on May 17, 2016), which is a Continuation of U.S. application Ser. No. 14/347,178 filed Mar. 25, 2014 (issued as U.S. Pat. No. 8,975,409 on Mar. 10, 2015), which is a National Stage Entry of PCT International Application No. PCT/JP2012/074968 filed Sep. 27, 2012, which claims benefit of Japanese Patent Application No. 2011-213987 filed Sep. 29, 2011 of which disclosures are incorporated herein by reference in their entirety.

TECHNICAL FIELD

The present invention relates to a compound represented by the formula (I-1):

[C 1]

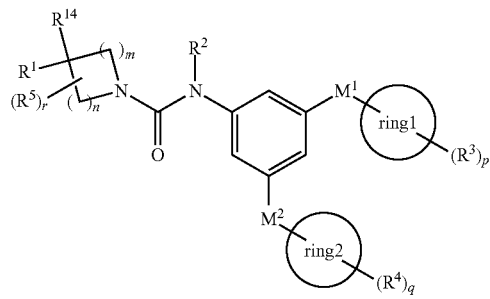

(I-1)

wherein all the symbols have the same meanings as described hereinbelow, and a salt thereof, a solvate thereof, an N-oxide thereof or a prodrug thereof (hereinafter sometimes abbreviated as the present compound).

BACKGROUND ART

Sphingosine-1-phosphate [(2S,3R,4E)-2-amino-3-hydroxyoctadeca-4-enyl-1-phosphate; hereinafter sometimes abbreviated as S1P] is a lipid which is synthesized by metabolic turnover of sphingolipids or extracellular action of secretory sphingosine kinases. It is proposed that this lipid acts as an intercellular transmitter and an intracellular secondary transmitter.

With regard to $S1P_2$ (EDG-5/AGR16/H218) receptors among S1P receptors, it has been published that the strong expression of mRNA thereof is confirmed in tissues of heart, lung, stomach and small intestine and that the expression amount of mRNA thereof in intimal cells in model mice of carotid balloon injury which are the model for coronary arteriosclerosis is significantly decreased compared to normal intimal cells (see Patent Document 1).

It is also reported that S1P receptors (particularly $S1P_2$ receptors) are involved in portal hypertension, asthma and the like (see Non Patent Document 1) It is also known that the receptors are involved in expression of connective tissue growth factors (CTGFs) associated with onset of fibrosis, cancer and the like (see Non Patent Document 2).

The following compounds are known as the related art of the present invention.

As the compounds having $S1P_2$ antagonistic activity, pyrazopyridine compounds or pharmaceutically acceptable salts thereof represented by the formula (a):

[C 2]

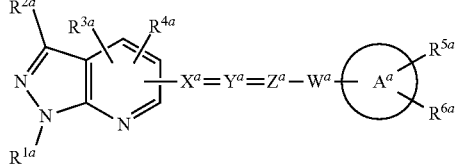

(a)

wherein $R^{1a}$, $R^{2a}$ and $R^{3a}$ represent a C1-8 alkyl group and the like; $R^{4a}$ represents a hydrogen atom and the like; $R^{5a}$ and $R^{6a}$ are the same or different and represent a hydrogen atom, a C1-8 alkyl group, a C1-6 alkoxy group, a halogen atom and the like; $X^a$ represents —NH—, —O—, —CH$_2$— and the like; $Y^a$ represents —NH— and the like; $Z^a$ represents —CO— and the like; $W^a$ represents —NH— and the like; and the ring $A^a$ represents an aryl group, a heteroaryl group and the like (the definitions of respective groups are abstracted), have been disclosed which specifically act on $S1P_2$ receptors and are useful as therapeutics for fibrosis (see Patent Document 2).

The known compounds having $S1P_2$ antagonistic activity also include compounds having a piperidine skeleton represented by the formula (b):

[C 3]

$$A^b\text{-}X^b\text{—}Y^b\text{—}Z^b\text{—}B^b \qquad (b)$$

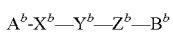

wherein $A^b$ represents a cyclic group which may contain a substituent; $X^b$ represents a single bond or a spacer having 1 to 3 atoms in the main chain; $Y^b$ represents a single bond or a spacer having 1 to 3 atoms in the main chain; $Z^b$ is a single bond or a spacer having 1 to 3 atoms in the main chain; and $B^b$ represents a cyclic group which may contain a substituent (see Patent Document 3) and compounds having an azetidine skeleton (see Patent Document 4).

Meanwhile, as the compounds having a benzene skeleton substituted with two cyclic groups, the compounds represented by the formula (c):

[C 4]

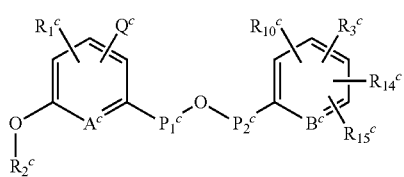

(c)

wherein $P_1^c$ and $P_2^c$ independently represent a bond or a $C_{1-3}$ alkyl; $A^c$ represents CH or N; $B^c$ represents CH or N; $R_1^c$ represents a hydrogen, an amino, —$NR_4^c$—CO—$Z^cR_9^cR_{13}^c$ and the like; $R_3^c$ represents —$C(NR_{17}^c)NH_2$ or when $A^c$ is CH, $R_3^c$ also represents an amino $C_{1-7}$ alkyl; $R_{10}^c$, $R_{14}^c$ and $R_{15}^c$ independently represent a hydrogen, a halogen, a $C_{1-7}$ alkyl and the like; $Q^c$ represents a hydrogen or a halogen; $R_4^c$ represents a hydrogen or a $C_{1-7}$ alkyl; $Z^c$ is a 5- to 12-membered saturated, partially saturated or aromatic ring which may be monocyclic or bicyclic; $R_9^c$ and $R_{13}^c$ independently represent a hydrogen, a halogen, a $C_{1-7}$ alkyl and the like; $R_2^c$ represents a $C_{1-7}$ alkyl, a phenyl which may be substituted and the like; and $R_{17}^c$ represents a hydrogen, —OH, a $C_{1-7}$ alkoxy and the like (the definitions of respective groups are abstracted), are known as matriptase inhibitors (see Patent Document 5).

No prior art documents discloses or suggests that the compound of the invention which contains two cyclic groups, particularly phenoxy groups at specific substitution positions have significantly improved human $S1P_2$ antagonistic activity.

Patent Document 1: Japanese Patent Application Laid-open No. H6-234797
Patent Document 2: WO 01/98301
Patent Document 3: WO 2004/002531
Patent Document 4: WO 2005/063704
Patent Document 5: WO 2010/133748
Non Patent Document 1: Biochemical and Biophysical Research Communications, vol. 320, No. 3, p. 754-759, 2004
Non Patent Document 2: Molecular Cancer Research, vol. 6, No. 10, p. 1649-1656, 2008

DISCLOSURE OF THE INVENTION

A problem of the present invention is to find a compound having human $S1P_2$ antagonistic activity which was insufficiently exhibited by the compounds disclosed in Patent Document 3, to improve the solubility of the compound and to provide a medicinal product thereof.

The present inventors have carried out extensive studies in order to solve the above problem to find the compound having improved human $S1P_2$ antagonistic activity. As a result, the present inventors have found that the compound having two cyclic groups, particularly phenoxy groups, at certain substitution positions have significantly improved human $S1P_2$ antagonistic activity compared to the compounds disclosed in Patent Document 3, thereby completing the present invention.

Thus the present invention relates to:
[1] a compound represented by the formula (I-1):

[C 5]

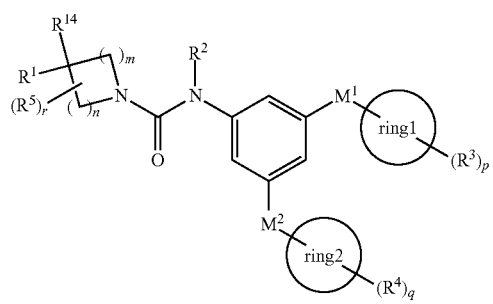

(I-1)

wherein $R^1$ represents (1) a C1-8 alkyl group which may be substituted with 1 to 5 $R^{21}$ group(s), (2) a C2-8 alkenyl group which may be substituted with 1 to 5 $R^{21}$ group(s), (3) a C2-8 alkynyl group which may be substituted with 1 to 5 $R^{21}$ group(s), (4) a C3-7 carbocycle which may be substituted with 1 to 5 substituent(s) selected from the group consisting of a C1-4 alkyl group, a C1-4 haloalkyl group, a C1-4 alkoxy group and a halogen atom, or (5) —$CONR^{31}R^{32}$;

$R^{21}$ represents (1) a halogen atom, (2) —$OR^{22}$ (wherein, $R^{22}$ represents (1) a hydrogen atom, (2) a C1-4 alkyl group or (3) a C1-4 haloalkyl group), (3) —$NR^{23}R^{24}$ (wherein, $R^{23}$ and $R^{24}$ each independently represent (1) a hydrogen atom or (2) a C1-4 alkyl group) or (4) an oxo group;

$R^{31}$ and $R^{32}$ each independently represent (1) a hydrogen atom or (2) a C1-4 alkyl group;

$R^2$ represents (1) a hydrogen atom, (2) a C1-4 alkyl group or (3) a C1-4 haloalkyl group;

$R^3$ and $R^4$ each independently represent (1) a halogen atom, (2) a C1-4 alkyl group, (3) a C1-4 haloalkyl group, (4) a C1-4 alkoxy group, (5) a hydroxy group, (6) -L-$CONR^6R^7$, (7) -L-$SO_2R^8$ or (8) -L-$COOR^9$;

$R^5$ represents (1) a halogen atom, (2) a C1-4 alkyl group or (3) a C1-4 haloalkyl group;

L represents (1) a bond, (2) a group represented by the formula:

[C 6]

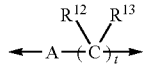

wherein A represents (1) a bond or (2) an oxygen atom; $R^{12}$ and $R^{13}$ each independently represent (1) a hydrogen atom, (2) a C1-4 alkyl group, (3) a hydroxy group or (4) $NH_2$ or (5) $R^{12}$ and $R^{13}$ together with the carbon atom to which they are attached may form a C3-7 carbocycle; and the arrow on the right hand side binds to —$CONR^6R^7$, —$SO_2R^8$ or —$COOR^9$, (3) a C2-4 alkenylene group, (4) a —O—C2-4 alkenylene group, (5) an oxygen atom or (6) a nitrogen atom which may be substituted with a C1-4 alkyl group;

$R^6$ and $R^7$ each independently represent (1) a hydrogen atom, (2) a C1-4 alkyl group, (3) a C1-4 haloalkyl group, (4) a hydroxy group, (5) —$CONR^{15}R^{16}$, (6) —$SO_2NR^{15}R^{16}$, (7) —$COR^{17}$ or (8) —$SO_2R^{17}$, or $R^6$ and $R^7$ together with the nitrogen atom to which they are attached may form a 4- to 7-membered nitrogen-containing saturated heterocycle that may be substituted with a hydroxy group;

$R^8$ represents (1) a C1-4 alkyl group, (2) a C1-4 haloalkyl group or (3) $NR^{10}R^{11}$;

$R^9$ represents (1) a hydrogen atom or (2) a C1-8 alkyl group;

$R^{10}$ and $R^{11}$ each independently represent (1) a hydrogen atom, (2) a C1-4 alkyl group, (3) —$CONR^{15}R^{16}$, (4) —$SO_2NR^{15}R^{16}$, (5) —$COR^{17}$ or (6) —$SO_2R^{17}$;

the ring 1 and the ring 2 each independently represent a 5- to 7-membered cyclic group;

$R^{14}$ represents (1) a hydrogen atom or (2) a hydroxy group;

$R^{15}$ and $R^{16}$ each independently represent (1) a hydrogen atom, (2) a C1-4 alkyl group or (3) a 5- to 7-membered cyclic group;

$R^{17}$ represents (1) a C1-4 alkyl group or (2) a 5- to 7-membered cyclic group;

$M^1$ and $M^2$ each independently represent (1) a bond, (2) —C(O)—, (3) —O—, (4) —S—, (5) —C(O)O—, (6) —$CH_2O$— or (7) —C(O)NH—;

n represents an integer of 1 to 2;
m represents an integer of 1 to 2;
p represents an integer of 0 to 5;
q represents an integer of 0 to 5;

r represents an integer of 0 to 4;
t represents an integer of 1 to 4;
when p is 2 or more, a plurality of $R^3$ groups may be the same or different;
when q is 2 or more, a plurality of $R^4$ groups may be the same or different;
when r is 2 or more, a plurality of $R^5$ groups may be the same or different; and
when t is 2 or more, a plurality of $R^{12}$ and $R^{13}$ groups may be respectively the same or different;
a salt thereof, a solvate thereof, an N-oxide thereof or a prodrug thereof;
[2] the compound according to [1], wherein $R^{14}$ is a hydroxy group;
[3] the compound according to [1] or [2], wherein $M^1$ and $M^2$ each independently are (1) —C(O)—, (2) —O—, (3) —S—, (4) —C(O)O— or (5) —CH$_2$O—;
[4] the compound according to [3], wherein $M^1$ and $M^2$ are —O—;
[5] the compound according to [1], which is represented by the formula (I):

[C 7]

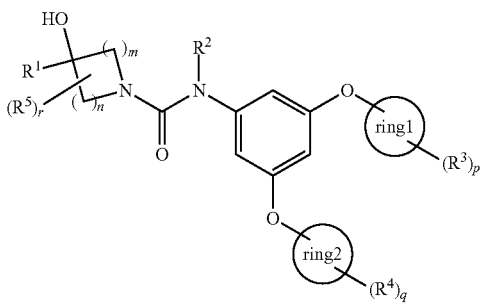

wherein all the symbols have the same meanings as above;
[6] the compound according to [5], wherein $R^1$ is (1) a C1-8 alkyl group which may be substituted with 1 to 5 $R^{21}$ group(s) or (2) a C3-7 carbocycle which may be substituted with 1 to 5 substituent(s) selected from the group consisting of a C1-4 alkyl group, a C1-4 alkoxy group, a halogen atom and a trifluoromethyl group;
[7] the compound according to [5] or [6], wherein $R^2$ is a hydrogen atom;
[8] the compound according to any of [5] to [7], wherein the ring 1 and the ring 2 each independently are (1) a benzene, (2) cyclohexane or (3) pyridine ring;
[9] the compound according to any of [1] to [8], which is (1) 4-(2-ethylbutyl)-N-{3-[4-(ethylcarbamoyl)phenoxy]-5-(4-fluorophenoxy)phenyl}-4-hydroxy-1-piperidinecarboxamide, (2) 4-[3-(4-fluorophenoxy)-5-({[4-(4-fluorophenyl)-4-hydroxy-1-piperidinyl]carbonyl}amino)phenoxy]benzoic acid, (3) 4-(2-ethylbutyl)-N-[3-(4-fluorophenoxy)-5-{4-[(4-hydroxy-1-piperidinyl)carbonyl]phenoxy}phenyl]-4-hydroxy-1-piperidinecarboxamide, (4) 2-{4-[3-(4-fluorophenoxy)-5-{[(4-hydroxy-4-isobutyl-1-piperidinyl)carbonyl]amino}phenoxy]phenyl}-2-methylpropanoic acid, (5) 1-{4-[3-(4-fluorophenoxy)-5-({[4-hydroxy-4-(3-pentanyl)-1-piperidinyl]carbonyl}amino)phenoxy]phenyl}cyclopropanecarboxylic acid, (6) 2-{4-[3-(4-fluorophenoxy)-5-{[(3-hydroxy-3-isobutyl-1-azetidinyl)carbonyl]amino}phenoxy]phenyl}-2-methylpropanoic acid, (7) 4-[3-({[4-(2-ethylbutyl)-4-hydroxy-1-piperidinyl]carbonyl}amino)-5-(4-fluorophenoxy)phenoxy]benzoic acid, (8) 2-{4-[3-({[4-(2-ethylbutyl)-4-hydroxy-1-piperidinyl]carbonyl}amino)-5-(4-fluorophenoxy)phenoxy]phenyl}-2-methylpropanoic acid or (9) 2-(4-{[3-(4-fluorophenoxy)-5-{[(4-hydroxy-4-isobutyl-1-piperidinyl)carbonyl]amino}benzoyl]oxy}phenyl)-2-methylpropanoic acid;
[10] a pharmaceutical composition containing the compound represented by the formula (I-1) according to [1], the salt thereof, the solvate thereof, the N-oxide thereof or the prodrug thereof;
[11] the pharmaceutical composition according to [10], which is a $S1P_2$ antagonist;
[12] the pharmaceutical composition according to [10], which is a prophylactic and/or therapeutic agent for a $S1P_2$-mediated disease;
[13] the pharmaceutical composition according to [12], wherein the $S1P_2$-mediated disease is a disease resulting from vascular constriction, fibrosis, respiratory disease, arteriosclerosis, peripheral arterial occlusive disease, retinopathy, glaucoma, age-related macular degeneration, nephritis, diabetes, dyslipidemia, hepatitis, hepatic cirrhosis, hepatic failure, neuropathy, rheumatoid arthritis, wound, pain, urticaria, systemic lupus erythematosus (SLE) or cancer;
[14] the pharmaceutical composition according to [13], wherein the disease resulting from vascular constriction is cerebral vasospastic disease, cardiac vasospastic disease, coronary vasospastic disease, hypertension, pulmonary hypertension, myocardial infarction, angina, arrhythmia, portal hypertension, varix or ischemia-reperfusion injury;
[15] the pharmaceutical composition according to [13], wherein the fibrosis is pulmonary fibrosis, hepatic fibrosis, kidney fibrosis, myocardial fibrosis or skin fibrosis;
[16] the pharmaceutical composition according to [13], wherein the respiratory disease is bronchial asthma, acute lung injury, sepsis or chronic obstructive pulmonary disease;
[17] a method of preventing and/or treating a $S1P_2$-mediated disease, comprising administering to a mammal an effective amount of the compound represented by the formula (I-1) according to [1], the salt thereof, the solvate thereof, the N-oxide thereof or the prodrug thereof;
[18] a compound represented by the formula (I-1) according to [1], the salt thereof, the solvate thereof, the N-oxide thereof or the prodrug thereof in use for prophylaxis and/or therapy of a $S1P_2$-mediated disease; and
[19] use of the compound represented by the formula (I-1) according to [1], the salt thereof, the solvate thereof, the N-oxide thereof or the prodrug thereof for producing a prophylactic and/or therapeutic agent for a $S1P_2$-mediated disease.

The present compound has strong human $S1P_2$ antagonistic activity, and thus is useful for therapy of $S1P_2$-mediated diseases such as diseases resulting from vascular constriction and fibrosis.

BRIEF DESCRIPTION OF THE DRAWINGS

FIG. 1 is an X-ray powder diffraction spectrum chart of a crystal of the present compound (Example A);
FIG. 2 is a differential scanning calorimetric (DSC) chart of a crystal of the present compound (Example A);
FIG. 3 is an X-ray powder diffraction spectrum chart of a crystal of the present compound (Example B);
FIG. 4 is a differential scanning calorimetric (DSC) chart of a crystal of the present compound (Example B);
FIG. 5 is an X-ray powder diffraction spectrum chart of a crystal of the present compound (Example C); and
FIG. 6 is a differential scanning calorimetric (DSC) chart of a crystal of the present compound (Example C).

BEST MODE FOR CARRYING OUT THE INVENTION

The present invention is described in detail hereinbelow.

The halogen atom as used herein may include fluorine, chlorine, bromine or iodine.

The C1-8 alkyl group as used herein may include linear or branched C1-8 alkyl groups which may include, for example, methyl, ethyl, propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl or 1,1-diethylbutyl groups.

The C1-4 alkyl group as used herein may include linear or branched C1-4 alkyl groups which may include, for example, methyl, ethyl, propyl, butyl, isopropyl, isobutyl, sec-butyl or tert-butyl groups.

The C1-4 haloalkyl group as used herein may include a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group or a 4-bromobutyl group.

The C2-8 alkenyl group as used herein may include linear or branched C2-8 alkenyl groups which may include, for example, vinyl, propenyl, butenyl, pentenyl, hexenyl, hexadienyl, heptenyl, heptadienyl, octenyl, octadienyl, 2-methylpropen-1-yl, 2-ethyl-1-buten-1-yl, 2-methylbuten-2-yl or 2-methylpenten-2-yl groups.

The C2-4 alkenylene group as used herein may include ethenylene, propenylene or butenylene groups.

The C2-8 alkynyl group as used herein may include linear or branched C2-8 alkynyl groups which may include, for example, ethynyl, propynyl, butynyl, pentynyl, hexynyl, hexadiynyl, heptynyl, heptadiynyl, octynyl, octadiynyl or 3,3-dimethyl-1-butyn-1-yl groups.

The C1-4 alkoxy group as used herein may include, for example, methoxy, ethoxy, propoxy, isopropoxy, butoxy, isobutoxy, sec-butoxy or tert-butoxy groups.

The C3-7 carbocycle as used herein means a C3-7 monocyclic carbocycle or a C3-7 carbocycle which may be partially or fully saturated and may include, for example, cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene or benzene rings.

The C5-7 carbocycle as used herein means a C5-7 monocyclic carbocycle or a C5-7 carbocycle which may be partially or fully saturated and may include, for example, cyclopentane, cyclohexane, cycloheptane, cyclopentene, cyclohexene, cycloheptene, cyclopentadiene, cyclohexadiene, cycloheptadiene or benzene rings.

The 4- to 7-membered nitrogen-containing saturated heterocycle as used herein refers to partially or fully saturated 4- to 7-membered monocyclic heterocycles which contain 1 to 5 hetero atoms selected from an oxygen atom, a nitrogen atom and a sulphur atom and inevitably contain one or more nitrogen atoms. For example, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine or thiomorpholine rings may be mentioned.

The 5- to 7-membered cyclic group as used herein means a C5-7 carbocycle and a 5- to 7-membered heterocycle. The C5-7 carbocycle has the same meaning as above and the 5- to 7-membered heterocycle may include 5- to 7-membered unsaturated heterocycles and 5- to 7-membered saturated heterocycles. The 5- to 7-membered heterocycles may include, for example, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiopehene, tetrahydrothiopehene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiopehene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine or thiadiazepine rings.

In the present invention, $R^1$ is preferably a C1-8 alkyl group which may be substituted with 1 to 5 $R^{21}$ group(s) or a C3-7 carbocycle which may be substituted with 1 to 5 substituent(s) selected from the group consisting of a C1-4 alkyl group, a C1-4 haloalkyl group, a C1-4 alkoxy group and a halogen atom, and more preferably a branched C1-8 alkyl group or a benzene, cyclopropane, cyclopentane, cyclohexane or cycloheptane ring which may be substituted with 1 to 5 substituent(s) selected from the group consisting of a halogen atom and a trifluoromethyl group. The branched C1-8 alkyl group is preferably an isopropyl, isobutyl, 2-ethylbutyl, 2-methylpentyl or 3-methylpentyl group.

In the present invention, $R^2$ is preferably a hydrogen atom.

In the present invention, $R^3$ is preferably a halogen atom or -L-COOR$^9$.

In the present invention, $R^4$ is preferably a halogen atom or -L-COOR$^9$.

In the present invention, $R^5$ is preferably a halogen atom or a C1-4 alkyl group.

In the present invention, the ring 1 is preferably a benzene, pyridine or cyclohexane ring and more preferably a benzene ring.

In the present invention, the ring 2 is preferably a benzene, pyridine or cyclohexane ring and more preferably a benzene ring.

In the present invention, $R^{14}$ is preferably a hydroxy group.

In the present invention, when $M^1$ represents —C(O)O—, —CH$_2$O— or —C(O)NH—, the orientation of binding of the respective groups is not particularly limited; however it is preferable that the bond on the right hand side of the respective groups binds to the ring 1.

In the present invention, when $M^2$ represents —C(O)O—, —CH$_2$O— or —C(O)NH—, the orientation of binding of the respective groups is not particularly limited; however it is preferable that the bond on the right hand side of the respective groups binds to the ring 2.

In the present invention, $M^1$ is preferably —C(O)—, —O—, —S—, —C(O)O— or —CH$_2$O— and more preferably —O—.

In the present invention, $M^2$ is preferably —C(O)—, —O—, —S—, —C(O)O— or —CH$_2$O— and more preferably —O—.

In the present invention, the compound represented by the formula (I-1) is preferably the compound represented by the formula (I).

In the present invention, the preferable compounds include the compounds described in Examples and more preferably (1) 4-(2-ethylbutyl)-N-{3-[4-(ethylcarbamoyl)phenoxy]-5-(4-fluorophenoxy)phenyl}-4-hydroxy-1-piperidine carboxamide, (2) 4-[3-(4-fluorophenoxy)-5-({[4-(4-fluorophenyl)-4-hydroxy-1-piperidinyl]carbonyl}amino)phenoxy]benzoic acid, (3) 4-(2-ethylbutyl)-N-[3-(4-fluorophenoxy)-5-{4-[(4-hydroxy-1-piperidinyl)carbonyl]phenoxy}phenyl]-4-hydroxy-1-piperidine carboxamide, (4) 2-{4-[3-(4-fluorophenoxy)-5-{[(4-hydroxy-4-isobutyl-1-piperidinyl)carbonyl]amino}phenoxy]phenyl}-2-methylpropanoic acid, (5) 1-{4-[3-(4-fluorophenoxy)-5-({[4-hydroxy-4-(3-pentanyl)-1-piperidinyl]carbonyl}amino)phenoxy]phenyl}cyclopropanecarboxylic acid, (6) 2-{4-[3-(4-fluorophenoxy)-5-{[(3-hydroxy-3-isobutyl-1-azetidinyl)carbonyl]amino}phenoxy]phenyl}-2-methylpropanoic acid, (7) 4-[3-({[4-(2-ethylbutyl)-4-hydroxy-1-piperidinyl]carbonyl}amino)-5-(4-fluorophenoxy)phenoxy]benzoic acid, (8) 2-{4-[3-({[4-(2-ethylbutyl)-4-hydroxy-1-piperidinyl]carbonyl}amino)-5-(4-fluorophenoxy)phenoxy]phenyl}-2-methylpropanoic acid, and (9) 2-(4-{[3-(4-fluorophenoxy)-5-{[(4-hydroxy-4-isobutyl-1-piperidinyl)carbonyl]amino}benzoyl]oxy}phenyl)-2-methylpropanoic acid.

[Isomers]

The present invention encompasses all isomers unless particularly stated. For example, the alkyl group includes linear and branched groups. Moreover, the present invention encompasses geometrical isomers for double bonds, rings and condensed rings (E-forms, Z-forms, cis forms and trans forms), optical isomers due to asymmetrical carbon atoms (R and S forms, α and β configurations, enantiomers and diastereomers), optically active substances having optical rotating activity (D, L, d and l forms), polar substances which can be separated by chromatography (high polarity substances and low polarity substances), equilibrium compounds, rotamers, mixtures thereof at arbitrary proportions and racemic mixtures. The present invention also encompasses tautomers.

The optical isomers according to the present invention may include not only the ones with 100% purity but also the ones containing other optical isomers at less than 50%.

In the present invention, unless particularly stated, the symbol:

[C 8] 

indicates that the bond projects below the plane of the paper (i.e. α configuration), the symbol:

[C 9] 

indicates that the bond projects above the plane of the paper (i.e. β configuration), and the symbol:

[C 10] 

indicates that the bond is the α configuration, the β configuration or the mixture of these configurations at arbitrary proportions, as apparent to a person skilled in the art.

The compound represented by the formula (I-1) is converted to a salt by the well-known method. The salt is preferably water-soluble. Appropriate salts may include alkali metal (potassium, sodium and the like) salts, alkaline earth metal (calcium, magnesium and the like) salts, ammonium salts, pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like) salts, acid addition salts (inorganic acid salts (hydrochlorides, hydrobromides, hydroiodides, sulphates, phosphates, nitrates and the like), organic acid salts (acetates, trifluoroacetates, lactates, tartrates, oxalates, fumarates, maleates, benzoates, citrates, methanesulphonates, ethanesulphonates, benzenesulphonates, toluenesulphonates, isethionates, glucuronates, gluconates and the like) and the like) and the like.

The compound represented by the formula (I-1) and the salt thereof can also be converted to a solvate. The solvate preferably has low toxicity and is water-soluble. Appropriate solvates may include, for example, solvates with water and alcoholic solvents (e.g. ethanol).

The N-oxide of the compound represented by the formula (I-1) refers to the compound represented by the formula (I-1) in which the nitrogen atom is oxidized. The N-oxide of the compound represented by the formula (I-1) may also be the alkali (alkaline earth) metal salt, the ammonium salt, the organic amine salt and the acid addition salt as described above.

The prodrug of the compound represented by the formula (I-1) refers to a compound which is converted in vivo to the compound represented by the formula (I-1) by the reaction with enzymes, gastric acid and the like. The prodrug of the compound represented by the formula (I-1) may include, when the compound represented by the formula (I-1) has a hydroxy group, compounds in which the hydroxy group is acylated, alkylated, phosphorylated or converted to borate (e.g. the present compounds in which the hydroxy group is converted to acetyl, palmitoyl, propanoyl, pivaloyl, succinyl, fumaryl, alanyl, dimethylaminomethylcarbonyl or the like); compounds represented by the formula (I-1) in which the carboxyl group is esterified or amidated (e.g. compounds represented by the formula (I-1) in which the carboxyl group is converted to ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide or the like) and the like. These compounds can be produced by the well-known methods. The prodrug of the compound represented by the formula (I-1) may be hydrates or non-hydrates. The prodrug of the compound represented by the formula (I-1) may be the one which is converted to the compound represented by the formula (I-1) under the physiological condition such as those disclosed in "Iyakuhin no Kaihatsu", vol. 7 "Bunshi Sekkei", p. 163-198, 1990, Hirokawa Shoten Co. The compound represented by the formula (I-1) may be labelled with an isotope (for example, $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$ and the like).

[Production Method of the Present Compound]

The present compound can be produced by well-known methods, for example, the method described in Comprehensive Organic Transformations: A Guide to Functional Group Preparations, 2nd Edition (Richard C. Larock, John Wiley & Sons Inc, 1999) or the method described in Examples with appropriate modifications and combinations.

The compound having the formula (I) in which $R^2$ is a hydrogen atom, namely the compound represented by the formula (I-A):

[C 11]

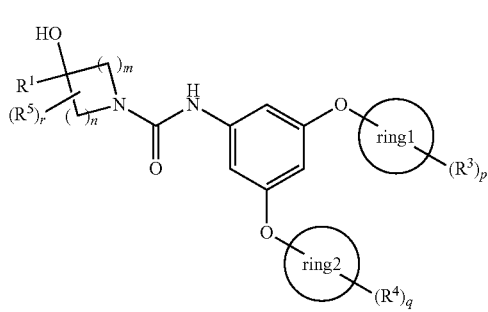

(I-A)

wherein all the symbols have the same meanings as above, can be produced as shown in the following reaction step formula 1:

[C 12]

Reaction Step Formula 1

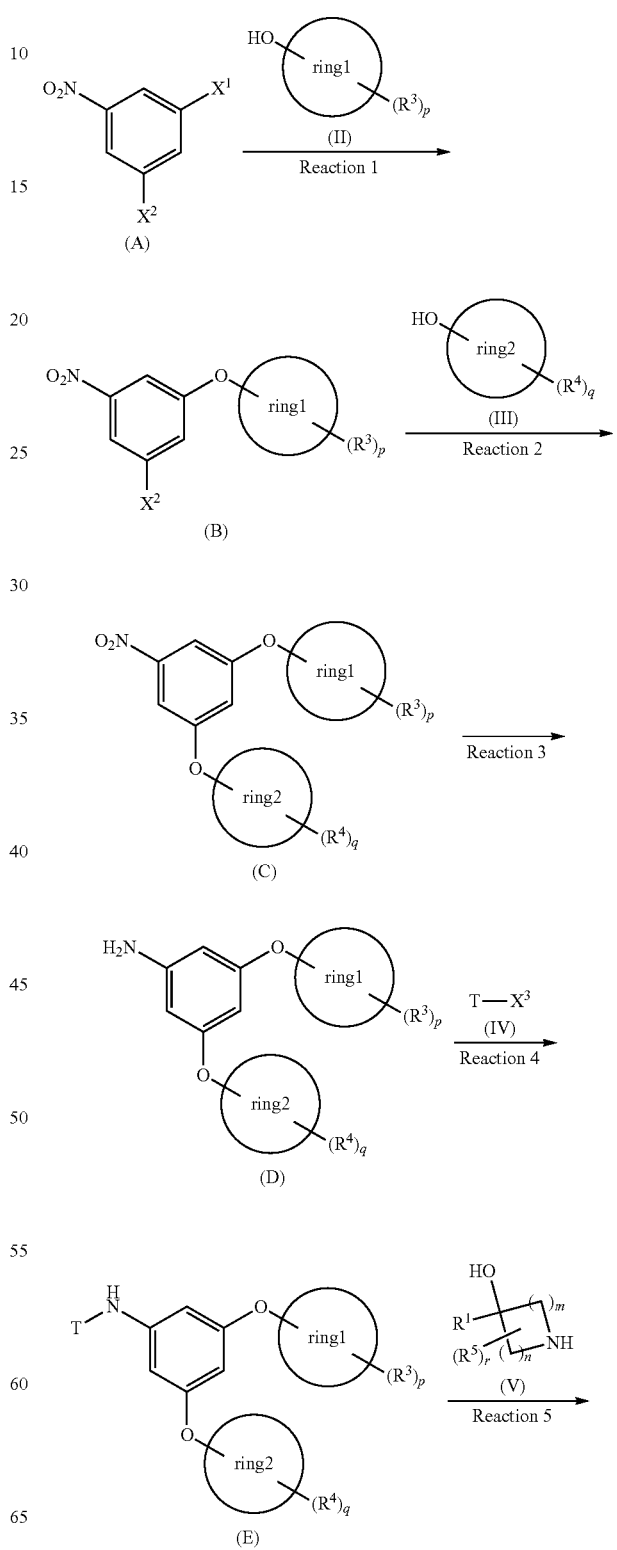

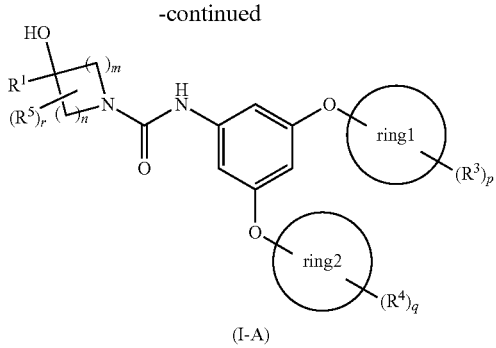

(I-A)

wherein T represents a protecting group of the amino group having the carbonyl group (e.g. a 2,2,2-trichloroethoxycarbonyl(Troc) group, a phenoxycarbonyl group, a p-nitrophenoxycarbonyl group and the like); $X^1$, $X^2$ and $X^3$ each independently represent a halogen atom and $X^1$, $X^2$ and $X^3$ may be the same or different; and other symbols have the same meanings as above.

In the reaction step formula 1, the reaction 1 can be carried out as an etherification reaction between the compound represented by the formula (A) and the compound represented by the formula (II). This etherification reaction is well known and is carried out, for example, in an organic solvent (N,N-dimethylacetamide, N,N-dimethylformamide, dimethyl sulphoxide, chloroform, dichloromethane, diethyl ether, tetrahydrofuran, methyl t-butyl ether and the like), in the presence of an alkali metal hydroxide (sodium hydroxide, potassium hydroxide, lithium hydroxide and the like), an alkali metal hydride (sodium hydride and the like), an alkaline earth metal hydroxide (barium hydroxide, calcium hydroxide and the like), a phosphate (potassium phosphate and the like) or a carbonate (caesium carbonate, sodium carbonate, potassium carbonate and the like) or an aqueous solution thereof or a mixture thereof and at 0 to 100° C.

In the reaction step formula 1, the reaction 2 can be carried out as an etherification reaction, as the reaction 1, using the compound represented by the formula (B) and the compound represented by the formula (III).

In the reaction step formula 1, the reaction 3 can be carried out as a reduction reaction of the nitro group of the compound represented by the formula (C). The reduction reaction of the nitro group is well known and is carried out, for example, by the methods described hereinbelow.

(1) The reaction is carried out, for example, in a solvent [ethers (tetrahydrofuran, dioxane, dimethoxyethane, diethyl ether and the like), alcohols (methanol, ethanol and the like), benzenes (benzene, toluene and the like), ketones (acetone, methyl ethyl ketone and the like), nitriles (acetonitrile and the like), amides (dimethylformamide and the like), water, ethyl acetate, acetic acid or mixed solvents of two or more of the above], in the presence of a hydrogenation catalyst (palladium-carbon, palladium black, palladium, palladium hydroxide, platinum dioxide, platinum-carbon, nickel, Raney nickel, ruthenium chloride and the like), in the presence or absence of an acid (hydrochloric acid, sulphuric acid, hypochlorous acid, boric acid, tetrafluoroboric acid, acetic acid, p-toluenesulphonic acid, oxalic acid, trifluoroacetic acid, formic acid and the like), in an hydrogen atmosphere of normal or increased pressure, in the presence of ammonium formate or hydrazine and at a temperature of 0 to 200° C.

(2) The reaction is carried out, for example, in a water-miscible solvent (ethanol, methanol, tetrahydrofuran and the like), in the presence or absence of an acid (hydrochloric acid, hydrobromic acid, ammonium chloride, acetic acid, ammonium formate and the like), by using a metal reagent (zinc, iron, tin, tin chloride, iron chloride, samarium, indium, sodium borohydride-nickel chloride and the like) at a temperature of 0 to 150° C.

In the reaction step formula 1, the reaction 4 is well known and is carried out with the compound represented by the formula (D) and the compound represented by the formula (IV), for example, by reaction of the compound represented by the formula (IV) in the presence of a base (pyridine, triethylamine, dimethylaniline, dimethylaminopyridine, diisopropylethylamine and the like) with the compound represented by the formula (D) in an organic solvent (chloroform, dichloromethane, diethyl ether, tetrahydrofuran and the like) at a temperature of 0 to 40° C. The compound represented by the formula (IV) can also be subjected to the reaction with the formula (D) in an organic solvent (ethyl acetate, dioxane, tetrahydrofuran and the like), with using an alkaline aqueous solution (sodium hydrogen carbonate solution, sodium hydroxide solution and the like) at 0 to 40° C.

In the reaction step formula 1, the reaction 5 is well known and is carried out with the compound represented by the formula (E) and the compound represented by the formula (V), for example, by reaction of the compound represented by the formula (E) in the presence of a base (pyridine, triethylamine, dimethylaniline, dimethylaminopyridine, diisopropylethylamine and the like) with the compound represented by the formula (V) in an organic solvent (N,N-dimethylacetamide, chloroform, dichloromethane, diethyl ether, tetrahydrofuran and the like) at a temperature of 0° C. to a reflux temperature.

In the reaction step formula 1, when the compound represented by the formula has a protecting group, for example, when $R^3$ or $R^4$ is protected, deprotection reaction may be carried out if necessary. Deprotection reaction of protecting groups is well known and can be carried out by following methods which may include, for example, (1) deprotection reaction by alkaline hydrolysis, (2) deprotection reaction under acidic conditions, (3) deprotection reaction by hydrolysis, (4) deprotection reaction of silyl groups, (5) deprotection reaction using a metal, (6) deprotection reaction using a metal complex and the like.

These methods are specifically described hereinbelow.

(1) Deprotection reaction by alkaline hydrolysis is carried out, for example, in an organic solvent (e.g. methanol, tetrahydrofuran and dioxane), by using an alkali metal hydroxide (e.g. sodium hydroxide, potassium hydroxide and lithium hydroxide), an alkaline earth metal hydroxide (e.g. barium hydroxide and calcium hydroxide) or a carbonate (e.g. sodium carbonate and potassium carbonate) or an aqueous solution thereof or a mixture thereof at 0 to 40° C.

(2) Deprotection reaction under acidic conditions is carried out, for example, in an organic solvent (e.g. dichloromethane, chloroform, dioxane, ethyl acetate, methanol, isopropyl alcohol, tetrahydrofuran and anisole) and in an organic acid (e.g. acetic acid, trifluoroacetic acid, methanesulphonic acid and p-tosylic acid) or an inorganic acid (e.g. hydrochloric acid and sulphuric acid) or a mixture thereof (e.g. hydrogen bromide/acetic acid) in the presence or absence of 2,2,2-trifluoroethanol at 0 to 100° C.

(3) Deprotection reaction by hydrolysis is carried out, for example, in a solvent (e.g. ethers (e.g. tetrahydrofuran, dioxane, dimethoxyethane and diethyl ether), alcohols (e.g. methanol and ethanol), benzenes (e.g. benzene and toluene), ketones (e.g. acetone and methyl ethyl ketone), nitriles (e.g.

acetonitrile), amides (e.g. N,N-dimethylformamide), water, ethyl acetate, acetic acid or mixed solvents of two or more of the above), in the presence of a catalyst (e.g. palladium-carbon, palladium black, palladium hydroxide-carbon, platinum oxide and Raney nickel), in a hydrogen atmosphere of normal or increased pressure or in the presence of ammonium formate at 0 to 200° C.

(4) Deprotection reaction of silyl groups is carried out, for example, in a water-miscible organic solvent (e.g. tetrahydrofuran and acetonitrile), by using tetrabutylammonium fluoride at 0 to 40° C. Alternatively, the reaction is carried out, for example, in an organic acid (e.g. acetic acid, trifluoroacetic acid, methanesulphonic acid and p-tosylic acid) or an inorganic acid (e.g. hydrochloric acid and sulphuric acid) or a mixture thereof (e.g. hydrogen bromide/acetic acid) at −10 to 100° C.

(5) Deprotection reaction using a metal is carried out, for example, in an acidic solvent (e.g. acetic acid, a buffer of pH 4.2 to 7.2 or a mixed solution thereof with an organic solvent such as tetrahydrofuran) in the presence of zinc powder with application of ultrasonic, if necessary, at 0 to 40° C.

(6) Deprotection reaction using a metal complex is carried out, for example, in an organic solvent (e.g. dichloromethane, N,N-dimethylformamide, tetrahydrofuran, ethyl acetate, acetonitrile, dioxane and ethanol), water or a mixed solvent thereof in the presence of a trap reagent (e.g. tributyltin hydride, triethylsilane, dimedone, morpholine, diethylamine and pyrrolidine), in the presence of an organic acid (e.g. acetic acid, formic acid and 2-ethylhexanoic acid) and/or a salt of an organic acid (e.g. sodium 2-ethylhexanoate and potassium 2-ethylhexanoate), in the presence or absence of a phosphine reagent (e.g. triphenylphosphine), with using a metal complex (e.g. tetrakis triphenylphosphine palladium (0), bis(triphenylphosphine)palladium (II) dichloride, palladium (II) acetate and tris(triphenylphosphine) rhodium (I) chloride) at 0 to 40° C.

Alternatively, the deprotection reaction can be carried out by the method described in, for example, T. W. Greene, Protective Groups in Organic Synthesis, Wiley, New York, 1999.

The protecting group of a hydroxy group may include, for example, a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

The protecting group of an amino group may include, for example, a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group and the like.

The protecting group of a hydroxy group and an amino group is not particularly limited to those mentioned above as far as it can be readily and selectively eliminated. For example, the ones described in T. W. Greene, Protective Groups in Organic Synthesis, Wiley, New York, 1999 may be used.

In the reactions described herein, the compounds used as starting materials such as the formulae (A), (II), (III), (IV) and (V) are well known or can be readily produced according to well-known methods.

In the reactions described herein, reactions accompanied by heating can be carried out, as apparent to a person skilled in the art, with a water bath, an oil bath, a sand bath or a microwave.

In the reactions described herein, a solid phase immobilized reagent which is immobilized on a high molecular polymer (e.g. polystyrene, polyacrylamide, polypropylene and polyethylene glycol) may be used.

In the reactions described herein, reaction products can be purified according to a conventional purification means such as distillation at normal or reduced pressure, high performance liquid chromatography using silica gel or magnesium silicate, thin layer chromatography, ion exchange resins, scavenger resins or column chromatography or washing and re-crystallization. Purification can be carried out after each reaction or after a few reactions.

[Toxicity]

The present compound has sufficiently low toxicity and thus can be used safely as a medicament.

[Application to Medicaments]

The present compound has $S1P_2$ antagonistic activity and thus is useful as a prophylactic and/or therapeutic agent for a $S1P_2$-mediated disease. The $S1P_2$-mediated disease may include a disease resulting from vascular constriction, fibrosis, a respiratory disease, arteriosclerosis, peripheral arterial occlusive disease, retinopathy, glaucoma, age-related macular degeneration, nephritis, diabetes, dyslipidemia, hepatitis, hepatic cirrhosis, hepatic failure, neuropathy, rheumatoid arthritis, wound, pain, urticaria, systemic lupus erythematosus (SLE), cancer and the like.

The disease resulting from vascular constriction as used herein may include cerebral vasospastic disease, cardiac vasospastic disease, coronary vasospastic disease, hypertension, pulmonary hypertension, myocardial infarction, angina, arrhythmia, portal hypertension, varix, ischemia-reperfusion injury and the like.

The fibrosis as used herein may include pulmonary fibrosis, hepatic fibrosis, kidney fibrosis, myocardial fibrosis, skin fibrosis and the like.

The respiratory disease as used herein may include bronchial asthma, acute lung injury, sepsis, chronic obstructive pulmonary disease and the like.

The present compound may be combined with another drug so as to be administered as a concomitant drug in order to:

1) complement and/or enhance the prophylactic and/or therapeutic effect of the present compound;
2) improve kinetics and uptake and reduce the dosage of the present compound; and/or
3) decrease side effect of the present compound.

The concomitant drug of the present compound and another drug may be administered as a combined agent containing both components in one formulation or administered separately. This separate administration includes simultaneous administration and sequential administration. The sequential administration may include the administration of the present compound prior to another drug and the administration of another drug prior to the present compound. The manners of administration of the components may be the same or different.

The concomitant drug may exhibit prophylactic and/or therapeutic effect for any diseases without limitation as far as the prophylactic and/or therapeutic effect of the present compound is complemented and/or enhanced.

Another drug which is used for complementation and/or enhancement of the prophylactic and/or therapeutic effect of the present compound for the disease resulting from vascular constriction may include, for example, calcium antagonists, thrombolytic agents, thromboxane synthase inhibitors, endothelin antagonists, antioxidants, radical scavengers, PARP inhibitors, astrocyte function improving agents, Rho kinase inhibitors, angiotensin II antagonists, angiotensin-converting enzyme inhibitors, diuretic agents, phosphodiesterase (PDE) 4 inhibitors, prostaglandins (hereinafter sometimes abbreviated as PG or PGs), aldosterone antagonists, endothelin antagonists, prostacyclin formulations, nitrates, β-blockers, vasodilators and the like.

Another drug which is used for complementation and/or enhancement of the prophylactic and/or therapeutic effect of the present compound for fibrosis may include, for example, steroids, immunosuppressants, TGF-β inhibitors, PDE5 inhibitors and the like.

Another drug which is used for complementation and/or enhancement of the prophylactic and/or therapeutic effect of the present compound for the respiratory disease may include, for example, PDE4 inhibitors, steroids, β-agonists, leukotriene receptor antagonists, thromboxane synthase inhibitors, thromboxane A2 receptor antagonists, mediator release suppressing agents, antihistamines, xanthine derivatives, anticholinergic agents, cytokine inhibitors, PGs, forskolin formulations, elastase inhibitors, metalloprotease inhibitors, expectorants, antibiotics and the like.

The calcium antagonists may include, for example, nifedipine, benidipine hydrochloride, diltiazem hydrochloride, verapamil hydrochloride, nisoldipine, nitrendipine, bepridil hydrochloride, amlodipine besylate, lomerizine hydrochloride, efonidipine hydrochloride and the like.

The thrombolytic agents may include, for example, alteplase, urokinase, tisokinase, nasaruplase, nateplase, tissue plasminogen activator, pamiteplase, monteplase and the like.

The thromboxane synthase inhibitors may include, for example, ozagrel hydrochloride, imitrodast sodium and the like. The radical scavengers may include, for example, Radicut and the like.

The PARP inhibitors may include, for example, 3-aminobenzamide, 1,3,7-trimethylxanthine, PD-141076, PD-141703 and the like.

The astrocyte function improving agents may include, for example, ONO-2506 and the like.

The Rho kinase inhibitors may include, for example, fasudil hydrochloride and the like.

The angiotensin II antagonists may include, for example, losartan, candesartan, valsartan, irbesartan, olmesartan, telmisartan and the like.

The angiotensin-converting enzyme inhibitors may include, for example, alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril and the like.

The diuretic agents may include, for example, mannitol, furosemide, acetazolamide, dichlorphenamide, methazolamide, trichlormethiazide, mefruside, spironolactone, aminophyline and the like.

The PDE4 inhibitors may include, for example, rolipram, cilomilast, Bay19-8004, NIK-616, roflumilast, cipamfylline, atizoram, SCH-351591, YM-976, V-11294A, PD-168787, ONO-6126, D-4396, IC-485 and the like.

The prostaglandins (PGs) may include, for example, PG receptor agonists, PG receptor antagonists and the like.

The PG receptor may include, for example, PGE receptors (EP1, EP2, EP3 and EP4), PGD receptors (DP and CRTH2), a PGF receptor (FP), a PGI receptor (IP), a thromboxane receptor (TP) and the like.

The aldosterone antagonists may include, for example, drospirenone, metyrapone, canrenoate potassium, canrenone, eplerenone, ZK-91587 and the like.

The prostacyclin formulations may include, for example, treprostinil sodium, epoprostenol sodium, beraprost sodium and the like.

The nitrates may include, for example, amyl nitrite, nitroglycerin, isosorbide dinitrate and the like.

The β-blockers may include, for example, alprenolol hydrochloride, bupranolol hydrochloride, bufetolol hydrochloride, oxprenolol hydrochloride, atenolol, bisoprolol fumarate, betaxolol hydrochloride, bevantolol hydrochloride, metoprolol tartrate, acebutolol hydrochloride, celiprolol hydrochloride, nipradilol, tilisolol hydrochloride, nadorol, propranolol hydrochloride, indenolol hydrochloride, carteolol hydrochloride, pindolol, bunitrolol hydrochloride, landiolol hydrochloride, esmolol hydrochloride, arotinolol hydrochloride, carvedilol, timolol maleate and the like.

The vasodilators may include, for example, diltiazem hydrochloride, trimetazidine hydrochloride, dipyridamole, etanofen hydrochloride, dilazep hydrochloride, trapidil, nicorandil and the like.

The steroids may include, as agents for oral administration or injection, for example cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone diacetate, triamcinolone acetonide, dexamethasone, dexamethasone acetate, dexamethasone sodium phosphate, dexamethasone palmitate, paramethasone acetate, betamethasone and the like. The steroids for inhalation may include, for example, beclomethasone propionate, fluticasone propionate, budesonide, flunisolide, triamcinolone, ST-126P, ciclesonide, dexamethasone palomithionate, mometasone furonate, prasterone sulphonate, deflazacort, methylprednisolone sleptanate, methylprednisolone sodium succinate and the like.

The immunosuppressants may include, for example, azathioprine, mizoribine, methotrexate, mycophenolate mofetil, cyclophosphamide, cyclosporine A, tacrolimus, sirolimus, everolimus, prednisolone, methylprednisolone, orthoclone OKT3, anti-human lymphocyte globulin, deoxyspergualin and the like.

The PDE5 inhibitors may include, for example, sildenafil, tadalafil, vardenafil, udenafil and the like.

The β agonists may include, for example, fenoterol hydrobromide, salbutamol sulphate, terbutaline sulphate, formoterol fumarate, salmeterol xinafoate, isoproterenol sulphate, orciprenaline sulphate, clorprenaline sulphate, epinephrine, trimetoquinol hydrochloride, hexoprenaline mesyl sulphate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319 and the like.

The leukotriene receptor antagonists may include, for example, pranlukast hydrate, montelukast, zafirlukast, seratrodast and the like.

The thromboxane A2 receptor antagonists may include, for example, seratrodast, ramatroban, domitroban calcium hydrate and the like.

The mediator release suppressing agents may include, for example, tranilast, cromolyn sodium, amlexanox, repirinast, ibudilast, tazanolast, pemirolast potassium and the like.

The antihistamines may include, for example, ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine and the like.

The xanthine derivatives may include, for example, aminophylline, theophylline, doxofylline, cipamfylline, diprophylline and the like.

The anticholinergic agents may include, for example, ipratropium bromide, oxytropium bromide, flutropium bromide, cimetropium bromide, temiverine, tiotropium bromide, revatropate and the like.

The cytokine inhibitors may include, for example, suplatast tosilate and the like.

The elastase inhibitors may include, for example, ONO-5046, ONO-6818, MR-889, PBI-1101, EPI-HNE-4, R-665 and the like.

The expectorants may include, for example, foeniculated ammonia spirit, sodium hydrogen carbonate, bromhexine hydrochloride, carbocysteine, ambroxol hydrochloride, ambroxol hydrochloride sustained release preparation, methylcysteine hydrochloride, acetylcysteine, L-ethylcysteine hydrochloride, tyloxapol and the like.

The antibiotics may include, for example, cefuroxime sodium, meropenem trihydrate, netilmicin sulphate, sisomicin sulphate, ceftibuten, PA-1806, IB-367, tobramycin, PA-1420, doxorubicin, astromicin sulphate, cefetamet pivoxil hydrochloride and the like. The antibiotics for inhalation may include, for example, PA-1806, IB-367, tobramycin, PA-1420, doxorubicin, astromicin sulphate, cefetamet pivoxil hydrochloride and the like.

The drug which is combined with the present compound encompasses not only the known compounds but also the compounds which will be found in future.

The present compound is usually administered systemically or locally in an oral or parenteral form. Oral formulations may include, for example, liquids for oral administration (e.g. elixirs, syrups, pharmaceutically acceptable solutions, suspensions and emulsions), solid agents for oral administration (e.g. tablets (including sublingual tablets and oral disintegration tablets), pills, capsules (including hard capsules, soft capsules, gelatine capsules and microcapsules), powders, granules and troches) and the like. Parenteral formulations may include, for example, liquids (e.g. injections (subcutaneous injections, intravenous injections, intramuscular injections, intraperitoneal injections, infusions and the like), ophthalmic solutions (e.g. aqueous ophthalmic solutions (aqueous ophthalmic solutions, aqueous ophthalmic suspensions, viscous ophthalmic solutions and solubilized ophthalmic solutions), non-aqueous ophthalmic solutions (non-aqueous ophthalmic solutions, non-aqueous ophthalmic suspensions and the like)) and the like), topical formulations (e.g. ointments (ophthalmic ointments and the like)), eardrops and the like. These formulations may be controlled-release preparations such as prompt release preparations or sustained release preparations. These formulations can be produced according to well-known methods such as the method described in Japanese Pharmacopoeia and the like.

The liquids for oral administration are produced by, for example, dissolving, suspending or emulsifying the active ingredient in a diluent that is generally used (e.g. purified water, ethanol and a mixture thereof). The liquids may further contain a wetting agent, a suspending agent, an emulsifying agent, a sweetening agent, a flavouring agent, an aroma, a preservative, a buffering agent and the like.

The solids for oral administration are formulated according to conventional methods by, for example, mixing the active ingredient with a vehicle (e.g. lactose, mannitol, glucose, microcrystalline cellulose and starch), a binder (e.g. hydroxypropyl cellulose, polyvinylpyrrolidone and magnesium aluminometasilicate), a disintegrant (e.g. calcium carboxymethyl cellulose), a lubricant (e.g. magnesium stearate), a stabiliser, a solution adjuvant (glutamic acid, aspartic acid and the like) and the like. The solids may be, if desired, coated with a coating agent (e.g. sucrose, gelatine, hydroxypropyl cellulose and hydroxypropyl methylcellulose phthalate) and may be coated with two or more layers.

The topical formulations as parenteral formulations are produced according to well-known methods or conventional formulations. For example, ointments are produced by triturating or melting the active ingredient in a base. The base for ointments is selected among those well-known or conventionally used. One or more selected from the followings, for example, may be used solely or in combination: a higher fatty acid or higher fatty acid ester (e.g. adipic acid, myristic acid, palmitic acid, stearic acid, oleic acid, adipate ester, myristate ester, palmitate ester, stearate ester and oleate ester), a wax (e.g. beeswax, whale wax and ceresin), a surfactant (e.g. polyoxyethylene alkyl ether phosphate esters), a higher alcohol (e.g. cetanol, stearyl alcohol and cetostearyl alcohol), a silicone oil (e.g. dimethylpolysiloxane), a hydrocarbon (e.g. hydrophilic petrolatum, white petrolatum, purified lanolin and liquid paraffin), a glycol (e.g. ethylene glycol, diethylene glycol, propylene glycol, polyethylene glycol and macrogol), vegetable oil (e.g. castor oil, olive oil, sesame oil and turpentine oil), animal oil (e.g. mink oil, egg-yolk oil, squalane and squalene), water, an absorption enhancing agent and a rash preventing agent. The formulations may further contain a humectant, a preservative, a stabilizer, an antioxidant, an aroma conferring agent and the like.

The injections as parenteral formulations encompass solutions, suspensions, emulsions and solid injections which are dissolved or suspended in a solvent upon use. The injections are used by, for example, dissolving, suspending or emulsifying the active ingredient in a solvent. The solvent used is, for example, distilled water for injections, saline, vegetable oil, propylene glycol, polyethylene glycol, alcohols such as ethanol or a combination thereof. The injections may further contain a stabilizer, a solution adjuvant (e.g. glutamic acid, aspartic acid and Polysolvate 80®), a suspending agent, an emulsifying agent, a soothing agent, a buffering agent, a preservative and the like. The injections are produced by sterilization at the final stage or through an aseptic manipulation. Alternatively, aseptic solid formulations, for example freeze-dried formulations, may be produced which may be dissolved, before use, in sterilized or aseptic distilled water for injection or another solvent.

For the purposes described above, the present compound or a concomitant agent of the present compound and another drug is generally administered systemically or locally in an oral or parenteral form. The dosage may vary according to the age, weight, symptoms, therapeutic effect, the manner of administration, treatment period and the like, and may be generally administered orally at a single dose for an adult of from 1 ng to 1000 mg with one or a few times daily, or administered parenterally at a single dose for an adult of from 0.1 ng to 10 mg with one or a few times daily, or continuously administered intravenously for 1 hour to 24 hours daily. The dosage may vary, as described above, according to various conditions, of course, and thus the dosage which is less than the range described above may be sufficient in some cases and the dosage which is more than the range described above may be required in some cases.

EXAMPLES

The present invention is hereinbelow described in detail by way of Examples which do not limit the present invention.

The solvents described in brackets in the sections of chromatography separation and TLC indicate the elution solvents or developing solvents used and the proportions are represented by volume ratios.

The solvents described in brackets in the sections of NMR indicate the solvents used for the measurements.

The compounds are denominated in the present specification by using a computer programme, ACD/Name® from Advanced Chemistry Development which generally denominates according to the rules from IUPAC, or according to the IUPAC nomenclature system.

Example 1: Methyl[4-(benzyloxy)phenyl]acetate

At room temperature, to a 3-L pear-shaped evaporating flask was added methyl(4-hydroxyphenyl)acetate (202 g) and potassium carbonate (233 g) which were dissolved in N,N-dimethylacetamide (DMA) (1 L). To the solution was added benzyl chloride (117 mL) at room temperature and stirred. The solution was then heated to 60° C. and stirred for 16 hours. The reaction solution was cooled to room temperature, diluted with methyl tert-butylether (MTBE) (1.3 L) and added with water (3 L) and an organic layer was extracted. The resulting organic layer was washed three times with a 1 N sodium hydroxide aqueous solution, then with water and a saturated sodium chloride solution and then dried over anhydrous magnesium sulphate. The solvent was distilled off at reduced pressure to give the titled compound (245 g) having the following physical properties.
TLC: Rf 0.68 (hexane:ethyl acetate=3:1);
$^1$H-NMR (CDCl$_3$): δ 3.56 (3H), 3.68 (3H), 5.05 (2H), 6.93 (3H), 7.19 (2H), 7.26-7.50 (5H).

Example 2: Methyl 2-[4-(benzyloxy)phenyl]-2-methylpropanoate

Under an argon atmosphere, to a 1-L four-neck flask was added the compound prepared in Example 1 (66.5 g) which was dissolved in tetrahydrofuran (THF) (260 mL). The solution was cooled to −10° C. and sequentially added with methyl iodide (8.1 mL) and a 1.53 M solution of potassium tert-butoxide (85 mL) in THF while the internal temperature of the reaction solution was maintained at −10° C. to −7.5° C. This procedure was repeated eight times. The solution was then stirred at −10° C. for 10 minutes and slowly added dropwise with acetic acid (50.5 mL). The solution was neutralized with a 2 N sodium hydroxide aqueous solution and saturated aqueous sodium bicarbonate and extracted with ethyl acetate and hexane. The extract was washed with water and a saturated sodium chloride solution and then dried over anhydrous magnesium sulphate. The solvent was then distilled off under reduced pressure. Activated carbon (4 g) was then added thereto, the mixture was stirred at room temperature for 30 minutes, the activated carbon was filtered off, and the solvent was distilled off under reduced pressure to give the titled compound (73.0 g) having the following physical properties.
TLC: Rf 0.54 (hexane:ethyl acetate=5:1);
$^1$H-NMR (CDCl$_3$): δ 1.55 (6H), 3.64 (3H), 5.05 (2H), 6.93 (2H), 7.26 (2H), 7.30-7.48 (5H).

Example 3: Methyl 2-(4-hydroxyphenyl)-2-methylpropanoate

Under an argon atmosphere, to a 2-L pear-shaped evaporating flask was added a solution of the compound prepared in Example 2 (72.0 g) in methanol (420 mL) mixed with ethyl acetate (150 mL). After purged with argon, 20% palladium carbon (7.60 g) was added. The flask was degassed and charged with hydrogen gas. The flask was vigorously stirred at room temperature for 4 hours. The reaction system was purged with argon, filtered with celite and washed with ethyl acetate. The filtrate was subjected to distillation under reduced pressure followed by dilution with ethyl acetate (150 mL) and hexane (50 mL). The diluted solution was dried over anhydrous magnesium sulphate and the solvent was distilled off to obtain a gray-white solid (50 g). The solid was dissolved in ethyl acetate (70 mL) while heating which was then added with hexane (700 mL) and stirred at room temperature. The precipitated solid was collected by filtration, washed with hexane/ethyl acetate (10:1) and dried to give the titled compound (41.1 g) having the following physical properties.
TLC: Rf 0.27 (hexane:ethyl acetate=5:1);
$^1$H-NMR (CDCl$_3$): δ 1.55 (6H), 3.65 (3H), 6.77 (2H), 7.19 (2H)

Example 4: Methyl 2-[4-(3-fluoro-5-nitrophenoxy)phenyl]-2-methylpropanoate

Under an argon atmosphere and at room temperature, to a 500-mL pear-shaped evaporating flask were added the compound prepared in Example 3 (41.1 g) and potassium phosphate (81.5 g). To the reaction system was added 1,3-difluoro-5-nitrobenzene (30.6 g) dissolved in DMA (128 mL) and stirred. The reaction system was then heated to 70° C. and stirred for 6.5 hours. The reaction solution was cooled to room temperature, diluted with MTBE (150 mL) and added with ice water (150 mL) before stirring. An organic layer was extracted by adding MTBE and water. The aqueous layer was added with MTBE and water to extract an organic layer. The organic layer was combined, washed twice with a 1 N sodium hydroxide aqueous solution and then with a saturated sodium chloride solution and dried over anhydrous magnesium sulphate, and the solvent was distilled off under reduced pressure. The titled compound (66.0 g) having the following physical properties was obtained.
TLC: Rf 0.68 (hexane:ethyl acetate=3:1);
$^1$H-NMR (CDCl$_3$): δ 1.62 (6H), 3.69 (3H), 6.91 (2H), 6.96-7.08 (4H), 7.40 (2H), 7.65 (1H).

Example 5: Methyl 2-{4-[3-(4-fluorophenoxy)-5-nitrophenoxy]phenyl}-2-methylpropanoate Under an argon atmosphere and at room temperature, to a 500-mL pear-shaped evaporating flask were added the compound prepared in Example 4 (64 g), 4-fluorophenol (40 g) and potassium phosphate (102 g) which were dissolved in DMA (130 mL) before stirring. The solution was then heated to 100° C. and stirred for 10 hours. The reaction solution was cooled to room temperature, diluted with MTBE (200 mL) and added with ice water (400 mL) before stirring. The reaction solution was further washed with MTBE, a 1 N sodium hydroxide aqueous solution and water. An aqueous layer was extracted twice with MTBE. The organic layer was combined, washed twice with a 1 N sodium hydroxide aqueous solution and then with water and a saturated sodium chloride solution and dried over anhydrous magnesium sulphate, and the solvent was distilled off under reduced pressure. The obtained residue was added with ethanol (104 mL), heated and dissolved. To the solution was gradually added hexane (520 mL) and stirred at room temperature to allow precipitation of solids. The precipitate was collected by filtration with a Kiriyama funnel (#5B-φ95) and washed with hexane/ethanol (10:1) and the obtained residue was dried under reduced pressure at 50° C. The titled compound (54.8 g) having the following physical properties was obtained.

TLC: Rf 0.57 (hexane:ethyl acetate=5:1);
$^1$H-NMR (CDCl$_3$): δ 1.60 (6H), 3.68 (3H), 6.91 (1H), 6.91 (1H), 6.98-7.14 (4H), 7.36 (1H), 7.39 (1H), 7.40 (1H), 7.46 (1H).

Example 6: Methyl 2-{4-[3-amino-5-(4-fluorophenoxy)phenoxy]phenyl}-2-methylpropanoate Under an argon atmosphere, to a 500-mL pear-shaped evaporating flask was added the compound prepared in Example 5 (53.6 g) to which a mixed solution of methanol (50 mL) and ethyl acetate (175 mL) was added. The mixture was heated until dissolution, and the flask was purged with argon prior to addition of 5% palladium carbon (10.8 g). The flask was degassed and charged with hydrogen gas. The flask was vigorously stirred at room temperature for 3 hours. The reaction system was purged with argon, filtered with celite and washed with ethyl acetate. The obtained filtrate was subjected to distillation under reduced pressure to give the titled compound (43.9 g) having the following physical properties.

TLC: Rf 0.13 (hexane:ethyl acetate=5:1);
$^1$H-NMR (CDCl$_3$): δ 1.57 (6H), 3.66 (3H), 3.69 (NH, 2H), 5.97 (1H), 6.02 (2H), 6.96 (2H), 6.99 (2H), 7.01 (2H), 7.28 (2H).

Example 7: Methyl 2-{4-[3-(4-fluorophenoxy)-5-{[(2,2,2-trichloroethoxy)carbonyl]amino}phenoxy]phenyl}-2-methylpropanoate Under an argon atmosphere and at room temperature, to a 500-mL pear-shaped evaporating flask were added the compound prepared in Example 6 (43.9 g) and sodium hydrogen carbonate (18.6 g) which were dissolved in ethyl acetate (111 mL). The solution was cooled to 0° C. and 2,2,2-trichloroethyl chloroformate (15.7 mL) was gradually added dropwise over 15 minutes so that the internal temperature did not exceed 10° C. The solution was then stirred at room temperature for 60 minutes. After elimination of 2,2,2-trichloroethyl chloroformate was confirmed by thin layer chromatography, the reaction solution was added with water and stirred. The solid was precipitated by addition of hexane. The precipitate was collected by filtration with a Kiriyama funnel (#5B-φ95) and washed with water and hexane/ethyl acetate (3:1) and the obtained residue was dried under reduced pressure at 50° C. The titled compound (58.5 g) having the following physical properties was obtained.

TLC: Rf 0.45 (hexane:ethyl acetate=5:1);
$^1$H-NMR (CDCl$_3$): δ 1.58 (6H), 3.66 (3H), 4.77 (2H), 6.36 (1H), 6.73 (1H), 6.78 (br, 1H), 6.82 (br, 1H), 6.93-7.10 (6H), 7.31 (2H).

Example 8: Methyl 2-{4-[3-(4-fluorophenoxy)-5-{[(4-hydroxy-4-isobutyl-1-piperidinyl)carbonyl]amino}phenoxy]phenyl}-2-methylpropanoate Under an argon atmosphere and at room temperature, in a 500 mL pear-shaped evaporating flask, the compound prepared in Example 7 (26.6 g) was dissolved in DMA (31 mL), added with 4-isobutyl-4-piperidinol (9.53 g) and stirred. The solution was then heated to 90° C. and stirred for 2 hours. The solution was further added with 4-isobutyl-4-piperidinol (1.45 g) and diisopropylethylamine (818 µL) and stirred for 2 hours. The reaction solution was allowed to cool to room temperature, diluted with MTBE, and added with ice water to extract an organic layer. The obtained aqueous layer was extracted with MTBE. The organic layer was combined, washed twice with a 1 N hydrochloric acid aqueous solution, three times with a 1 N sodium hydroxide aqueous solution, with water and with a saturated sodium chloride solution and dried over anhydrous sodium sulphate and the solvent was distilled off under reduced pressure. The titled compound (24.8 g) having the following physical properties was obtained.

TLC: Rf 0.46 (hexane:ethyl acetate=1:1);
$^1$H-NMR (CDCl$_3$): δ 0.97 (6H), 1.05 (1H), 1.41 (2H), 1.50-1.70 (10H), 1.75-1.90 (1H), 3.20-3.35 (2H), 3.66 (3H), 3.70-3.80 (2H), 6.25-6.35 (2H), 6.71 (1H), 6.81 (1H), 6.90-7.05 (6H), 7.29 (2H).

Example 9: 2-{4-[3-(4-fluorophenoxy)-5-{[(4-hydroxy-4-isobutyl-1-piperidinyl)carbonyl]amino}phenoxy]phenyl}-2-methylpropanoic Acid

[C 13]

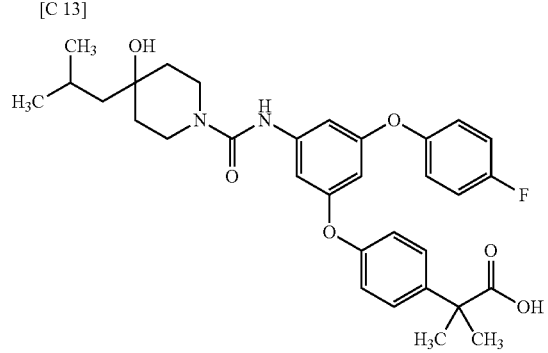

At room temperature, in a 1 L pear-shaped evaporating flask, the compound prepared in Example 8 (24.8 g) was dissolved in a mixed solution of methanol (150 mL) and THF (150 mL) and the solution was stirred. The solution was then heated to 45° C., gradually added with a 1 N sodium hydroxide aqueous solution (107 mL) and stirred overnight at 45° C. The solution was added with a 2 N sodium hydroxide aqueous solution (20 mL). After stirring for 1 hour, the solvent was distilled off under reduced pressure and the solution was further stirred for 1.5 hours at 45° C.

A 2 N sodium hydroxide aqueous solution (12 mL) was further added and the solution was stirred for 45 minutes at 55° C. The solution was cooled to 0° C. and added with ice and a 5 N hydrochloric acid aqueous solution until the reaction system was acidic (pH=2). The reaction system was diluted with ethyl acetate and extracted. An organic layer was further washed with a saturated sodium chloride solution and then dried over anhydrous magnesium sulphate and the solvent was distilled off under reduced pressure. The residue was purified by silica gel chromatography (hexane:ethyl acetate=65:35→44:56→30:70) to give the titled compound (20 g) having the following physical properties.

TLC: Rf 0.53 (dichloromethane:methanol=10:1);
$^1$H-NMR (CDCl$_3$) δ 7.28-7.33 (m, 2H), 6.94-7.01 (m, 4H), 6.89-6.93 (m, 2H), 6.80 (t, 1H), 6.61 (t, 1H), 6.25 (t, 1H), 3.60-3.73 (m, 2H), 3.12-3.25 (m, 2H), 1.71-1.85 (m, 1H), 1.46-1.59 (m, 10H), 1.34 (d, 2H), 0.92 (d, 6H).

Examples 9(1) to 9(64)

The compounds of the following Examples were obtained by carrying out the processes with the same purposes as Example 4→Example 5→Example 6→Example 7→Example 8→Example 9 using 1,3-difluoro-5-nitrobenzene; the compound prepared in Example 3 or a corresponding phenol derivative thereof; 4-fluorophenol or a corresponding phenol derivative thereof; 2,2,2-trichloroethyl chloroformate; and 4-isobutyl-4-piperidinol or a corresponding piperidine derivative thereof.

Example 9(1): 4-[3-({[4-(2-ethylbutyl)-4-hydroxy-1-piperidinyl]carbonyl}amino)-5-(4-fluorophenoxy)phenoxy]benzoic Acid

[C 14]

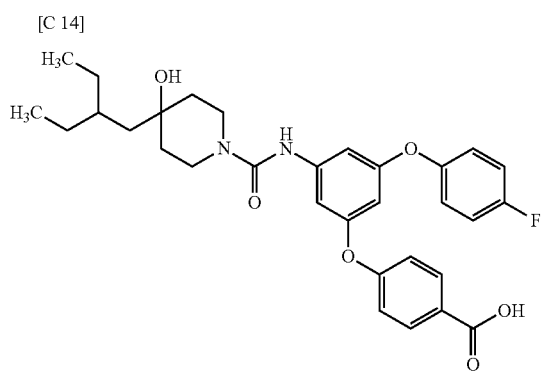

TLC: Rf 0.28 (dichloromethane:methanol=10:1);
$^1$H-NMR (CD$_3$OD): δ 8.01 (d, 2H) 7.18-6.99 (m, 6H) 6.94-6.87 (m, 2H) 6.29 (t, 1H) 3.90-3.75 (m, 2H) 3.28-3.15 (m, 2H) 1.63-1.47 (m, 4H) 1.45-1.26 (m, 7H) 0.87 (t, 6H).

Example 9(2): 4-[3-({[4-(4-bromophenyl)-4-hydroxy-1-piperidinyl]carbonyl}amino)-5-(4-fluorophenoxy)phenoxy]benzoic Acid TLC: Rf 0.38 (dichloromethane:methanol=10:1);
$^1$H-NMR (DMSO-d$_6$): δ 8.63 (s, 1H), 7.95 (d, 2H), 7.48 (d, 2H), 7.41 (d, 2H), 7.24 (t, 2H), 7.15-7.07 (m, 5H), 7.02 (dd, 1H), 6.31 (dd, 1H), 5.18 (s, 1H), 3.98-3.94 (m, 2H), 3.17-3.10 (m, 2H), 1.83-1.76 (m, 2H), 1.57-1.53 (m, 2H).

Example 9(3): 4-[3-(4-fluorophenoxy)-5-({[4-(4-fluorophenyl)-4-hydroxy-1-piperidinyl]carbonyl}amino)phenoxy]benzoic Acid

[C 15]

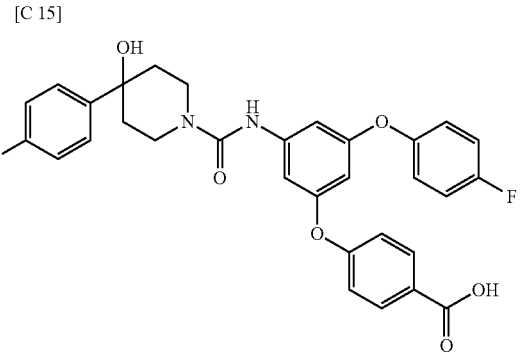

TLC: Rf 0.38 (dichloromethane:methanol=10:1);
$^1$H-NMR (DMSO-d$_6$): δ 8.63 (s, 1H), 7.95 (d, 2H), 7.48 (dd, 2H), 7.24 (t, 2H), 7.15-7.07 (m, 7H), 7.02 (dd, 1H), 6.31 (dd, 1H), 5.13 (s, 1H), 3.98-3.93 (m, 2H), 3.18-3.10 (m, 2H), 1.84-1.77 (m, 2H), 1.59-1.54 (m, 2H).

Example 9(4): 4-[3-(4-chlorophenoxy)-5-({[4-(2-ethylbutyl)-4-hydroxy-1-piperidinyl]carbonyl}amino)phenoxy]benzoic Acid TLC: Rf 0.33 (dichloromethane:methanol=10:1);
$^1$H-NMR (CD$_3$OD): δ 8.48 (s, 1H), 8.02 (d, 2H), 7.36 (d, 2H), 7.00-7.12 (m, 4H), 6.95 (t, 2H), 6.34 (t, 1H), 3.83 (d, 2H), 3.14-3.29 (m, 2H), 1.28-1.68 (m, 11H), 0.87 (t, 6H).

Example 9(5): 4-[3-({[4-(2-ethylbutyl)-4-hydroxy-1-piperidinyl]carbonyl}amino)-5-(4-methoxyphenoxy)phenoxy]benzoic Acid TLC: Rf 0.33 (dichloromethane:methanol=10:1);
$^1$H-NMR (CD$_3$OD): δ 8.43 (s, 1H), 7.97-8.04 (m, 2H), 7.04 (d, 2H), 6.90-7.02 (m, 4H), 6.86-6.89 (m, 1H), 6.85 (t, 1H), 6.15-6.29 (m, 1H), 3.78-3.85 (m, 5H), 3.13-3.28 (m, 2H), 1.49-1.71 (m, 4H), 1.23-1.44 (m, 7H), 0.87 (t, 6H).

Example 9(6): 4-[3-(3,4-difluorophenoxy)-5-({[4-(2-ethylbutyl)-4-hydroxy-1-piperidinyl]carbonyl}amino)phenoxy]benzoic Acid TLC: Rf 0.37 (dichloromethane:methanol=9:1);
$^1$H-NMR (CDCl$_3$): δ 8.03 (d, 2H), 7.06-7.18 (m, 1H), 7.03 (d, 2H), 6.84-6.93 (m, 3H), 6.73-6.81 (m, 1H), 6.53 (br. s., 1H), 6.37-6.41 (m, 1H), 3.73-3.83 (m, 2H), 3.22-3.34 (m, 2H), 1.55-1.65 (m, 5H), 1.28-1.42 (m, 7H), 0.79-0.90 (m, 6H).

Example 9(7): 4-[3-({[4-(2-ethylbutyl)-4-hydroxy-1-piperidinyl]carbonyl}amino)-5-(4-methylphenoxy)phenoxy]benzoic Acid TLC: Rf 0.24 (dichloromethane:methanol=1:2);
$^1$H-NMR (CDCl$_3$): δ 8.02 (d, 2H), 7.14 (d, 2H), 7.02 (d, 2H), 6.97-6.91 (m, 3H), 6.72 (t, 1H), 6.42-6.31 (m, 2H), 3.84-3.73 (m, 2H), 3.37-3.14 (m, 2H), 2.33 (s, 3H), 1.75-1.50 (m, 5H), 1.44-1.28 (m, 8H), 0.85 (t, 6H).

Example 9(8): 4-{3-({[4-(2-ethylbutyl)-4-hydroxy-1-piperidinyl]carbonyl}amino)-5-[4-(trifluoromethyl)phenoxy]phenoxy}benzoic Acid TLC: Rf 0.26 (dichloromethane:methanol=10:1);
$^1$H-NMR (CDCl$_3$): δ 8.09-7.97 (m, 2H), 7.58 (d, 2H), 7.09 (d, 2H), 7.07-7.01 (m, 2H), 6.97 (t, 1H), 6.92 (t, 1H), 6.48 (s, 1H), 6.45 (t, 1H), 3.85-3.73 (m, 2H), 3.39-3.17 (m, 2H), 1.65-1.51 (m, 4H), 1.45-1.26 (m, 9H), 0.84 (t, 6H).

Example 9(9): 2-chloro-4-[3-({[4-(2-ethylbutyl)-4-hydroxy-1-piperidinyl]carbonyl}amino)-5-(4-fluorophenoxy)phenoxy]benzoic Acid TLC: Rf 0.33 (chloroform:methanol=5:1);
$^1$H-NMR (CD$_3$OD): δ 7.60 (d, 1H), 7.08-6.80 (m, 8H), 6.25 (t, 1H), 3.83 (m, 2H), 3.22 (m, 2H), 1.66-1.30 (m, 11H), 0.86 (t, 6H).

Example 9(10): 4-[3-(cyclohexyloxy)-5-({[4-(2-ethylbutyl)-4-hydroxy-1-piperidinyl]carbonyl}amino)phenoxy]benzoic Acid TLC: Rf 0.38 (dichloromethane:methanol=10:1);
$^1$H-NMR (CDCl$_3$): δ 7.97-8.05 (m, 2H), 6.97-7.05 (m, 2H), 6.87 (t, 1H), 6.66 (t, 1H), 6.38 (s, 1H), 6.31 (t, 1H), 4.18-4.25 (m, 1H), 3.79 (d, 2H), 3.23-3.35 (m, 2H), 1.84-2.00 (m, 2H), 1.69-1.84 (m, 2H), 1.46-1.65 (m, 6H), 1.22-1.45 (m, 11H), 0.85 (t, 6H).

Example 9(11): 4-[3-(2-chlorophenoxy)-5-({[4-(2-ethylbutyl)-4-hydroxy-1-piperidinyl]carbonyl}amino)phenoxy]benzoic Acid TLC: Rf 0.25 (dichloromethane:methanol=10:1);
$^1$H-NMR (CDCl$_3$): δ 8.07-7.95 (m, 2H), 7.44 (dd, 1H), 7.30-7.20 (m, 1H), 7.15-7.05 (m, 2H), 7.05-6.99 (m, 2H), 6.96 (t, 1H), 6.75 (t, 1H), 6.45 (s, 1H), 6.34 (t, 1H), 3.85-3.72 (m, 2H), 3.38-3.14 (m, 2H), 1.65-1.57 (m, 4H), 1.45-1.24 (m, 8H), 0.84 (t, 6H).

Example 9(12): 4-[3-(3-chlorophenoxy)-5-({[4-(2-ethylbutyl)-4-hydroxy-1-piperidinyl]carbonyl}amino)phenoxy]benzoic Acid TLC: Rf 0.24 (dichloromethane:methanol=10:1);
$^1$H-NMR (CDCl$_3$): δ 8.11-7.96 (m, 2H), 7.31-7.20 (m, 1H), 7.11-7.02 (m, 4H), 6.99 (t, 1H), 6.96-6.89 (m, 1H), 6.83 (t, 1H), 6.43 (s, 1H), 6.41 (t, 1H), 3.86-3.74 (m, 2H), 3.39-3.14 (m, 2H), 1.75-1.50 (m, 6H), 1.44-1.25 (m, 7H), 0.85 (t, 6H).

Example 9(13): {4-[3-({[4-(2-ethylbutyl)-4-hydroxy-1-piperidinyl]carbonyl}amino)-5-(4-fluorophenoxy) phenoxy]phenyl}acetic Acid TLC: Rf 0.36 (dichloromethane:methanol=10:1);
$^1$H-NMR (CDCl$_3$): δ 7.24 (d, 2H), 7.03-6.96 (m, 6H), 6.81 (dd, 1H), 6.65 (dd, 1H), 6.40 (brs, 1H), 6.31 (dd, 1H), 3.76-3.72 (m, 2H), 3.62 (s, 2H), 3.28-3.20 (m, 2H), 1.60-1.58 (m, 4H), 1.39-1.33 (m, 8H), 0.84 (t, 6H).

Example 9(14): 4-[3-(2,4-difluorophenoxy)-5-({[4-(2-ethylbutyl)-4-hydroxy-1-piperidinyl]carbonyl}amino)phenoxy]benzoic Acid TLC: Rf 0.29 (dichloromethane:methanol=10:1);
$^1$H-NMR (CDCl$_3$): δ 8.01 (d, 2H), 7.19-7.06 (m, 1H), 7.06-6.69 (m, 6H), 6.51 (br. s., 1H), 6.33 (t, 1H), 3.85-3.65 (m, 2H), 3.35-3.11 (m, 2H), 1.67-1.50 (m, 4H), 1.43-1.18 (m, 8H), 0.84 (t, 6H).

Example 9(15): 4-[3-({[4-(2-ethylbutyl)-4-hydroxy-1-piperidinyl]carbonyl}amino)-5-(4-fluorophenoxy)phenoxy]-2-hydroxybenzoic Acid TLC: Rf 0.16 (dichloromethane:methanol:ethanol=100:10:1);
$^1$H-NMR (CDCl$_3$): δ 7.48-7.62 (m, 1H), 6.91-7.10 (m, 5H), 6.77-6.87 (m, 1H), 6.67 (t, 1H), 6.57 (br. s., 1H), 6.25 (br. s., 1H), 3.55-3.83 (m, 2H), 3.03-3.30 (m, 2H), 1.41-1.57 (m, 4H), 1.21-1.40 (m, 7H), 0.81 (t, 6H).

Example 9(16): 4-[3-({[4-(2-ethylbutyl)-4-hydroxy-1-piperidinyl]carbonyl}amino)-5-(4-fluorophenoxy)phenoxy]-3-fluorobenzoic Acid TLC: Rf 0.48 (dichloromethane:methanol=8:2);
$^1$H-NMR (CD$_3$OD): δ 8.46 (s, 1H), 7.77-7.86 (m, 2H), 7.00-7.20 (m, 5H), 6.83-6.91 (m, 2H), 6.25-6.30 (m, 1H), 3.82 (d, 2H), 3.14-3.28 (m, 2H), 1.20-1.67 (m, 11H), 0.86 (t, 6H).

Example 9(17): {4-[3-({[4-(2-ethylbutyl)-4-hydroxy-1-piperidinyl]carbonyl}amino)-5-(4-fluorophenoxy)phenoxy]-2-fluorophenyl}acetic Acid TLC: Rf 0.19 (chloroform:methanol=19:1);
$^1$H-NMR (CDCl$_3$): δ 6.54-7.20 (m, 10H), 6.30 (s, 1H), 3.71 (br. s., 2H), 3.56 (br. s., 2H), 3.19 (br. s., 2H), 1.13-1.47 (m, 13H), 0.64-0.93 (m, 6H).

Example 9(18): 4-[3-(4-fluorophenoxy)-5-{[(4-hydroxy-4-isobutyl-1-piperidinyl)carbonyl]amino}phenoxy]benzoic Acid TLC: Rf 0.22 (dichloromethane:methanol=9:1);
$^1$H-NMR (CD$_3$OD): δ 7.95-8.05 (m, 2H), 6.99-7.16 (m, 6H), 6.89-6.90 (m, 2H), 6.27 (dd, 1H), 3.77-3.82 (m, 2H), 3.18-3.28 (m, 2H), 1.76-1.93 (m, 1H), 1.46-1.65 (m, 4H), 1.38 (d, 2H), 0.96 (d, 6H).

Example 9(19): 4-[3-({[4-(2-ethylbutyl)-4-hydroxy-1-piperidinyl]carbonyl}amino)-5-(4-fluorobenzoyl)phenoxy]benzoic Acid TLC: Rf 0.25 (dichloromethane:methanol=10:1);
$^1$H-NMR (CDCl$_3$): δ 7.88-7.96 (m, 2H), 7.71-7.80 (m, 2H), 7.40-7.47 (m, 2H), 7.02-7.11 (m, 2H), 6.90-6.97 (m, 3H), 3.69-3.73 (m, 2H), 3.11-3.20 (m, 2H), 1.45-1.54 (m, 4H), 1.19-1.33 (m, 7H), 0.75 (t, 6H).

Example 9(20): 2-{4-[3-({[4-(2-ethylbutyl)-4-hydroxy-1-piperidinyl]carbonyl}amino)-5-(4-fluorophenoxy)phenoxy]phenyl}-2-methylpropanoic Acid TLC: Rf 0.39 (dichloromethane:methanol=10:1);
$^1$H-NMR (CDCl$_3$): δ 7.33 (d, 2H), 6.92-7.05 (m, 6H), 6.77-6.78 (m, 1H), 6.65-6.68 (m, 1H), 6.44 (s, 1H), 6.24-

6.32 (m, 1H), 3.70-3.77 (m, 2H), 3.14-3.31 (m, 2H), 1.52-1.65 (m, 10H), 1.29-1.42 (m, 7H), 0.84 (t, 6H).

Example 9(21): 2-chloro-4-[3-(4-fluorophenoxy)-5-{[(4-hydroxy-4-isobutyl-1-piperidinyl)carbonyl]amino}phenoxy]benzoic Acid TLC: Rf 0.30 (chloroform:methanol=5:1);
$^1$H-NMR (CDCl$_3$+CD$_3$OD): δ 7.69 (d, 1H), 7.20-6.84 (m, 9H), 6.26 (t, 1H), 3.80 (m, 2H), 3.23 (m, 2H), 1.87 (m, 1H), 1.66-1.48 (m, 4H), 1.37 (d, 2H), 0.95 (d, 6H).

Example 9(22): 4-[3-({[4-(2-ethylbutyl)-4-hydroxy-1-piperidinyl]carbonyl}amino)-5-(4-fluorophenoxy)phenoxy]-2-methylbenzoic Acid TLC: Rf 0.33 (dichloromethane:methanol=10:1);
$^1$H-NMR (CDCl$_3$): δ 7.81 (d, 1H), 6.96-7.05 (m, 4H), 6.67-6.82 (m, 4H), 6.29 (t, 1H), 3.66-3.76 (m, 2H), 3.14-3.25 (m, 2H), 2.46 (s, 3H), 1.49-1.62 (m, 4H), 1.23-1.39 (m, 7H), 0.82 (t, 6H).

Example 9(23): 4-[3-(4-fluorophenoxy)-5-{[(4-hydroxy-4-isobutyl-1-piperidinyl)carbonyl]amino}phenoxy]-2-methylbenzoic Acid TLC: Rf 0.70 (chloroform:methanol=5:1);
$^1$H-NMR (CDCl$_3$+CD$_3$OD): δ 7.81 (d, 1H), 7.18-6.78 (m, 8H), 6.24 (t, 1H), 3.80 (m, 2H), 3.23 (m, 2H), 2.52 (s, 3H), 1.84 (m, 1H), 1.68-1.48 (m, 4H), 1.40 (d, 2H), 0.95 (d, 6H).

Example 9(24): 3-fluoro-4-[3-(4-fluorophenoxy)-5-{[(4-hydroxy-4-isobutyl-1-piperidinyl)carbonyl]amino}phenoxy]benzoic Acid TLC: Rf 0.20 (dichloromethane:methanol=9:1);
$^1$H-NMR (CD$_3$OD): δ 7.68-7.77 (m, 2H), 6.98-7.12 (m, 5H), 6.90 (dd, 1H), 6.73 (dd, 1H), 6.21 (dd, 1H), 3.76-3.80 (m, 2H), 3.15-3.28 (m, 2H), 1.83-1.93 (m, 1H), 1.43-1.69 (m, 4H), 1.37 (d, 2H), 0.96 (d, 6H).

Example 9(25): 4-[3-(4-fluorophenoxy)-5-{[(4-hydroxy-4-isobutyl-1-piperidinyl)carbonyl]amino}phenoxy]-2-methoxybenzoic Acid TLC: Rf 0.47 (dichloromethane:methanol=9:1);
$^1$H-NMR (CD$_3$OD): δ 7.87 (d, 1H), 7.03-7.13 (m, 4H), 6.88-6.94 (m, 2H), 6.76 (d, 1H), 6.58 (dd, 1H), 6.30 (dd, 1H), 3.85 (s, 1H), 3.76-3.86 (m, 2H), 3.19-3.28 (m, 2H), 1.81-1.90 (m, 1H), 1.48-1.64 (m, 4H), 1.38 (d, 2H), 0.96 (d, 6H).

Example 9(26): 2-{4-[3-(4-fluorophenoxy)-5-{[(4-hydroxy-4-isobutyl-1-piperidinyl)carbonyl]amino}phenoxy]phenyl}propanoic Acid TLC: Rf 0.31 (dichloromethane:methanol=10:1);
$^1$H-NMR (CDCl$_3$): δ 7.24 (d, 2H), 6.96-7.05 (m, 4H), 6.92 (d, 2H), 6.82 (t, 2H), 6.60-6.66 (m, 1H), 6.27 (t, 1H), 3.54-3.75 (m, 3H), 3.11-3.26 (m, 2H), 1.70-1.88 (m, 1H), 1.48-1.60 (m, 4H), 1.44 (d, 3H), 1.36 (d, 2H), 0.94 (d, 6H).

Example 9(27): {2-fluoro-4-[3-(4-fluorophenoxy)-5-{[(4-hydroxy-4-isobutyl-1-piperidinyl)carbonyl]amino}phenoxy]phenyl}acetic Acid TLC: Rf 0.17 (dichloromethane:methanol=10:1);
$^1$H-NMR (CDCl$_3$): δ 7.10 (t, 1H), 6.93-7.02 (m, 4H), 6.87 (s, 1H), 6.59-6.73 (m, 3H), 6.27 (s, 1H), 3.61-3.75 (m, 2H), 3.47 (br. s., 2H), 3.08-3.26 (m, 2H), 1.77 (dquin, 1H), 1.38-1.59 (m, 4H), 1.32 (d, 2H), 0.91 (d, 6H).

Example 9(28): {4-[3-(4-fluorophenoxy)-5-{[(4-hydroxy-4-isobutyl-1-piperidinyl)carbonyl]amino}phenoxy]phenyl}acetic Acid TLC: Rf 0.17 (dichloromethane:methanol=10:1);
$^1$H-NMR (CD$_3$OD): δ 8.38 (s, 1H), 7.27 (d, 2H), 7.01-7.12 (m, 4H), 6.94-7.00 (m, 2H), 6.81 (dq, 2H), 6.21 (t, 1H), 3.75-3.84 (m, 2H), 3.59 (s, 2H), 3.16-3.29 (m, 2H), 1.77-1.93 (m, 1H), 1.45-1.64 (m, 4H), 1.38 (d, 2H), 0.97 (d, 6H).

Example 9(29): 2-fluoro-4-[3-(4-fluorophenoxy)-5-({[4-(4-fluorophenyl)-4-hydroxy-1-piperidinyl]carbonyl}amino)phenoxy]benzoic Acid TLC: Rf 0.34 (chloroform:methanol=4:1);
$^1$H-NMR (CD$_3$OD): δ 7.91 (t, 1H), 7.53-7.47 (m, 2H), 7.16-6.95 (m, 8H), 6.88-6.76 (m, 2H), 6.33 (t, 1H), 4.08-3.97 (m, 2H), 3.40-3.30 (m, 2H), 2.07-1.94 (m, 2H), 1.77-1.67 (m, 2H).

Example 9(30): {2-fluoro-4-[3-(4-fluorophenoxy)-5-({[4-(4-fluorophenyl)-4-hydroxy-1-piperidinyl]carbonyl}amino)phenoxy]phenyl}acetic Acid TLC: Rf 0.41 (chloroform:methanol=4:1);
$^1$H-NMR (CD$_3$OD): δ 7.53-7.46 (m, 2H), 7.28 (t, 1H), 7.15-7.00 (m, 6H), 6.91-6.87 (m, 2H), 6.83-6.76 (m, 2H), 6.28 (t, 1H), 4.06-3.97 (m, 2H), 3.63 (s, 2H), 3.38-3.30 (m, 2H), 2.06-1.93 (m, 2H), 1.77-1.68 (m, 2H).

Example 9(31): 2-{4-[3-(4-fluorophenoxy)-5-({[4-(4-fluorophenyl)-4-hydroxy-1-piperidinyl]carbonyl}amino)phenoxy]phenyl}propanoic Acid TLC: Rf 0.32 (chloroform:methanol=9:1);
$^1$H-NMR (CD$_3$OD): δ 7.41-7.56 (m, 2H), 7.24-7.36 (m, 2H), 6.91-7.15 (m, 8H), 6.85 (t, 1H), 6.80 (t, 1H), 6.21 (t, 1H), 4.00 (d, 2H), 3.69 (q, 1H), 3.19-3.41 (m, 2H), 1.98 (td, 2H), 1.71 (d, 2H), 1.44 (d, 3H).

Example 9(32): 4-[3-(2,4-difluorophenoxy)-5-{[(4-hydroxy-4-isobutyl-1-piperidinyl)carbonyl]amino}phenoxy]benzoic Acid TLC: Rf 0.63 (chloroform:methanol:ethanol=9:1:0.1);
$^1$H-NMR (CDCl$_3$): δ 7.97 (d, 2H), 7.18-7.06 (m, 1H), 7.02-6.75 (m, 6H), 6.28 (m, 1H), 3.73 (m, 2H), 3.30-3.19 (m, 2H), 1.89-1.75 (m, 1H), 1.65-1.43 (m, 4H), 1.38 (d, 2H) 1.29-1.23 (m, 1H), 0.95 (d, 6H).

Example 9(33): {4-[3-(2,4-difluorophenoxy)-5-{[(4-hydroxy-4-isobutyl-1-piperidinyl)carbonyl]amino}phenoxy]phenyl}acetic Acid TLC: Rf 0.63 (chloroform:methanol:ethanol=9:1:0.1);
$^1$H-NMR (CDCl$_3$): δ 7.22 (d, 2H), 7.10 (td, 1H), 7.00-6.79 (m, 5H), 6.60 (t, 1H), 6.27 (t, 1H), 3.70 (m, 2H), 3.52

(s, 2H), 3.28-3.13 (m, 2H), 1.90-1.73 (m, 1H), 1.64-1.47 (m, 4H), 1.37 (d, 2H), 0.95 (d, 6H).

Example 9(34): 2-chloro-4-[3-(2,4-difluorophenoxy)-5-{[(4-hydroxy-4-isobutyl-1-piperidinyl)carbonyl]amino}phenoxy]benzoic Acid TLC: Rf 0.68 (chloroform:methanol:ethanol=9:1:0.1);
$^1$H-NMR (CDCl$_3$): δ 7.70 (d, 2H), 7.13 (m, 1H), 7.03-6.81 (m, 5H), 6.72 (t, 1H), 6.27 (t, 1H), 3.74 (m, 2H), 3.31-3.12 (m, 2H), 1.92-1.72 (m, 1H), 1.48-1.65 (m, 4H), 1.33-1.42 (m, 2H), 1.21-1.30 (m, 1H), 0.86-1.01 (d, 6H).

Example 9(35): {4-[3-(2,4-difluorophenoxy)-5-{[(4-hydroxy-4-isobutyl-1-piperidinyl) carbonyl]amino}phenoxy]-2-fluorophenyl}acetic Acid TLC: Rf 0.56 (dichloromethane:methanol=8:2);
$^1$H-NMR (CD$_3$OD): δ 7.16-7.33 (m, 2H), 7.11 (ddd, 1H), 6.92-7.03 (m, 1H), 6.85 (s, 2H), 6.72-6.82 (m, 2H), 6.24 (t, 1H), 3.80 (dt, 2H), 3.62 (s, 2H), 3.16-3.29 (m, 2H), 1.77-1.95 (m, 1H), 1.43-1.67 (m, 4H), 1.38 (d, 2H) 0.97 (d, 6H).

Example 9(36): 2-{4-[3-(2,4-difluorophenoxy)-5-{[(4-hydroxy-4-isobutyl-1-piperidinyl)carbonyl]amino}phenoxy]phenyl}propanoic Acid TLC: Rf 0.72 (dichloromethane:methanol=8:2);
$^1$H-NMR (CD$_3$OD): δ 7.31 (d, 2H), 7.19 (td, 1H), 7.06-7.15 (m, 1H), 6.91-7.02 (m, 3H), 6.81 (t, 1H), 6.78 (t, 1H), 6.18 (t, 1H), 3.74-3.84 (m, 2H), 3.69 (q, 1H), 3.16-3.29 (m, 2H), 1.75-1.94 (m, 1H), 1.48-1.64 (m, 4H), 1.45 (d, 3H), 1.38 (d, 2H), 0.97 (d, 6H).

Example 9(37): 4-[3-(4-fluorophenoxy)-5-({[4-hydroxy-4-(3-pentanyl)-1-piperidinyl]carbonyl}amino)phenoxy]benzoic Acid TLC: Rf 0.58 (chloroform:methanol=5:1);
$^1$H-NMR (CD$_3$OD): δ 7.98 (d, 1H), 7.18-6.98 (m, 6H), 6.88 (d, 2H), 6.25 (m, 1H), 3.90 (m, 2H), 3.11 (m, 2H), 1.66-1.40 (m, 7H), 1.22-1.10 (m, 2H), 0.86 (t, 6H).

Example 9(38): (2E)-3-{4-[3-(4-fluorophenoxy)-5-{[(4-hydroxy-4-isobutyl-1-piperidinyl)carbonyl]amino}phenoxy]phenyl}acrylic Acid TLC: Rf 0.31 (dichloromethane:methanol=10:1);
$^1$H-NMR (CDCl$_3$): δ 7.49 (dd, 1H), 7.37-7.45 (m, 2H), 6.89-7.01 (m, 6H), 6.75-6.81 (m, 2H), 6.21-6.33 (m, 2H), 3.61-3.73 (m, 2H), 3.09-3.23 (m, 2H), 1.68-1.82 (m, 1H), 1.41-1.59 (m, 4H), 1.31 (dd, 2H), 0.88 (dd, 6H).

Example 9(39): 4-[3-(2,4-difluorophenoxy)-5-({[4-(4-fluorophenyl)-4-hydroxy-1-piperidinyl]carbonyl}amino)phenoxy]benzoic Acid TLC: Rf 0.68 (chloroform:methanol:ethanol=9:1:0.1);
$^1$H-NMR (CDCl$_3$): δ 7.99 (d, 2H), 7.50-7.35 (m, 2H), 7.19-6.80 (m, 9H), 6.30 (t, 1H), 3.94 (m, 2H), 3.39-3.24 (m, 2H), 1.98 (m, 2H), 1.75 (d, 2H).

Example 9(40): 3-{4-[3-(4-fluorophenoxy)-5-{[(4-hydroxy-4-isobutyl-1-piperidinyl)carbonyl]amino}phenoxy]phenyl}propanoic Acid TLC: Rf 0.40 (dichloromethane:methanol=10:1);
$^1$H-NMR (CDCl$_3$): δ 7.13 (d, 2H), 6.95-7.05 (m, 4H), 6.90 (d, 2H), 6.72-6.77 (m, 1H), 6.62-6.67 (m, 1H), 6.24-6.29 (m, 1H), 3.62-3.74 (m, 2H), 3.15-3.25 (m, 2H), 2.80-2.93 (m, 2H), 2.48-2.59 (m, 2H), 1.80 (dquin, 1H), 1.43-1.62 (m, 4H), 1.35 (d, 2H), 0.93 (d, 6H).

Example 9(41): {4-[3-(4-fluorophenoxy)-5-({[4-hydroxy-4-(3-pentanyl)-1-piperidinyl]carbonyl}amino)phenoxy]phenyl}acetic Acid TLC: Rf 0.58 (chloroform:methanol:ethanol=9:1:0.1);
$^1$H-NMR (CDCl$_3$): δ 7.22 (d, 2H), 7.06-6.90 (m, 6H), 6.83 (t, 1H), 6.63 (t, 1H), 6.30 (t, 1H), 3.79 (m, 2H), 3.56 (s, 2H), 3.26-3.01 (m, 2H), 1.67-1.41 (m, 6H), 1.34-1.08 (m, 3H), 1.06-0.84 (m, 7H).

Example 9(42): 2-chloro-4-[3-(4-fluorophenoxy)-5-({[4-hydroxy-4-(3-pentanyl)-1-piperidinyl]carbonyl}amino)phenoxy]benzoic Acid TLC: Rf 0.51 (chloroform:methanol:ethanol=9:1:0.1);
$^1$H-NMR (CDCl$_3$): δ 7.80 (m, 1H), 7.07-6.95 (m, 5H), 6.93-6.72 (m, 3H), 6.30 (t, 1H) 3.82 (m, 2H) 3.28-3.03 (m, 2H), 1.73-1.45 (m, 6H), 1.34-1.11 (m, 3H), 1.06-0.83 (m, 7H).

Example 9(43): 2-{4-[3-(4-fluorophenoxy)-5-({[4-hydroxy-4-(3-pentanyl)-1-piperidinyl]carbonyl}amino)phenoxy]phenyl}-2-ethylpropanoic Acid TLC: Rf 0.56 (chloroform:methanol:ethanol=9:1:0.1);
$^1$H-NMR (CDCl$_3$): δ 7.39-7.29 (m, 2H), 7.07-6.92 (m, 6H), 6.81 (t, 1H), 6.65 (t, 1H), 6.29 (t, 1H), 3.79 (m, 2H), 3.27-3.08 (m, 2H), 1.66-1.42 (m, 12H), 1.33-1.10 (m, 3H), 1.05-0.87 (m, 7H).

Example 9(44): 4-[3-(3,4-difluorophenoxy)-5-({[4-hydroxy-4-(3-pentanyl)-1-piperidinyl]carbonyl}amino)phenoxy]benzoic Acid TLC: Rf 0.76 (dichloromethane:methanol=3:1);
$^1$H-NMR (CD$_3$OD): δ 8.49 (s, 1H), 8.07-7.97 (m, 2H), 7.32-7.23 (m, 1H), 7.11-6.92 (m, 5H), 6.90-6.80 (m, 1H), 6.35 (t, 1H), 3.95-3.80 (m, 2H), 3.27-3.07 (m, 2H), 1.70-1.44 (m, 6H), 1.28-1.08 (m, 2H), 1.06-0.91 (m, 7H).

Example 9(45): 2-chloro-4-[3-(3,4-difluorophenoxy)-5-({[4-hydroxy-4-(3-pentanyl)-1-piperidinyl]carbonyl}amino)phenoxy]benzoic Acid TLC: Rf 0.51 (dichloromethane:methanol=3:1);
$^1$H-NMR (CD$_3$OD): δ 8.52 (s, 1H), 7.92 (d, 1H), 7.31-7.19 (m, 1H), 7.10 (d, 1H), 7.07-6.95 (m, 4H), 6.92-6.81 (m, 1H), 6.38 (t, 1H), 4.00-3.80 (m, 2H), 3.26-3.08 (m, 2H), 1.73-1.46 (m, 6H), 1.29-1.06 (m, 2H), 1.05-0.90 (m, 7H).

Example 9(46): 2-{4-[3-(3,4-difluorophenoxy)-5-{[(4-hydroxy-4-isobutyl-1-piperidinyl)carbonyl]amino}phenoxy]phenyl}-2-methylpropanoic Acid TLC: Rf 0.32 (dichloromethane:methanol=10:1);
$^1$H-NMR (CD$_3$OD): δ 7.43-7.35 (m, 2H), 7.31-7.16 (m, 1H), 7.04-6.91 (m, 3H), 6.90-6.86 (m, 1H), 6.86-6.78 (m, 2H), 6.25 (t, 1H), 3.90-3.70 (m, 2H), 3.28-3.14 (m, 2H), 1.95-1.75 (m, 1H) 1.66-1.45 (m, 10H), 1.39 (d, 2H), 0.97 (d, 6H).

Example 9(47): 4-[3-(3,4-difluorophenoxy)-5-{[(4-hydroxy-4-isobutyl-1-piperidinyl)carbonyl]amino}phenoxy]-3-fluorobenzoic Acid TLC: Rf 0.52 (dichloromethane:methanol=3:1);
$^1$H-NMR (CD$_3$OD): δ 8.47 (s, 1H), 7.88-7.78 (m, 2H), 7.34-7.09 (m, 2H), 7.05-6.94 (m, 1H), 6.94-6.89 (m, 2H), 6.89-6.79 (m, 1H), 6.33 (t, 1H), 3.86-3.69 (m, 2H), 3.28-3.16 (m, 2H), 1.93-1.72 (m, 1H), 1.67-1.43 (m, 4H), 1.38 (d, 2H), 0.96 (d, 6H).

Example 9(48): {4-[3-(3,4-difluorophenoxy)-5-{[(4-hydroxy-4-isobutyl-1-piperidinyl)carbonyl]amino}phenoxy]-2-fluorophenyl}acetic Acid TLC: Rf 0.72 (dichloromethane:methanol=3:1);
$^1$H-NMR (CD$_3$OD): δ 8.45 (s, 1H), 7.34-7.15 (m, 2H), 7.05-6.94 (m, 1H), 6.93-6.87 (m, 2H), 6.86-6.73 (m, 3H), 6.30 (t, 1H), 3.88-3.72 (m, 2H), 3.62 (d, 2H), 3.27-3.17 (m, 2H), 1.92-1.75 (m, 1H), 1.67-1.44 (m, 4H), 1.38 (d, 2H), 0.96 (d, 6H).

Example 9(49): 2-{4-[3-(3,4-difluorophenoxy)-5-{[(4-hydroxy-4-isobutyl-1-piperidinyl)carbonyl]amino}phenoxy]phenyl}propanoic Acid TLC: Rf 0.29 (dichloromethane:methanol=10:1);
$^1$H-NMR (CD$_3$OD): δ 8.42 (s, 1H), 7.36-7.29 (m, 2H), 7.29-7.17 (m, 1H), 7.05-6.90 (m, 3H), 6.89-6.78 (m, 3H), 6.25 (t, 1H), 3.87-3.76 (m, 2H) 3.71 (q, 1H), 3.28-3.14 (m, 2H), 1.96-1.76 (m, 1H), 1.66-1.50 (m, 4H), 1.45 (d, 3H), 1.39 (d, 2H), 0.97 (d, 6H).

Example 9(50): {4-[3-({[4-(2-ethylbutyl)-4-hydroxy-1-piperidinyl]carbonyl}amino)-5-(4-fluorophenoxy)phenoxy]phenoxy}acetic Acid TLC: Rf 0.29 (chloroform:methanol:ethanol=9:1:0.1);
$^1$H-NMR (CDCl$_3$): δ 7.01-6.89 (m, 4H), 6.85-6.66 (m, 5H), 6.58 (m, 1H), 6.18 (m, 1H), 4.37-4.20 (m, 2H), 3.69 (m, 2H), 3.14 (m, 2H), 1.59-1.21 (m, 11H), 0.72-0.87 (m, 6H).

Example 9(51): 2-{4-[3-(4-fluorophenoxy)-5-({[4-hydroxy-4-(3-methylbutyl)-1-piperidinyl]carbonyl}amino)phenoxy]phenyl}-2-methylpropanoic Acid TLC: Rf 0.28 (dichloromethane:methanol=10:1);
$^1$H-NMR (CDCl$_3$): δ 7.33-7.39 (m, 2H), 6.96-7.06 (m, 6H), 6.78-6.81 (m, 1H), 6.69 (t, 1H), 6.38 (s, 1H), 6.30-6.32 (m, 1H), 3.71-3.77 (m, 2H), 3.20-3.31 (m, 2H), 1.53-1.64 (m, 8H), 1.43-1.53 (m, 4H), 1.19-1.31 (m, 4H), 0.90 (d, 6H).

Example 9(52): 2-(4-{3-[(4,4-difluorocyclohexyl)oxy]-5-({[4-(2-ethylbutyl)-4-hydroxy-1-piperidinyl]carbonyl}amino)phenoxy}phenyl)-2-methylpropanoic Acid TLC: Rf 0.45 (chloroform:methanol=9:1);
$^1$H-NMR (CDCl$_3$): δ 7.29 (d, 2H), 6.97-6.84 (m, 3H), 6.63 (m, 1H), 6.41 (m, 1H), 6.27 (m, 1H), 4.43 (m, 1H), 3.80-3.63 (m, 2H), 3.32-3.13 (m, 2H), 2.10-1.71 (m, 7H), 1.21-1.53 (m, 18H), 0.90-0.75 (t, 6H).

Example 9(53): 2-{4-[3-({[4-(2-ethylbutyl)-4-hydroxy-1-piperidinyl]carbonyl}amino)-5-(2-fluorophenoxy)phenoxy]phenyl}-2-methylpropanoic Acid TLC: Rf 0.40 (chloroform:methanol=9:1);
$^1$H-NMR (CDCl$_3$): δ 7.33 (d, 2H), 7.16-7.03 (m, 3H), 6.96 (d, 2H), 6.79-6.64 (m, 2H), 6.42 (m, 1H), 6.35-6.23 (m, 1H), 3.70 (m, 2H), 3.32-3.10 (m, 2H), 1.62-1.52 (m, 8H), 1.46-1.20 (m, 4H), 0.93-0.69 (t, 6H).

Example 9(54): 2-{4-[3-({[4-(2-ethylbutyl)-4-hydroxy-1-piperidinyl]carbonyl}amino)-5-(2-methylphenoxy)phenoxy]phenyl}-2-ethylpropanoic Acid TLC: Rf 0.45 (chloroform:methanol=9:1);
$^1$H-NMR (CDCl$_3$): δ 7.31-7.17 (m, 2H), 7.15-6.98 (m, 2H), 6.95-6.81 (m, 4H), 6.62 (m, 1H), 6.58 (m, 1H), 6.24 (m, 1H), 3.64 (m, 2H), 3.10 (m, 2H), 2.19 (s, 3H), 1.47 (m, 4H), 1.36-1.18 (m, 8H), 0.88-0.73 (t, 6H).

Example 9(55): 2-{4-[3-{[(4-cyclopentyl-4-hydroxy-1-piperidinyl)carbonyl]amino}-5-(4-fluorophenoxy)phenoxy]phenyl}-2-methylpropanoic Acid TLC: Rf 0.49 (chloroform:methanol=9:1);
$^1$H-NMR (CDCl$_3$): δ 7.32 (m, 2H), 7.08-6.90 (m, 6H), 6.76 (m, 1H), 6.66 (m, 1H), 6.48 (m, 1H), 6.29 (m, 1H), 3.74 (m, 2H), 3.18 (m, 2H), 2.11 (m, 4H), 1.78 (m, 1H), 1.74-1.50 (m, 6H), 1.57 (s, 6H), 1.33 (m, 2H).

Example 9(56): 2-{4-[3-{[(4-cyclohexyl-4-hydroxy-1-piperidinyl)carbonyl]amino}-5-(4-fluorophenoxy)phenoxy]phenyl}-2-methylpropanoic Acid TLC: Rf 0.33 (chloroform:methanol=19:1);
$^1$H-NMR (CD$_3$OD): δ 1.00-1.30 (m, 6H), 1.49-1.71 (m, 11H), 1.76-1.86 (m, 4H), 3.10-3.22 (m, 2H), 3.84-3.96 (m, 2H), 6.19 (t, 1H), 6.78-6.84 (m, 2H), 6.95-7.12 (m, 6H), 7.35-7.41 (m, 2H), 8.36 (brs, 1H).

Example 9(57): 2-{3-[3-(4-fluorophenoxy)-5-{[(4-hydroxy-4-isobutyl-1-piperidinyl)carbonyl]amino}phenoxy]phenoxy}-2-methylpropanoic Acid TLC: Rf 0.35 (dichloromethane:methanol=10:1);
$^1$H-NMR (CDCl$_3$): δ 7.21 (t, 1H), 7.04 (d, 4H), 6.82 (t, 1H), 6.71 (d, 1H), 6.69 (d, 1H), 6.50 (t, 1H), 6.46 (t, 1H), 6.33-6.29 (m, 2H), 3.74 (s, 2H), 3.36-3.21 (m, 2H), 2.09 (s, 1H), 1.82 (dt, 1H), 1.63-1.55 (m, 10H), 1.40 (d, 2H), 0.96 (d, 6H).

Example 9(58): 2-{3-[3-(4-fluorophenoxy)-5-{[(4-hydroxy-4-isobutyl-1-piperidinyl) carbonyl]amino}phenoxy]phenyl}-2-methylpropanoic Acid TLC: Rf 0.41 (dichloromethane:methanol=10:1);
¹H-NMR (CDCl₃): δ 7.34-7.28 (m, 1H), 7.18-7.10 (m, 2H), 7.05-6.99 (m, 4H), 6.92 (dd, 1H), 6.68-6.65 (m, 1H), 6.60 (t, 1H), 6.40 (s, 1H), 6.35 (t, 1H), 3.77-3.66 (m, 2H), 3.30-3.17 (m, 2H), 1.83 (dt, 1H), 1.62-1.55 (m, 10H), 1.40 (d, 2H), 0.97 (d, 6H).

Example 9(59): 2-[4-(3-[(4,4-difluorocyclohexyl)oxy]-5-{[(4-hydroxy-4-isobutyl-1-piperidinyl)carbonyl]amino}phenoxy)phenyl]-2-methylpropanoic Acid TLC: Rf 0.38 (dichloromethane:methanol=10:1);
¹H-NMR (CD₃OD): δ 7.41-7.33 (m, 2H), 7.01-6.91 (m, 2H), 6.91-6.84 (m, 1H), 6.63 (t, 1H), 6.25 (t, 1H), 4.54-4.40 (m, 1H), 3.90-3.73 (m, 2H), 3.28-3.16 (m, 2H), 2.19-1.75 (m, 9H), 1.55 (s, 6H), 1.68-1.45 (m, 4H), 1.40 (d, 2H), 0.98 (d, 6H).

Example 9(60): 2-{3-fluoro-4-[3-(4-fluorophenoxy)-5-{[(4-hydroxy-4-isobutyl-1-piperidinyl)carbonyl]amino}phenoxy]phenyl}-2-methylpropanoic Acid TLC: Rf 0.40 (dichloromethane:methanol=10:1);
¹H-NMR (CD₃OD): δ 7.29-7.22 (m, 1H), 7.22-7.16 (m, 1H), 7.14-6.98 (m, 5H), 6.85-6.81 (m, 1H), 6.75 (t, 1H), 6.17 (t, 1H), 3.86-3.71 (m, 2H), 3.29-3.15 (m, 2H), 1.95-1.73 (m, 1H), 1.55 (s, 6H), 1.64-1.45 (m, 4H), 1.39 (d, 2H), 0.97 (d, 6H).

Example 9(61): 1-{4-[3-(4-fluorophenoxy)-5-{[(4-hydroxy-4-isobutyl-1-piperidinyl) carbonyl]amino}phenoxy]phenoxy}cyclopropanecarboxylic Acid TLC: Rf 0.31 (dichloromethane:methanol=10:1);
¹H-NMR (CDCl₃): δ 7.06-6.86 (m, 8H), 6.69 (t, 1H), 6.58 (s, 1H), 6.53 (t, 1H), 6.28 (t, 1H), 3.70 (dt, 2H), 3.26-3.13 (m, 2H), 1.90-1.75 (m, 1H), 1.69-1.62 (m, 2H), 1.61-1.53 (m, 4H), 1.42-1.33 (m, 4H), 0.97 (d, 6H).

Example 9(62): N-{3-(4-fluorophenoxy)-5-[(6-isopropyl-3-pyridinyl)oxy]phenyl}-4-hydroxy-4-isobutyl-1-piperidinecarboxamide TLC: Rf 0.53 (dichloromethane:methanol=10:1);
¹H-NMR (CDCl₃): δ 8.32 (d, 1H), 7.31-7.27 (m, 1H), 7.15 (d, 1H), 7.07-6.98 (m, 4H), 6.80-6.75 (m, 2H), 6.34 (s, 1H), 6.29 (t, 1H), 3.81-3.70 (m, 2H), 3.34-3.23 (m, 2H), 3.12-2.96 (m, 1H), 1.85 (dt, 1H), 1.64-1.59 (m, 4H), 1.42 (d, 2H), 1.30 (d, 6H), 1.07 (s, 1H), 0.98 (d, 6H).

Example 9(63): 2-{4-[3-{[(4-cyclopentyl-4-hydroxy-1-piperidinyl)carbonyl]amino}-5-(4-fluorophenoxy)phenoxy]phenoxy}-2-methylpropanoic Acid TLC: Rf 0.13 (dichloromethane:methanol=10:1);
¹H-NMR (CDCl₃): δ 7.37 (s, 1H), 6.99-6.89 (m, 4H), 6.83 (s, 4H), 6.77-6.71 (m, 1H), 6.62-6.56 (m, 1H), 6.19-6.12 (m, 1H), 3.77-3.66 (m, 2H), 3.18-3.02 (m, 2H), 1.83-1.68 (m, 1H), 1.62-1.38 (m, 16H), 1.35-1.23 (m, 2H).

Example 9(64): 2-{4-[3-{[(4-cyclopentyl-4-hydroxy-1-piperidinyl)carbonyl]amino}-5-(4-fluorophenoxy)phenoxy]-2-fluorophenyl}-2-methylpropanoic Acid TLC: Rf 0.47 (dichloromethane:methanol=10:1);
¹H-NMR (CDCl₃): δ 7.30-7.21 (m, 1H), 7.08-6.97 (m, 4H), 6.84 (t, 1H), 6.81-6.65 (m, 3H), 6.50 (s, 1H), 6.34-6.31 (m, 1H), 3.85-3.74 (m, 2H), 3.30-3.17 (m, 2H), 1.93-1.79 (m, 1H), 1.73-1.49 (m, 16H), 1.42-1.31 (m, 2H).

Example 10: 1-fluoro-3-(4-fluorophenoxy)-5-nitrobenzene

Under an argon atmosphere and at room temperature, in a 500-mL pear-shaped evaporating flask, 4-fluorophenol (18.5 g) and 1,3-difluoro-5-nitrobenzene (25.0 g) were dissolved in DMA (300 mL). The reaction system was added with cesium carbonate (15.3 g) and stirred. The reaction system was then heated to 50° C., stirred for 3 hours, then heated to 65° C., stirred for 1 hour and further heated to 85° C. and stirred for 1 hour. The reaction solution was allowed to cool to room temperature, diluted with ethyl acetate and added with water to extract an organic layer. The aqueous layer was added with ethyl acetate to extract an organic layer. The organic layer was combined and washed with water and a saturated sodium chloride solution and the solvent was then distilled off under reduced pressure to give the titled compound (35.0 g) having the following physical properties.

TLC: Rf 0.83 (hexane:ethyl acetate=5:1);
¹H-NMR (CDCl₃): δ 6.98 (dt, J=9.3, 2.3 Hz, 1H), 7.03-7.18 (m, 4H), 7.56 (td, J=2.1, 1.1 Hz, 1H), 7.62 (dt, J=8.1, 2.2 Hz, 1H).

Example 11: 1-(4-fluorophenoxy)-3-(4-iodophenoxy)-5-nitrobenzene

At room temperature, to a 300-mL three-neck flask were added 4-iodophenol (44.4 g) and further the compound prepared in Example 10 (34.9 g) dissolved in DMA (140 mL) and potassium phosphate (59.2 g) and the flask was purged with argon. The reaction solution was heated to 105° C. and stirred for 7 hours. The reaction solution was allowed to cool to room temperature, diluted with ethyl acetate and added with water to extract an organic layer. The organic layer was washed twice with water, twice with 1 N sodium hydroxide and with a saturated sodium chloride solution and then dried over anhydrous sodium sulphate and the solvent was distilled off under reduced pressure. The resulting residue was added with a seed crystal (5 mg) and the solid was precipitated under reduced pressure. The solid was added with hexane (300 mL), stirred and left to stand at room temperature to precipitate the solid. The solid was collected by filtration with a Kiriyama funnel and washed with hexane. The resulting residue was dried under reduced pressure at 60° C. to give the titled compound (53.1 g). The filtrate was subjected to silica gel column chromatography (hexane:MTBE=99:1→95:5) to give a pale yellow oily substance. Re-crystallization was carried out with a mixed solvent of hexane and MTBE, and the titled compound (14.4 g) was obtained after filtration with a Kiriyama funnel and washing with hexane. The titled compound having the following physical properties was obtained at a total amount of 67.5 g.

TLC: Rf 0.31 (hexane:ethyl acetate=10:1);
$^1$H-NMR (CDCl$_3$): δ 6.81-6.87 (m, 2H), 6.91 (dd, J=2.1 Hz, 1H), 7.02-7.14 (m, 4H), 7.42-7.45 (m, 2H), 7.68-7.73 (m, 2H).

Example 12: Methyl 1-{4-[3-(4-bromophenoxy)-5-nitrophenoxy]phenyl}cyclopropanecarboxylate Under an argon atmosphere and at room temperature, to a solution of zinc (87 mg) in dimethoxyethane (DME) (1.0 mL) in a 100-mL three-neck flask were added sequentially lithium chloride (37.6 mg) and chlorotrimethylsilane (TM-SCl) (11.3 μL). The mixture was heated to 75° C., added dropwise with methyl 1-bromocyclopropane carboxylate and further stirred at 75° C. for 2 hours (this solution is referred to as the solution 1). Under an argon atmosphere and at room temperature, N-methyl-2-pyrrolidone (NMP) (1.0 mL) was added, degassed and charged with argon. Bis(tri-tert-butylphosphine)palladium (0) (Pd(t-Bu$_3$P)$_2$) (23 mg) was added thereto, stirred for 10 minutes before addition of the compound prepared in Example 11 (200 mg). The mixture was heated to 95° C. and the solution 1 prepared as above was added dropwise over 30 minutes. The mixture was further stirred at 95° C. for 1.5 hours. The reaction solution was allowed to cool, diluted with ethyl acetate and filtered with celite. The filtrate was washed with water and a saturated sodium chloride solution and dried over anhydrous sodium sulphate and the solvent was distilled off under reduced pressure. The solid was filtered, the resulting residue was purified by silica gel chromatography (hexane:ethyl acetate=90:10→80:20→50:50→0:100) to give the titled compound (143 mg) having the following physical properties.

TLC: Rf 0.42 (hexane:ethyl acetate=4:1).

Example 13: 1-{4-[3-(4-fluorophenoxy)-5-({[4-hydroxy-4-(3-pentanyl)-1-piperidinyl]carbonyl}amino)phenoxy]phenyl}cyclopropanecarboxylic Acid

[C 16]

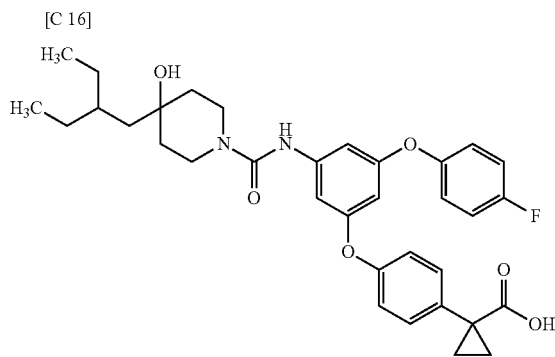

The titled compound (12.0 g) having the following physical properties was obtained by carrying out the processes with the same purposes as Example 6→Example 7→Example 8→Example 9 using the compound prepared in Example 12 (22.4 g), 2,2,2-trichloroethyl chloroformate and 4-(2-ethylbutyl)-4-piperidinol in the place of 4-isobutyl-4-piperidinol.

TLC: Rf 0.32 (chloroform:ethanol=20:1);
$^1$H-NMR (CDCl$_3$) δ 7.30-7.25 (m, 2H), 7.05-6.97 (m, 3H), 6.96-6.90 (m, 2H), 6.88 (t, 1H), 6.65 (t, 1H), 6.30 (t, 1H), 3.81 (m, 2H), 3.25-3.09 (m, 2H), 1.69-1.43 (m, 8H), 1.23-1.10 (m, 5H), 1.07-0.88 (m, 7H).

Examples 13(1) to 13(8)

The compounds of the following Examples were obtained by carrying out the processes with the same purposes as Example 10→Example 11→Example 12→Example 13 using 1,3-difluoro-5-nitrobenzene; 4-iodophenol or a corresponding phenol derivative instead thereof; 4-fluorophenol or a corresponding phenol derivative instead thereof; 2,2,2-trichloroethyl chloroformate; methyl 1-bromocyclopropane carboxylate or a corresponding bromide instead thereof; and 4-isobutyl-4-piperidinol or a corresponding piperidine derivative instead thereof.

Example 13(1): 1-{4-[3-({[4-(2-ethylbutyl)-4-hydroxy-1-piperidinyl]carbonyl}amino)-5-(4-fluorophenoxy)phenoxy]phenyl}cyclopropanecarboxylic Acid TLC: Rf 0.30 (dichloromethane:methanol=10:1);
$^1$H-NMR (CDCl$_3$): δ 7.29-7.32 (m, 2H), 7.01 (d, 4H), 6.88-6.97 (m, 3H), 6.55-6.61 (m, 1H), 6.31-6.32 (m, 1H), 3.74 (d, 2H), 3.13-3.20 (m, 2H), 1.51-1.58 (m, 4H), 1.40-1.45 (m, 2H), 1.27-1.39 (m, 7H), 0.97 (m, 2H), 0.84 (t, 6H).

Example 13(2): 1-{4-[3-(4-fluorophenoxy)-5-{[(4-hydroxy-4-isobutyl-1-piperidinyl)carbonyl]amino}phenoxy]phenyl}cyclopropanecarboxylic Acid TLC: Rf 0.16 (dichloromethane:methanol=10:1);
$^1$H-NMR (CDCl$_3$): δ 7.24-7.29 (m, 2H), 6.95-7.02 (m, 4H), 6.91 (d, 2H), 6.85 (t, 1H), 6.60 (t, 1H), 6.27 (t, 1H), 3.62-3.75 (m, 2H), 3.13-3.27 (m, 2H), 1.79 (dquin, 1H), 1.39-1.64 (m, 6H), 1.34 (d, 2H), 1.06-1.13 (m, 2H), 0.92 (d, 6H).

Example 13(3): 1-{4-[3-(3,4-difluorophenoxy)-5-{[(4-hydroxy-4-isobutyl-1-piperidinyl)carbonyl]amino}phenoxy]phenyl}cyclopropanecarboxylic Acid TLC: Rf 0.47 (ethyl acetate:methanol=10:1);
$^1$H-NMR (CDCl$_3$): δ 7.39-7.30 (m, 2H), 7.31-7.16 (m, 1H), 7.04-6.92 (m, 3H), 6.88 (t, 1H), 6.86-6.81 (m, 2H), 6.26 (t, 1H), 3.90-3.75 (m, 2H), 3.28-3.16 (m, 2H), 1.95-1.75 (m, 1H), 1.67-1.45 (m, 6H), 1.39 (d, 2H), 1.22-1.13 (m, 2H), 0.97 (d, 6H).

Example 13(4): 1-{4-[3-(4-fluorophenoxy)-5-({[4-(4-fluorophenyl)-4-hydroxy-1-piperidinyl]carbonyl}amino)phenoxy]phenyl}cyclopropanecarboxylic Acid TLC: Rf 0.38 (chloroform:methanol=9:1);
$^1$H-NMR (CD$_3$OD): δ 7.43-7.57 (m, 2H), 7.28-7.39 (m, 2H), 6.91-7.16 (m, 8H), 6.86 (t, 1H), 6.77-6.84 (m, 1H), 6.22 (t, 1H), 4.00 (d, 2H), 3.25-3.41 (m, 2H), 1.88-2.07 (m, 2H), 1.71 (d, 2H), 1.48-1.63 (m, 2H), 1.07-1.24 (m, 2H).

Example 13(5): 1-{4-[3-(2,4-difluorophenoxy)-5-{[(4-hydroxy-4-isobutyl-1-piperidinyl) carbonyl]amino}phenoxy]phenyl}cyclopropanecarboxylic Acid TLC: Rf 0.62 (chloroform:methanol:ethanol=9:1:0.1);
$^1$H-NMR (CDCl$_3$) δ 7.35-7.22 (m, 2H), 7.10 (td, 1H), 6.99-6.81 (m, 5H), 6.62 (t, 1H), 6.28 (t, 1H), 3.72 (m, 2H), 3.30-3.16 (m, 2H), 1.90-1.70 (m, 1H), 1.67-1.44 (m, 6H), 1.38 (d, 2H), 1.15-1.07 (m, 2H), 0.95 (d, 6H).

Example 13(6): 1-{2-fluoro-4-[3-(4-fluorophenoxy)-5-{[(4-hydroxy-4-isobutyl-1-piperidinyl)carbonyl]amino}phenoxy]phenyl}cyclopropanecarboxylic Acid TLC: Rf 0.32 (dichloromethane:methanol=10:1);
$^1$H-NMR (CDCl$_3$): δ 7.11-7.20 (m, 1H), 6.95-7.07 (m, 4H), 6.88 (t, 1H), 6.60-6.74 (m, 3H), 6.28 (t, 1H), 3.63-3.76 (m, 2H), 3.12-3.27 (m, 2H), 1.73-1.86 (m, 1H), 1.49-1.65 (m, 6H), 1.36 (d, 2H), 1.06-1.14 (m, 2H), 0.93 (d, 6H).

Example 13(7): 1-{4-[3-{[(4-cyclopentyl-4-hydroxy-1-piperidinyl)carbonyl]amino}-5-(4-fluorophenoxy)phenoxy]phenoxy}cyclopropanecarboxylic Acid TLC: Rf 0.15 (dichloromethane:methanol=10:1);
$^1$H-NMR (CDCl$_3$): δ 7.07-6.84 (m, 8H), 6.73 (s, 1H), 6.60-6.50 (m, 2H), 6.28 (t, 1H), 3.80-3.69 (m, 2H), 3.24-3.10 (m, 2H), 1.91-1.76 (m, 1H), 1.70-1.47 (m, 12H), 1.41-1.31 (m, 4H).

Example 13(8): 1-{3-[3-(4-fluorophenoxy)-5-{[(4-hydroxy-4-isobutyl-1-piperidinyl) carbonyl]amino}phenoxy]phenoxy}cyclopropanecarboxylic Acid TLC: Rf 0.16 (dichloromethane:methanol=10:1);
$^1$H-NMR (CDCl$_3$): δ 7.26-7.21 (m, 1H), 7.07-7.01 (m, 4H), 6.77-6.64 (m, 4H), 6.48-6.43 (m, 1H), 6.40-6.33 (m, 1H), 6.33-6.24 (m, 1H), 3.79-3.66 (m, 2H), 3.35-3.20 (m, 2H), 1.82 (dt, 1H), 1.63-1.51 (m, 6H), 1.39 (d, 2H), 1.33-1.25 (m, 2H), 0.96 (d, 6H).

Example 14: N-[3-(4-carbamoylphenoxy)-5-(4-fluorophenoxy) phenyl]-4-(2-ethylbutyl)-4-hydroxy-1-piperidinecarboxamide

[C 17]

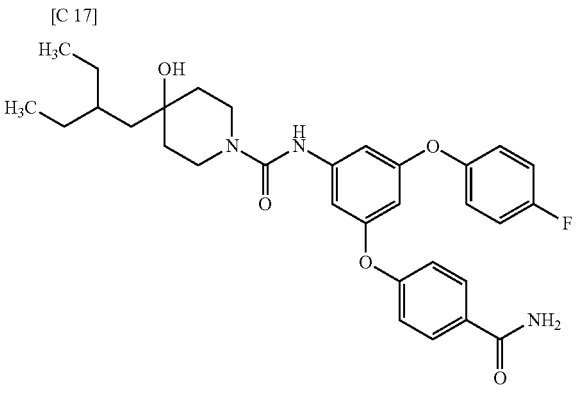

The titled compound having the following physical properties was obtained by carrying out the processes with the same purposes as Example 10→Example 11→Example 6→Example 7→Example 8 using 1,3-difluoro-5-nitrobenzene; a corresponding phenol derivative in the place of 4-iodophenol; 4-fluorophenol; 2,2,2-trichloroethyl chloroformate; and 4-(2-ethylbutyl)-4-piperidinol in the place of 4-isobutyl-4-piperidinol.

TLC: Rf 0.59 (ethyl acetate);
$^1$H-NMR (CDCl$_3$): δ 7.74 (d, 2H), 6.99-7.08 (m, 6H), 6.79 (s, 1H), 6.83 (s, 1H), 6.62 (s, 1H), 6.33 (t, 1H), 3.76 (d, 2H), 3.11-3.36 (m, 2H), 1.25-1.62 (m, 11H), 1.15 (s, 1H), 0.78-0.94 (m, 6H).

Examples 14(1) to 14(30)

The compounds of the following Examples were obtained by carrying out the processes with the same purposes as Example 10→Example 11→Example 6→Example 7→Example 8 using 1,3-difluoro-5-nitrobenzene; a corresponding phenol derivative in the place of 4-iodophenol; 4-fluorophenol or a corresponding phenol derivative instead thereof; 2,2,2-trichloroethyl chloroformate; and a corresponding piperidine derivative in the place of 4-isobutyl-4-piperidinol.

Example 14(1): 4-(2-ethylbutyl)-N-{3-(4-fluorophenoxy)-5-[4-(methylsulphonyl)phenoxy]phenyl}-4-hydroxy-1-piperidinecarboxamide TLC: Rf 0.34 (dichloromethane:methanol=30:1);
$^1$H-NMR (CDCl$_3$): δ 7.79-7.94 (m, 2H), 6.90-7.17 (m, 7H), 6.77 (t, 1H), 6.42 (s, 1H), 6.29-6.39 (m, 1H), 3.77 (d, 2H), 3.18-3.38 (m, 2H), 3.04 (s, 3H), 1.19-1.66 (m, 11H), 1.06 (s, 1H), 0.75-0.92 (m, 6H).

Example 14(2): 5-[3-({[4-(2-ethylbutyl)-4-hydroxy-1-piperidinyl]carbonyl}amino)-5-(4-fluorophenoxy)phenoxy]-2-pyridinecarboxamide TLC: Rf 0.31 (dichloromethane:methanol=10:1);
$^1$H-NMR (CDCl$_3$): δ 8.30 (d, 1H), 8.14 (d, 1H), 7.68 (d, 1H), 7.38 (dd, 1H), 7.11-6.91 (m, 5H), 6.77 (t, 1H), 6.45 (s, 1H), 6.34 (t, 1H) 5.52 (br. s., 1H), 3.85-3.72 (m, 2H), 3.40-3.18 (m, 2H), 1.69-1.52 (m, 4H), 1.47-1.20 (m, 7H), 1.06 (s, 1H), 0.85 (t, 6H).

Example 14(3): N-[3-(4-carbamoylphenoxy)-5-(4-fluorophenoxy)phenyl]-4-(4-chlorophenyl)-4-hydroxy-1-piperidinecarboxamide TLC: Rf 0.41 (dichloromethane:methanol=9:1);
$^1$H-NMR (CDCl$_3$+CD$_3$OD): δ 7.78 (m, 2H), 7.41-7.29 (m, 6H), 7.06-7.01 (m, 4H), 6.88-6.82 (m, 2H), 6.33 (t, 1H), 3.94 (m, 2H), 3.33 (m, 2H), 1.95 (m, 2H), 1.72 (m, 2H).

Example 14(4): N-[3-(4-carbamoylphenoxy)-5-(4-fluorophenoxy)phenyl]-4-(4-fluorophenyl)-4-hydroxy-1-piperidinecarboxamide TLC: Rf 0.39 (chloroform:methanol=9:1);
$^1$H-NMR (CDCl$_3$+CD$_3$OD): δ 7.78 (m, 2H), 7.45-7.40 (m, 4H), 7.06-6.85 (m, 7H), 6.89-6.84 (m, 2H), 6.33 (t, 1H), 3.94 (m, 2H), 3.33 (m, 2H), 1.95 (m, 2H), 1.72 (m, 2H).

Example 14(5): 4-(2-ethylbutyl)-N-{3-(4-fluorophenoxy)-5-[(3-methyl-4-pyridinyl)oxy]phenyl}-4-hydroxy-1-piperidinecarboxamide TLC: Rf 0.45 (ethyl acetate:methanol=20:1);
$^1$H-NMR (CDCl$_3$): δ 8.36 (br. s., 1H), 8.28 (d, 1H), 7.09-6.95 (m, 4H), 6.91 (t, 1H), 6.80 (t, 1H), 6.67 (d, 1H), 6.46 (s, 1H), 6.32 (t, 1H) 3.87-3.72 (m, 2H), 3.36-3.16 (m, 2H), 2.26 (s, 3H) 1.79-1.46 (m, 4H), 1.46-1.21 (m, 7H) 1.11 (br. s., 1H), 0.85 (t, 6H).

Example 14(6): N-{3-[(2,6-dimethyl-3-pyridinyl)oxy]-5-(4-fluorophenoxy)phenyl}-4-(2-ethylbutyl)-4-hydroxy-1-piperidinecarboxamide TLC: Rf 0.17 (hexane:ethyl acetate=3:7);
$^1$H-NMR (CDCl$_3$): δ 7.16 (d, 1H), 7.09-6.92 (m, 5H), 6.72 (t, 1H), 6.63 (t, 1H), 6.35 (s, 1H), 6.20 (t, 1H), 3.83-3.70 (m, 2H), 3.35-3.17 (m, 2H), 2.51 (s, 3H), 2.42 (s, 3H), 1.67-1.55 (m, 4H), 1.44-1.27 (m, 7H), 1.04 (s, 1H), 0.85 (t, 6H).

Example 14(7): 4-(2-ethylbutyl)-N-[3-(4-fluorophenoxy)-5-(4-sulphamoylphenoxy)phenyl]-4-hydroxy-1-piperidinecarboxamide TLC: Rf 0.36 (hexane:ethyl acetate=2:1);
$^1$H-NMR (DMSO-d$_6$): δ 8.57 (s, 1H), 7.81 (d, 2H), 7.31 (s, 2H), 7.27-7.09 (m, 6H), 7.05 (dd, 1H), 6.99 (dd, 1H), 6.30 (dd, 1H), 4.08 (s, 1H), 3.74-3.69 (m, 2H), 3.11-3.03 (m, 2H), 1.46-1.24 (m, 11H), 0.78 (t, 6H).

Example 14(8): 4-(4-bromophenyl)-N-[3-(4-fluorophenoxy)-5-(4-sulphamoylphenoxy)phenyl]-4-hydroxy-1-piperidinecarboxamide TLC: Rf 0.27 (hexane:ethyl acetate=1:2);
$^1$H-NMR (DMSO-d$_6$): δ 8.64 (s, 1H), 7.82 (d, 2H), 7.48 (d, 2H), 7.41 (d, 2H), 7.32 (s, 2H), 7.27-7.10 (m, 6H), 7.08 (dd, 1H), 7.02 (dd, 1H), 6.32 (dd, 1H), 5.18 (s, 1H), 3.98-3.94 (m, 2H), 3.18-3.10 (m, 2H), 1.83-1.76 (m, 2H), 1.58-1.53 (m, 2H).

Example 14(9): 4-(4-bromophenyl)-N-{3-(4-fluorophenoxy)-5-[4-(methylsulphonyl)phenoxy]phenyl}-4-hydroxy-1-piperidinecarboxamide TLC: Rf 0.35 (hexane:ethyl acetate=1:2);
$^1$H-NMR (CDCl$_3$): δ 7.87 (d, 2H), 7.48 (d, 2H), 7.33 (d, 2H), 7.11 (d, 2H), 7.05-7.01 (m, 4H), 6.97 (dd, 1H), 6.79 (dd, 1H), 6.50 (brs, 1H), 6.36 (dd, 1H), 3.96-3.92 (m, 2H), 3.42-3.34 (m, 2H), 3.04 (s, 3H), 2.06-1.95 (m, 2H), 1.79-1.75 (m, 2H), 1.66 (brs, 1H).

Example 14(10): N-{3-(4-fluorophenoxy)-5-[4-(methylsulphonyl)phenoxy]phenyl}-4-hydroxy-4-[4-(trifluoromethyl)phenyl]-1-piperidinecarboxamide TLC: Rf 0.35 (hexane:ethyl acetate=1:2);
$^1$H-NMR (CDCl$_3$): δ 7.87 (d, 2H), 7.63 (d, 2H), 7.58 (d, 2H), 7.11 (d, 2H), 7.07-7.01 (m, 4H), 6.97 (dd, 1H), 6.79 (dd, 1H), 6.48 (brs, 1H), 6.37 (dd, 1H), 3.99-3.95 (m, 2H), 3.45-3.37 (m, 2H), 3.05 (s, 3H), 2.11-2.01 (m, 2H), 1.82-1.77 (m, 2H), 1.71 (brs, 1H).

Example 14(11): N-[3-(4-carbamoyl-3-methylphenoxy)-5-(4-fluorophenoxy)phenyl]-4-(2-ethylbutyl)-4-hydroxy-1-piperidinecarboxamide TLC: Rf 0.15 (hexane:ethyl acetate=3:7);
$^1$H-NMR (CDCl$_3$): δ 7.40 (d, 1H), 7.09-6.95 (m, 4H), 6.86 (d, 1H), 6.83-6.77 (m, 2H), 6.73 (t, 1H), 6.54 (s, 1H), 6.32 (t, 1H), 5.95 (br. s., 1H), 5.60 (br. s., 1H), 3.83-3.70 (m, 2H), 3.33-3.09 (m, 2H), 2.46 (s, 3H) 1.64-1.45 (m, 4H), 1.43-1.26 (m, 7H), 1.12 (s, 1H), 0.84 (t, 6H).

Example 14(12): N-[3-(2-carbamoylphenoxy)-5-(4-fluorophenoxy)phenyl]-4-(2-ethylbutyl)-4-hydroxy-1-piperidinecarboxamide TLC: Rf 0.20 (hexane:ethyl acetate=3:7);
$^1$H-NMR (CDCl$_3$): δ 8.20 (dd, 1H), 7.48-7.37 (m, 2H), 7.21 (t, 1H), 7.08-6.96 (m, 4H), 6.93 (d, 1H), 6.87 (t, 1H), 6.79 (t, 1H), 6.41 (s, 1H), 6.33 (t, 1H), 5.73 (br. s., 1H), 3.83-3.72 (m, 2H), 3.34-3.15 (m, 2H), 1.66-1.50 (m, 4H), 1.44-1.29 (m, 7H), 1.06 (s, 1H), 0.85 (t, 6H).

Example 14(13): N-[3-(4-carbamoylphenoxy)-5-(4-fluorophenoxy)phenyl]-4-hydroxy-4-(3-pentanyl)-1-piperidinecarboxamide TLC: Rf 0.37 (chloroform:methanol=9:1);
$^1$H-NMR (CDCl$_3$+CD$_3$OD): δ 7.74 (m, 2H), 7.10-6.84 (m, 6H), 6.84 (m, 1H), 6.79 (m, 1H), 6.69 (m, 1H), 6.33 (t, 1H), 3.81 (m, 2H), 3.19 (m, 2H), 1.80-1.40 (m, 5H), 1.20-1.08 (m, 4H), 0.94 (t, 6H).

Example 14(14): N-[3-(4-carbamoylphenoxy)-5-(4-fluorophenoxy)phenyl]-4-hydroxy-4-phenyl-1-piperidinecarboxamide TLC: Rf 0.35 (dichloromethane:methanol=10:1);
$^1$H-NMR (DMSO-d$_6$): δ 8.61 (s, 1H), 7.90 (d, 3H), 7.45 (d, 2H), 7.32-7.05 (m, 11H), 7.00 (dd, 1H), 6.27 (dd, 1H), 5.05 (s, 1H), 3.97-3.93 (m, 2H), 3.19-3.11 (m, 2H), 1.85-1.78 (m, 2H), 1.60-1.55 (m, 2H).

Example 14(15): N-[3-(4-fluorophenoxy)-5-(4-sulphamoylphenoxy)phenyl]-4-(4-fluorophenyl)-4-hydroxy-1-piperidinecarboxamide TLC: Rf 0.38 (hexane:ethyl acetate=1:2);
$^1$H-NMR (CDCl$_3$): δ 7.87 (d, 2H), 7.44 (d, 2H), 7.41 (d, 2H), 7.09-7.01 (m, 6H), 6.94 (dd, 1H), 6.77 (dd, 1H), 6.45 (brs, 1H), 6.36 (dd, 1H), 4.77 (brs, 2H), 3.95-3.92 (m, 2H), 3.44-3.35 (m, 2H), 2.07-1.97 (m, 2H), 1.82-1.78 (m, 2H).

Example 14(16): N-{3-(4-fluorophenoxy)-5-[4-(methylsulphonyl)phenoxy]phenyl}-4-(4-fluorophenyl)-4-hydroxy-1-piperidinecarboxamide TLC: Rf 0.38 (hexane:ethyl acetate=1:2);
$^1$H-NMR (CDCl$_3$): δ 7.87 (d, 2H), 7.43 (dd, 2H), 7.12 (d, 2H), 7.09-7.01 (m, 6H), 6.98 (dd, 1H), 6.79 (dd, 1H), 6.45 (brs, 1H), 6.36 (dd, 1H), 3.97-3.92 (m, 2H), 3.45-3.36 (m, 2H), 3.05 (s, 3H), 2.08-1.98 (m, 2H), 1.83-1.79 (m, 2H).

Example 14(17): N-[3-(4-carbamoylphenoxy)-5-(4-fluorophenoxy)phenyl]-4-(3-fluorophenyl)-4-hydroxy-1-piperidinecarboxamide TLC: Rf 0.53 (ethyl acetate);
$^1$H-NMR (CDCl$_3$): δ 7.87-7.71 (m, 2H), 7.40-7.30 (m, 1H), 7.23-7.13 (m, 2H), 7.09-6.91 (m, 7H), 6.86 (t, 1H), 6.81 (t, 1H), 6.42 (s, 1H) 6.36 (t, 1H) 6.20-5.40 (m, 2H), 4.02-3.91 (m, 2H), 3.47-3.33 (m, 2H) 2.12-1.92 (m, 2H) 1.85-1.75 (m, 2H), 1.60 (s, 1H).

Example 14(18): N-[3-(4-carbamoyl-2-chlorophenoxy)-5-(4-fluorophenoxy)phenyl]-4-(2-ethylbutyl)-4-hydroxy-1-piperidinecarboxamide TLC: Rf 0.67 (chloroform:methanol=9:1);
$^1$H-NMR (CD$_3$OD): δ 8.02 (d, 1H), 7.79 (m, 1H), 7.18-7.00 (m, 5H), 6.85 (m, 2H), 6.23 (t, 1H), 3.82 (m, 2H), 3.20 (m, 2H), 1.64-1.42 (m, 11H), 0.86 (t, 6H).

Example 14(19): N-[3-(4-carbamoylphenoxy)-5-(4-fluorophenoxy)phenyl]-4-(3,3-dimethyl-1-butyn-1-yl)-4-hydroxy-1-piperidinecarboxamide TLC: Rf 0.49 (chloroform:methanol=9:1);
$^1$H-NMR (CDCl$_3$): δ 7.76 (d, 2H), 6.93-7.12 (m, 6H), 6.81-6.85 (m, 1H), 6.78 (t, 1H), 6.44 (br. s., 1H), 6.35 (t, 1H), 5.77 (br. s, 2H), 3.63-3.84 (m, 2H), 3.27 (ddd, 2H), 2.01 (s, 1H), 1.63-1.94 (m, 4H), 1.21 (s, 9H).

Example 14(20): N-[3-(4-carbamoylphenoxy)-5-(4-fluorophenoxy)phenyl]-4-hydroxy-4-isopropyl-1-piperidinecarboxamide TLC: Rf 0.39 (dichloromethane:methanol=10:1);
$^1$H-NMR (DMSO-d$_6$): δ 8.54 (s, 1H), 7.92 (brs, 1H), 7.89 (d, 2H), 7.30 (brs, 1H), 7.23 (t, 2H), 7.13-7.04 (m, 4H), 7.02 (dd, 1H), 6.98 (dd, 1H), 6.26 (dd, 1H), 4.00 (s, 1H), 3.84-3.80 (m, 2H), 3.04-2.95 (m, 2H), 1.49-1.27 (m, 5H), 0.81 (d, 6H).

Example 14(21): N-[3-(4-carbamoyl-3-chlorophenoxy)-5-(4-fluorophenoxy)phenyl]-4-(2-ethylbutyl)-4-hydroxy-1-piperidinecarboxamide TLC: Rf 0.54 (chloroform:methanol=9:1);
$^1$H-NMR (CDCl$_3$): δ 7.74 (m, 2H), 7.10-6.80 (m, 8H), 6.58-6.30 (m, 3H), 5.78 (m, 1H), 3.76 (m, 2H), 3.28 (m, 2H), 1.70-1.20 (m, 11H), 1.04 (s, 1H), 0.85 (t, 6H).

Example 14(22): N-[3-(4-carbamoylphenoxy)-5-(4-fluorophenoxy)phenyl]-4-cycloheptyl-4-hydroxy-1-piperidinecarboxamide TLC: Rf 0.27 (ethyl acetate);
$^1$H-NMR (CDCl$_3$): δ 7.77 (d, 2H), 6.96-7.09 (m, 6H), 6.85 (t, 1H), 6.79 (t, 1H), 6.44 (s, 1H), 6.34 (t, 1H) 6.04 (br. s., 1H), 5.52 (br. s., 1H), 3.73-3.87 (m, 2H), 3.22 (td, 2H) 1.16-1.88 (m, 17H), 1.07 (s, 1H).

Example 14(23): N-[3-(4-carbamoylphenoxy)-5-(4-fluorophenoxy)phenyl]-4-(2-ethyl-1-buten-1-yl)-4-hydroxy-1-piperidinecarboxamide TLC: Rf 0.48 (chloroform:methanol=9:1);
$^1$H-NMR (CDCl$_3$): δ 7.75 (d, 2H), 6.93-7.18 (m, 6H), 6.70-6.93 (m, 2H), 6.55 (s, 1H), 6.33 (s, 1H), 5.77 (br. d, 2H), 5.17 (s, 1H), 3.62 (d, 2H) 3.18-3.52 (m, 2H), 2.36 (q, 2H), 2.01 (q, 2H), 1.46-1.88 (m, 4H), 1.31-1.46 (m, 1H), 0.99 (q, 6H).

Example 14(24): 4-(2-ethylbutyl)-N-{3-(4-fluorophenoxy)-5-[4-(methylsulphamoyl)phenoxy]phenyl}-4-hydroxy-1-piperidinecarboxamide TLC: Rf 0.38 (hexane:ethyl acetate=3:7);
$^1$H-NMR (CDCl$_3$): δ 7.83-7.71 (m, 2H), 7.12-6.96 (m, 6H), 6.93 (t, 1H), 6.78 (t, 1H), 6.47 (s, 1H), 6.34 (t, 1H), 4.36 (q, 1H), 3.85-3.65 (m, 2H), 3.38-3.09 (m, 2H), 2.66 (d, 3H), 1.69-1.49 (m, 4H), 1.42-1.29 (m, 7H), 1.08 (s, 1H), 0.85 (t, 6H).

Example 14(25): N-{3-[4-(dimethylsulphamoyl)phenoxy]-5-(4-fluorophenoxy)phenyl}-4-(2-ethylbutyl)-4-hydroxy-1-piperidinecarboxamide TLC: Rf 0.46 (hexane:ethyl acetate=3:7);
$^1$H-NMR (CDCl$_3$): δ 7.77-7.66 (m, 2H), 7.12-6.98 (m, 6H), 6.95 (t, 1H), 6.79 (t, 1H), 6.41 (s, 1H), 6.34 (t, 1H), 3.85-3.70 (m, 2H), 3.36-3.19 (m, 2H), 2.70 (s, 6H), 1.68-1.50 (m, 4H), 1.44-1.28 (m, 7H), 1.04 (s, 1H), 0.85 (t, 6H).

Example 14(26): 4-(2-ethylbutyl)-N-{3-[2-fluoro-4-(methylsulphonyl)phenoxy]-5-(4-fluorophenoxy)phenyl}-4-hydroxy-1-piperidinecarboxamide TLC: Rf 0.60 (chloroform:methanol=9:1);
$^1$H-NMR (CDCl$_3$): δ 7.74 (m, 1H), 7.66 (m, 1H), 7.14 (t, 1H), 7.10-6.98 (m, 5H), 6.76 (t, 1H), 6.47 (m, 1H), 6.34 (t, 1H), 3.78 (m, 2H), 3.28 (m, 2H), 3.07 (s, 3H), 1.66-1.20 (m, 11H), 1.07 (s, 1H), 0.85 (t, 6H).

Example 14(27): 4-(2-ethylbutyl)-N-{3-(4-fluorophenoxy)-5-[3-hydroxy-4-(methylsulphonyl)phenoxy]phenyl}-4-hydroxy-1-piperidinecarboxamide TLC: Rf 0.39 (dichloromethane:methanol=10:1);
$^1$H-NMR (CDCl$_3$): δ 7.58 (d, 1H), 6.89-7.07 (m, 5H), 6.82 (br. s., 1H), 6.39-6.63 (m, 3H), 6.30 (br. s., 1H), 3.78 (d, 2H), 3.18-3.36 (m, 2H), 3.03 (br. s., 3H), 1.55-1.63 (m, 4H), 1.30-1.42 (m, 6H), 0.85 (t, 6H).

Example 14(28): N-[3-(4-carbamoyl-3-hydroxyphenoxy)-5-(4-fluorophenoxy)phenyl]-4-(2-ethylbutyl)-4-hydroxy-1-piperidinecarboxamide TLC: Rf 0.16 (hexane:ethyl acetate=2:3);
$^1$H-NMR (CDCl$_3$): δ 7.30 (d, 1H), 7.15 (dd, 1H), 6.93-7.08 (m, 5H), 6.80-6.83 (m, 1H), 6.49 (t, 1H), 6.42 (s, 1H), 6.26-6.31 (m, 1H), 3.71-3.80 (m, 2H), 3.18-3.33 (m, 2H), 1.54-1.61 (m, 4H), 1.29-1.43 (m, 7H), 0.85 (t, 6H).

Example 14(29): 4-(2-ethylbutyl)-N-{3-[4-(ethylsulphonyl)phenoxy]-5-(4-fluorophenoxy)phenyl}-4-hydroxy-1-piperidinecarboxamide TLC: Rf 0.29 (hexane:ethyl acetate=2:3);
$^1$H-NMR (CDCl$_3$): δ 7.83 (dd, 2H), 7.10 (dd, 2H), 7.01-7.05 (m, 4H), 6.95-6.97 (m, 2H), 6.76-6.79 (m, 1H), 6.37 (s, 1H), 6.33-6.36 (m, 1H), 3.77 (dt, 2H), 3.21-3.34 (m, 2H), 3.10 (q, 2H), 1.57-1.65 (m, 4H), 1.32-1.44 (m, 7H), 1.24-1.32 (m, 3H), 1.02 (s, 1H), 0.85 (t, 6H).

Example 14(30): 4-(2-ethylbutyl)-N-{3-(4-fluorophenoxy)-5-[4-(methylcarbamoyl)phenoxy]phenyl}-4-hydroxy-1-piperidinecarboxamide TLC: Rf 0.20 (hexane:ethyl acetate=3:7);

$^1$H-NMR (CDCl$_3$): δ 7.83-7.58 (m, 2H), 7.10-6.93 (m, 6H), 6.80 (d, 2H), 6.37 (s, 1H), 6.33 (t, 1H), 6.07 (br. s., 1H), 3.85-3.70 (m, 2H), 3.39-3.14 (m, 2H), 3.00 (d, 3H), 1.62-1.55 (m, 4H), 1.44-1.28 (m, 7H), 1.03 (s, 1H), 0.86 (t, 6H).

Example 15: 4-(2-ethylbutyl)-N-[3-(4-fluorophenoxy)-5-{4-[(tetrahydro-2H-pyran-2-yloxy) carbamoyl]phenoxy}phenyl]-4-hydroxy-1-piperidinecarboxamide

[C 18]

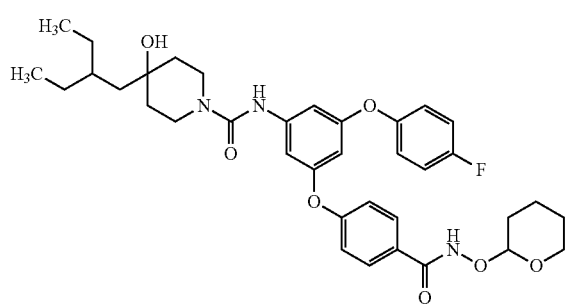

The compound prepared in Example 9(1) (20 mg) was dissolved in DMF (200 μL), added with O-(tetrahydro-2H-pyran-2-yl)hydroxylamine (4.2 mg), 1-ethyl-3-(3-dimethylaminopropyl)carbodiimide hydrochloride (EDC) (19 mg) and 1-hydroxybenzotriazole monohydrate (HOBt) (15 mg) and stirred at room temperature for 24 hours. The reaction solution was diluted with ethyl acetate and added with water and the aqueous layer was extracted with MTBE. The organic layer was combined, washed with water, a saturated sodium hydrogen carbonate aqueous solution and a saturated ammonium chloride aqueous solution and then concentrated. The resulting residue was purified by silica gel column chromatography (dichloromethane:methanol=20:1) to give the titled compound (19.6 mg) having the following physical properties.

TLC: Rf 0.42 (dichloromethane:methanol=10:1).

Examples 15(1) to 15(7)

The compounds of the following Examples were obtained by carrying out the process with the same purpose as Example 15 using the compound prepared in Example 9(1) and a corresponding amine derivative in the place of O-(tetrahydro-2H-pyran-2-yl)hydroxylamine.

Example 15(1): 4-(2-ethylbutyl)-N-{3-[4-(ethylcarbamoyl) phenoxy]-5-(4-fluorophenoxy)phenyl}-4-hydroxy-1-piperidinecarboxamide

[C 19]

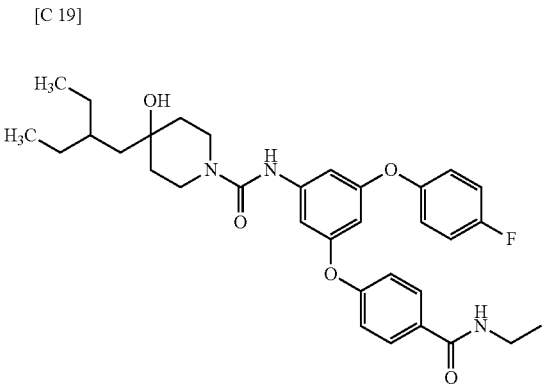 [SMILES: CCNC(=O)c1ccc(Oc2cc(NC(=O)N3CCC(O)(CC(CC)CC)CC3)cc(Oc3ccc(F)cc3)c2)cc1]

TLC: Rf 0.39 (dichloromethane:methanol=10:1);

$^1$H-NMR (CDCl$_3$): δ 7.77-7.64 (m, 2H), 7.08-6.94 (m, 6H), 6.83-6.75 (m, 2H), 6.42 (s, 1H), 6.33 (t, 1H), 6.13-5.96 (m, 1H), 3.83-3.72 (m, 2H), 3.55-3.44 (m, 2H), 3.34-3.16 (m, 2H), 1.64-1.50 (m, 4H), 1.43-1.29 (m, 7H) 1.25 (t, 3H), 1.04 (s, 1H) 0.85 (t, 6H).

Example 15(2): 4-(2-ethylbutyl)-N-{3-(4-fluorophenoxy)-5-[4-(isopropylcarbamoyl)phenoxy]phenyl}-4-hydroxy-1-piperidinecarboxamide TLC: Rf 0.42 (dichloromethane:methanol=10:1);

$^1$H-NMR (CDCl$_3$): δ 7.71 (d, 2H), 7.07-6.97 (m, 6H), 6.83-6.78 (m, 2H), 6.37 (d, 1H), 6.32 (t, 1H), 5.92-5.78 (m, 1H), 4.36-4.14 (m, 1H), 3.83-3.72 (m, 2H), 3.38-3.13 (m, 2H), 1.66-1.49 (m, 4H), 1.45-1.30 (m, 7H), 1.26 (d, 6H), 1.03 (s, 1H), 0.85 (t, 6H).

Example 15(3): 4-(2-ethylbutyl)-N-{3-(4-fluorophenoxy)-5-[4-(4-morpholinylcarbonyl)phenoxy]phenyl}-4-hydroxy-1-piperidinecarboxamide TLC: Rf 0.42 (dichloromethane:methanol=1:2);

$^1$H-NMR (CDCl$_3$): δ 7.45-7.34 (m, 2H), 7.08-6.97 (m, 6H), 6.83 (t, 1H), 6.74 (t, 1H), 6.39 (s, 1H), 6.33 (t, 1H) 3.89-3.49 (m, 10H), 3.34-3.17 (m, 2H), 1.62-1.52 (m, 4H), 1.45-1.27 (m, 7H), 1.05 (s, 1H), 0.85 (t, 6H).

Example 15(4): 4-(2-ethylbutyl)-N-[3-(4-fluorophenoxy)-5-{4-[(3-hydroxy-1-azetidinyl)carbonyl]phenoxy}phenyl]-4-hydroxy-1-piperidinecarboxamide TLC: Rf 0.25 (dichloromethane:methanol=10:1);

$^1$H-NMR (CDCl$_3$): δ 7.58-7.49 (m, 2H), 7.08-6.95 (m, 6H), 6.89 (t, 1H), 6.83 (d, 1H), 6.74 (t, 1H), 6.32 (t, 1H), 4.78-4.52 (m, 1H), 4.39 (br. s., 2H), 4.24-3.83 (m, 2H), 3.85-3.70 (m, 2H), 3.34-3.01 (m, 2H), 1.61 (s, 1H), 1.60-1.52 (m, 4H), 1.45-1.27 (m, 7H), 1.24 (d, 1H), 0.83 (t, 6H).

Example 15(5): 4-(2-ethylbutyl)-N-[3-(4-fluorophenoxy)-5-{4-[(3-hydroxy-1-pyrrolidinyl)carbonyl]phenoxy}phenyl]-4-hydroxy-1-piperidinecarboxamide TLC: Rf 0.23 (dichloromethane:methanol=10:1);

¹H-NMR (CDCl₃): δ 7.55-7.40 (m, 2H), 7.10-7.00 (m, 6H), 6.99-6.92 (m, 1H), 6.90-6.79 (m, 1H), 6.65 (t, 1H), 6.32 (t, 1H), 4.65-4.35 (m, 1H), 3.90-3.68 (m, 4H), 3.67-3.34 (m, 2H), 3.30-3.05 (m, 2H), 2.28-2.18 (m, 1H), 2.15-1.92 (m, 2H), 1.64-1.51 (m, 4H), 1.42-1.25 (m, 7H), 1.16 (br. s., 1H) 0.84 (t, 6H).

Example 15(6): 4-(2-ethylbutyl)-N-[3-(4-fluorophenoxy)-5-{4-[(4-hydroxy-1-piperidinyl)carbonyl]phenoxy}phenyl]-4-hydroxy-1-piperidinecarboxamide

[C 20]

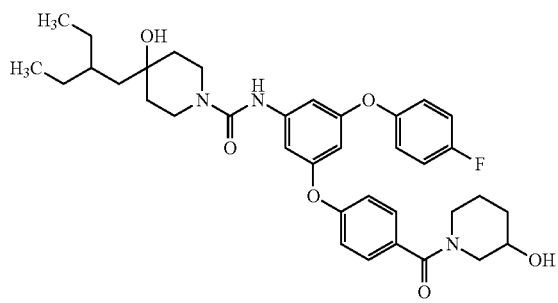

TLC: Rf 0.30 (dichloromethane:methanol=10:1);

¹H-NMR (CDCl₃): δ 7.39-7.31 (m, 2H), 7.06-6.96 (m, 6H), 6.93 (t, 1H), 6.79-6.70 (m, 1H), 6.65 (t, 1H), 6.32 (t, 1H), 4.40-3.90 (m, 3H), 3.85-3.70 (m, 2H), 3.41-3.07 (m, 4H), 2.10-1.80 (m, 2H), 1.80-1.70 (m, 1H), 1.66-1.45 (m, 6H), 1.43-1.24 (m, 7H), 1.17 (br. s., 1H), 0.84 (t, 6H).

Example 15(7): 4-(2-ethylbutyl)-N-[3-(4-fluorophenoxy)-5-{4-[(3-hydroxy-1-piperidinyl)carbonyl]phenoxy}phenyl]-4-hydroxy-1-piperidinecarboxamide TLC: Rf 0.35 (dichloromethane:methanol=10:1);

¹H-NMR (CDCl₃): δ 7.36 (d, 2H), 7.06-6.94 (m, 6H), 6.93-6.72 (m, 3H), 6.64 (s, 1H), 6.32 (t, 1H), 4.05-3.50 (m, 4H), 3.49-3.10 (m, 5H), 2.45-2.25 (m, 1H), 2.00-1.75 (m, 2H), 1.70-1.40 (m, 6H), 1.40-1.20 (m, 7H), 1.20 (d, 1H), 0.84 (t, 6H).

Example 16: 4-(2-ethylbutyl)-N-{3-(4-fluorophenoxy)-5-[4-(hydroxycarbamoyl)phenoxy]phenyl}-4-hydroxy-1-piperidinecarboxamide

[C 21]

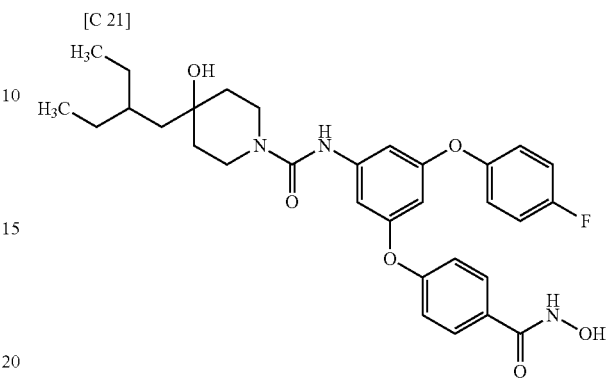

The compound prepared in Example 15 (19 mg) was dissolved in ethyl acetate (0.5 mL), added with a hydrochloric acid/ethyl acetate solution (4 mol/L, 0.1 mL) and stirred at room temperature for 20 minutes. The reaction solution was concentrated before purification on preparative TLC (dichloromethane:methanol=10:1) to give the titled compound (5.1 mg) having the following physical properties.

TLC: Rf 0.23 (dichloromethane:methanol=10:1);

¹H-NMR (CD₃OD): δ 7.75 (d, 2H), 7.15-6.99 (m, 6H), 6.91 (t, 1H), 6.87 (t, 1H), 6.27 (t, 1H), 3.88-3.70 (m, 2H), 3.28-3.14 (m, 2H), 1.68-1.48 (m, 4H), 1.44-1.26 (m, 7H), 0.87 (t, 6H).

Example 17: 2-methyl-2-propanyl-3-hydroxy-3-isobutyl-1-azetidinecarboxylate

Under an argon atmosphere, to a 100-mL three-neck flask was added a 0.6 M lanthanum chloride/2 lithium chloride (LaCl₃/2LiCl) solution in THF (31.0 mL) which was added with a 2.0 M isobutylmagnesium chloride solution in THF (6.9 mL) while cooling to 0° C. The mixture was stirred at 0° C. for 3 hours before addition of 2-methyl-2-propanyl-3-oxo-1-azetidinecarboxylate (1.6 g) dissolved in THF (4.0 mL) at 0° C. The reaction solution was stirred from 0° C. to room temperature over 15 hours before addition of a 5% acetic acid aqueous solution (30 mL) and extraction twice with ethyl acetate. The organic layer was washed with a saturated sodium chloride solution and dried over anhydrous sodium sulphate and the solvent was distilled off to give a brown oily substance (3.2 g). The substance was purified by column chromatography (medium pressure preparative liquid chromatography W-prep 2XY from Yamazen Corporation (column: main column 2L, injection column L; hexane:ethyl acetate 9:1→7:3)) to give the titled compound (2.0 g) having the following physical properties.

TLC: Rf 0.53 (hexane:ethyl acetate=2:1).

Example 18: 3-isobutyl-3-azetidinol

To a 200-mL pear-shaped evaporating flask were added the compound prepared in Example 17 (2.0 g) and methanol (9 mL) and then a 4 N hydrochloric acid/ethyl acetate solution (11 mL) at 0° C. The mixture was stirred at room temperature for 7 hours, again cooled to 0° C., added with a 5 N sodium hydroxide aqueous solution (43.5 mL) and extracted twice with methylene chloride. The organic layer was dried over anhydrous sodium sulphate and the solvent was distilled off under reduced pressure to give the titled compound (973.5 mg) having the following physical properties. The resulting titled compound was directly used for the next reaction without purification.

TLC: Rf 0.69 (ethyl acetate:methanol=3:1).

Example 19: 2-{4-[3-(4-fluorophenoxy)-5-{[(3-hydroxy-3-isobutyl-1-azetidinyl)carbonyl]amino}phenoxy]phenyl}-2-methylpropanoic Acid

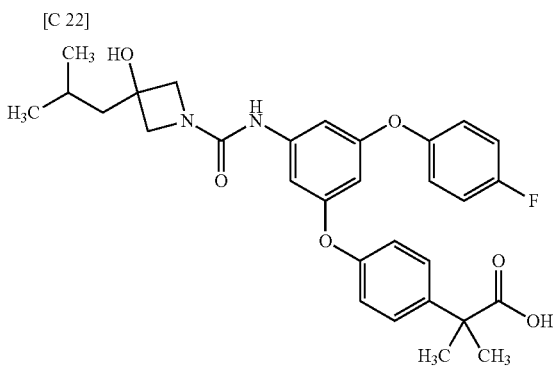

The titled compound (41 mg) having the following physical properties was obtained by carrying out the processes with the same purposes as Example 8→Example 9 using the compound prepared in Example 18 (64.6 mg) and the compound prepared in Example 7 (342.5 mg).

TLC: Rf 0.15 (dichloromethane:ethanol=20:1);
$^1$H-NMR (CDCl$_3$): δ 7.31 (d, 2H), 6.87-7.11 (m, 6H), 6.76 (s, 1H), 6.66 (s, 1H), 6.21-6.37 (m, 2H), 3.70-4.01 (m, 4H), 2.55 (br. s., 2H), 1.72-1.97 (m, 1H), 1.61 (d, 2H), 1.56 (s, 6H), 0.91 (d, 6H).

Examples 19(1) to 19(9)

The compounds of the following Examples were obtained by carrying out the process with the same purpose as Example 19 using a corresponding cyclic amine derivative in the place of the compound prepared in Example 18 and the compound prepared in Example 7.

Example 19(1): 2-{4-[3-(4-fluorophenoxy)-5-{[(3-hydroxy-3-isobutyl-1-pyrrolidinyl)carbonyl]amino}phenoxy]phenyl}-2-methylpropanoic Acid TLC: Rf 0.13 (dichloromethane:ethanol=20:1);
$^1$H-NMR (CDCl$_3$): δ 7.29-7.39 (m, 2H), 6.89-7.07 (m, 6H), 6.84 (t, 1H), 6.71 (t, 1H), 6.30 (t, 1H), 6.20 (s, 1H), 3.39-3.66 (m, 3H), 3.26 (d, 1H), 2.52 (br. s., 2H), 1.73-2.06 (m, 3H), 1.44-1.68 (m, 8H), 0.97 (dd, 6H).

Example 19(2): 2-{4-[3-({[(3R,4S)-3-fluoro-4-hydroxy-4-isobutyl-1-piperidinyl]carbonyl}amino)-5-(4-fluorophenoxy)phenoxy]phenyl}-2-methylpropanoic Acid TLC: Rf 0.31 (dichloromethane:ethanol=20:1);
$^1$H-NMR (CDCl$_3$): δ 7.29-7.43 (m, 2H), 6.90-7.10 (m, 6H), 6.77 (t, 1H), 6.65 (t, 1H), 6.43 (s, 1H), 6.31 (t, 1H), 4.20-4.48 (m, 1H), 3.94 (ddd, 1H), 3.54 (d, 1H), 3.19-3.42 (m, 2H), 1.99-2.25 (m, 2H), 1.73-1.97 (m, 2H), 1.34-1.69 (m, 9H), 0.98 (dd, 6H).

Example 19(3): 2-{4-[3-(4-fluorophenoxy)-5-{[(3-hydroxy-3-isopropyl-1-pyrrolidinyl) carbonyl]amino}phenoxy]phenyl}-2-methylpropanoic Acid TLC: Rf 0.45 (dichloromethane:methanol=10:1);
$^1$H-NMR (CD$_3$OD): δ 7.42-7.34 (m, 2H), 7.14-6.94 (m, 6H), 6.93-6.90 (m, 1H), 6.87 (t, 1H), 6.21 (t, 1H), 3.57 (dd, 2H), 3.48-3.32 (m, 2H), 2.04-1.68 (m, 3H), 1.55 (s, 6H), 0.98 (d, 6H).

Example 19(4): 2-{4-[3-{[(3-cyclopentyl-3-hydroxy-1-pyrrolidinyl)carbonyl]amino}-5-(4-fluorophenoxy)phenoxy]phenyl}-2-methylpropanoic Acid TLC: Rf 0.47 (dichloromethane:methanol=10:1);
$^1$H-NMR (CD$_3$OD): δ 7.41-7.34 (m, 2H), 7.15-6.95 (m, 6H), 6.94-6.91 (m, 1H), 6.87 (t, 1H), 6.21 (t, 1H), 3.61-3.50 (m, 2H), 3.45-3.32 (m, 2H), 2.15-1.97 (m, 1H), 1.89 (t, 2H), 1.55 (s, 6H), 1.78-1.40 (m, 8H).

Example 19(5): 2-{4-[3-{[(3-cyclohexyl-3-hydroxy-1-pyrrolidinyl)carbonyl]amino}-5-(4-fluorophenoxy)phenoxy]phenyl}-2-methylpropanoic Acid TLC: Rf 0.48 (dichloromethane:methanol=10:1);
$^1$H-NMR (CD$_3$OD): δ 7.41-7.35 (m, 2H), 7.13-6.94 (m, 6H), 6.93-6.90 (m, 1H), 6.87 (t, 1H), 6.21 (t, 1H), 3.60-3.50 (m, 2H), 3.47-3.32 (m, 2H), 1.98-1.61 (m, 7H), 1.55 (s, 6H), 1.49-1.09 (m, 6H).

Example 19(6): 1-{4-[3-{[(3-cyclopentyl-3-hydroxy-1-pyrrolidinyl)carbonyl]amino}-5-(4-fluorophenoxy)phenoxy]phenyl}cyclopropanecarboxylic Acid TLC: Rf 0.49 (dichloromethane:methanol=10:1);
$^1$H-NMR (CDCl$_3$): δ 7.32-7.26 (m, 2H), 7.07-6.97 (m, 4H), 6.96-6.91 (m, 2H), 6.90 (t, 1H), 6.70 (t, 1H), 6.32 (t, 1H), 6.20 (s, 1H), 3.64-3.47 (m, 2H), 3.43 (d, 1H), 3.30 (d, 1H), 2.04-1.95 (m, 1H), 1.93-1.84 (m, 2H), 1.77-1.49 (m, 8H), 1.46-1.33 (m, 2H), 1.27-1.19 (m, 2H).

Example 19(7): 1-{4-[3-{[(3-cyclohexyl-3-hydroxy-1-pyrrolidinyl)carbonyl]amino}-5-(4-fluorophenoxy)phenoxy]phenyl}cyclopropanecarboxylic Acid TLC: Rf 0.49 (dichloromethane:methanol=10:1);
$^1$H-NMR (CDCl$_3$): δ 7.31-7.26 (m, 2H), 7.06-6.97 (m, 4H), 6.96-6.91 (m, 2H), 6.90 (t, 1H), 6.70 (t, 1H), 6.32 (t, 1H), 6.21 (s, 1H), 3.64-3.50 (m, 2H), 3.46 (d, 1H), 3.27 (d, 1H), 1.99-1.55 (m, 9H), 1.47-1.31 (m, 2H), 1.30-1.07 (m, 6H).

Example 19(8): 2-{4-[3-{[(3-cyclohexyl-3-hydroxy-1-pyrrolidinyl)carbonyl]amino}-5-(4-fluorophenoxy)phenoxy}-2-methylpropanoic Acid TLC: Rf 0.28 (dichloromethane:methanol=10:1);
$^1$H-NMR (CDCl$_3$): δ 7.05-6.94 (m, 4H), 6.92-6.86 (m, 4H), 6.75 (t, 1H), 6.60 (t, 1H), 6.30-6.25 (m, 2H), 3.57-3.47 (m, 2H), 3.43 (d, 1H), 3.25 (d, 1H), 1.96-1.85 (m, 1H), 1.85-1.66 (m, 6H), 1.58 (s, 6H), 1.45-1.33 (m, 1H), 1.24-1.11 (m, 5H).

Example 19(9): 1-{4-[3-{[(3-cyclohexyl-3-hydroxy-1-pyrrolidinyl)carbonyl]amino}-5-(4-fluorophenoxy)phenoxy]phenoxy}cyclopropanecarboxylic Acid TLC: Rf 0.28 (dichloromethane:methanol=10:1);
$^1$H-NMR (CDCl$_3$): δ 7.06-6.92 (m, 4H), 6.89-6.78 (m, 4H), 6.63-6.51 (m, 3H), 6.29 (t, 1H), 3.50-3.29 (m, 3H), 3.15 (d, 1H), 1.89-1.59 (m, 6H), 1.58-1.48 (m, 3H), 1.35-1.03 (m, 8H).

Example 20: Methyl 4-{[3-(4-fluorophenoxy)-5-nitrophenyl]thio}benzoate

Under an argon atmosphere, the compound prepared in Example 10 (6.01 g) was dissolved in DMA (60 mL), potassium carbonate (7.62 g) and 4-carbomethoxybenzene thiol (2.80 g) were added thereto and the reaction mixture was stirred at 75° C. for 3 hours. The reaction mixture was cooled to room temperature, poured to water, extracted with MTBE, sequentially washed with water and a saturated sodium chloride solution, dried over anhydrous sodium sulphate and concentrated under reduced pressure. The concentrate was purified by silica gel column chromatography (hexane:ethyl acetate=9:1→4:1) to give the titled compound (2.28 g) having the following physical properties.
TLC: Rf 0.59 (hexane:ethyl acetate=4:1).

Example 21: Methyl 4-{[3-amino-5-(4-fluorophenoxy)phenyl]thio}benzoate

The compound prepared in Example 20 (1.12 g) and acetic acid (11.2 mL) were dissolved in water (0.86 mL), added with iron (777 mg) with small portions and the reaction was allowed to proceed at 90° C. for 1.5 hours. The reaction solution was cooled to room temperature, added with ethyl acetate (30 mL) and stirred for 20 minutes. Celite (trade name) was used for filtration and the filtrate was concentrated under reduced pressure after addition of toluene. The resulting residue was added with ethyl acetate, washed with water, a saturated sodium hydrogen carbonate solution and a saturated sodium chloride solution, dried over anhydrous sodium sulphate and concentrated. The resulting residue was purified by silica gel column chromatography (hexane:ethyl acetate=9:1→1:1) to give the titled compound (830 mg) having the following physical properties.
TLC: Rf 0.17 (hexane:ethyl acetate=4:1).

Example 22: 4-{[3-(4-fluorophenoxy)-5-({[4-(4-fluorophenyl)-4-hydroxy-1-piperidinyl]carbonyl}amino)phenyl]thio}benzoic acid The titled compound (12.0 g) having the following physical properties was obtained by carrying out the processes with the same purposes as Example 7→Example 8→Example 9 using the compound prepared in Example 21; 2,2,2-trichloroethyl chloroformate; and 4-(4-fluorophenyl)-4-piperidinol in the place of 4-isobutyl-4-piperidinol.
TLC: Rf 0.52 (chloroform:methanol:ethanol=9:1:0.1);
$^1$H-NMR (CD$_3$OD): δ 1.73, 2.00, 3.32-3.44, 4.03, 6.62, 6.95-7.18, 7.24-7.36, 7.46-7.55, 7.86-7.99.

Example 23: tert-butyl 4-hydroxy-4-isobutyl-2-methylpiperidine-1-carboxylate Under an argon atmosphere, in a 50-mL pear-shaped evaporating flask was weighed a solution of lanthanum chloride lithium chloride complex in THF (15.6 mL) and cooled to 0° C. To the solution was added dropwise a solution of isobutylmagnesium chloride in THF (3.5 mL) and stirred at 0° C. for 3 hours. A solution of tert-butyl 2-methyl-4-oxopiperidine-1-carboxylate (1 g) in THF (2.0 mL) was further added dropwise. The reaction solution was stirred at 0° C. for 1 hour, heated to 25° C., poured to hydrochloric acid and extracted with ethyl acetate. The organic layer was washed with water and a saturated sodium chloride solution and dried over anhydrous magnesium sulphate. The filtrate was concentrated and the resulting residue was purified by silica gel chromatography (hexane:ethyl acetate=9:1→3:1) to give the titled compound (450 mg) having the following physical properties.
TLC: Rf 0.51 (hexane:ethyl acetate=3:1).

Example 24: 2-methyl-4-isobutyl-4-hydroxypiperidine Hydrochloride

In a 100-mL pear-shaped evaporating flask was weighed the compound prepared in Example 23 (440 mg) and added a solution of hydrogen chloride (4 mol/L) in 1,4-dioxane (5.0 mL). The reaction solution was stirred at 25° C. for 30 minutes before concentration to give the titled compound (336 mg) having the following physical properties.
$^1$H-NMR (CD$_3$OD): δ 1.01 (d, 6H), 1.34 (d, 3H), 1.50-1.58 (m, 3H), 1.67-1.88 (m, 2H), 1.92-2.02 (m, 2H), 3.03 (dt, 1H), 3.27-3.38 (m, 2H).

Example 25: 2-{4-[3-(4-fluorophenoxy)-5-{[(4-hydroxy-4-isobutyl-2-methyl-1-piperidinyl)carbonyl]amino}phenoxy]phenyl}-2-methylpropanoic Acid The titled compound (60 mg) having the following physical properties was obtained by carrying out the processes with the same purposes as Example 8→Example 9 using the compound prepared in Example 24 (48 mg) and the compound prepared in Example 7 (100 mg).
TLC: Rf 0.33 (chloroform:methanol=19:1);
$^1$H-NMR (CDCl$_3$): δ 0.97 (dd, 6H), 1.36 (t, 2H), 1.38 (d, 3H), 1.47-1.75 (m, 10H), 1.77-1.89 (m, 1H), 3.36 (dt, 1H), 3.71-3.79 (m, 1H), 4.26-4.35 (m, 1H), 6.29 (t, 1H), 6.38 (s, 1H), 6.69 (t, 1H), 6.81 (t, 1H), 6.96-7.02 (m, 6H), 7.35 (d, 2H).

Example 26: Ethyl 2-(benzhydrylideneamino)-2-[4-{3-(4-fluorophenoxy)-5-nitrophenoxy}phenyl]acetate To the compound prepared in Example 11 (1.0 g) were added ethyl[(diphenylmethylene)amino]acetate (652 mg) and potassium phosphate (1.41 g) and suspended in toluene (7.4 mL). The reaction system was degassed, purged with argon, added with Pd(t-Bu$_3$P)$_2$ (23 mg), degassed again and purged with argon. The reaction solution was stirred at 100° C. for 17 hours, cooled to 0° C., adjusted to pH 7 by addition of water and 1 N hydrochloric acid and extracted with ethyl acetate. The organic layer was sequentially washed with water and a saturated sodium chloride solution and dried over anhydrous magnesium sulphate. The resulting residue obtained after concentration was purified by silica gel chromatography (hexane:ethyl acetate=100:0→9:1) to give the titled compound (456 mg) having the following physical properties.

TLC: Rf 0.36 (hexane:ethyl acetate=3:1).

Example 27: Ethyl amino{4-[3-(4-fluorophenoxy)-5-nitrophenoxy]phenyl}acetate

The compound prepared in Example 26 (356 mg) was dissolved in ethanol (4 mL) and DME (3 mL), added with 1 N hydrochloric acid (1.8 mL) and stirred at room temperature for 15 hours. The concentrated reaction solution was cooled to 0° C., neutralized with saturated aqueous sodium bicarbonate and extracted with ethyl acetate. The organic layer was sequentially washed with water and a saturated sodium chloride solution and dried over anhydrous magnesium sulphate. The resulting residue obtained after concentration was purified by silica gel chromatography (hexane:ethyl acetate=80:20→60:40) to obtain the titled compound (253 mg) having the following physical properties.

TLC: Rf 0.28 (hexane:ethyl acetate=1:1).

Example 28: Ethyl 2-(benzyloxycarbonylamino)-2-{4-[3-(4-fluorophenoxy)-5-nitrophenoxy]phenyl}acetate The compound prepared in Example 27 (253 mg) was dissolved in ethyl acetate (2.5 mL) and added with sodium hydrogen carbonate (100 mg) and benzyl chloroformate (112 mg) at 0° C. The reaction solution was stirred at room temperature for 13 hours, added with water and extracted with ethyl acetate. The organic layer was sequentially washed with water and a saturated sodium chloride solution and dried over anhydrous magnesium sulphate. The resulting residue obtained after concentration was purified by silica gel chromatography (hexane:ethyl acetate=100:0→85:15) to give the titled compound (234 mg) having the following physical properties.

TLC: Rf 0.32 (hexane:ethyl acetate=5:1).

Example 29: Ethyl 2-{4-[3-amino-5-(4-fluorophenoxy)phenoxy]phenyl}-2-(benzyloxycarbonylamino)acetate To the compound prepared in Example 28 (253 mg) were added iron (166 mg), zinc (194 mg), ammonium chloride (32 mg), water (0.2 mL) and ethanol (1.5 mL) and stirred at 70° C. for 3 hours. The reaction solution was cooled to room temperature, diluted with water and ethyl acetate and filtered with celite. The resulting filtrate was added with saturated aqueous sodium bicarbonate and extracted with ethyl acetate. The organic layer was sequentially washed with water and a saturated sodium chloride solution and dried over anhydrous magnesium sulphate to give the titled compound (278 mg) having the following physical properties.

TLC: Rf 0.17 (hexane:ethyl acetate=3:1).

Example 30: Amino{4-[3-(4-fluorophenoxy)-5-{[(4-hydroxy-4-isobutyl-1-piperidinyl)carbonyl]amino}phenoxy]phenyl}acetic Acid The titled compound (28.4 mg) having the following physical properties was obtained by carrying out the processes with the same purposes as Example 7→Example 8→Example 9→Example 6 using the compound prepared in Example 29 and 4-isobutyl-4-piperidinol.

TLC: Rf 0.15 (dichloromethane:methanol:aqueous ammonia=160:30:1);

$^1$H-NMR (CD$_3$OD): δ 7.45 (d, 2H), 7.13-6.97 (m, 6H), 6.83 (dt, 2H), 6.20 (t, 1H), 4.50 (s, 1H), 3.80 (d, 2H), 3.29-3.16 (m, 2H), 1.92-1.80 (m, 1H), 1.67-1.45 (m, 4H), 1.39 (d, 2H), 0.97 (d, 6H).

Example 31: Benzyl 3-(diethylcarbamoyl)-1-pyrrolidinecarboxylate

Under an argon atmosphere, 1-[(benzyloxy)carbonyl]-3-pyrrolidinecarboxylic acid (500 mg) was dissolved in DMF (5 mL), added with N,N-diethylamine (0.293 g), further with EDC (769 mg) and HOBt (542 mg) and stirred at room temperature for 72 hours. The reaction solution was diluted with ethyl acetate, sequentially washed with 1 N hydrochloric acid, a 1 N sodium hydroxide aqueous solution, water and a saturated sodium chloride solution and dried over anhydrous magnesium sulphate before distillation of the solvent. The resulting residue was purified by silica gel chromatography (hexane:ethyl acetate=95:5→0:1) to give the titled compound (556 mg) having the following physical properties.

$^1$H-NMR (CDCl$_3$): δ 7.38-7.25 (m, 5H), 5.13 (s, 2H), 3.75-3.04 (m, 8H), 2.20 (m, 2H), 1.20 (t, 3H), 1.11 (t, 3H).

Example 32: N,N-diethyl-3-pyrrolidinecarboxamide

The compound prepared in Example 31 (556 mg) was dissolved in ethanol (10 mL) and ethyl acetate (20 mL) and added with 5% palladium carbon (100 mg) and the reaction solution was stirred under a hydrogen atmosphere at room temperature for 8 hours. The reaction solution was filtered with celite and the solvent was distilled off to give the titled compound having the following physical properties. The resulting titled compound was used for the next reaction without further purification.

$^1$H-NMR (CDCl$_3$): δ 3.50-2.74 (m, 8H), 1.97 (m, 2H), 1.20 (t, 3H), 1.11 (t, 3H).

Example 33: 2-{4-[3-({[3-(diethylcarbamoyl)-1-pyrrolidinyl]carbonyl}amino)-5-(4-fluorophenoxy)phenoxy]phenyl}-2-methylpropanoic Acid The titled compound (59.4 g) having the following physical properties was obtained by carrying out the processes with the same purposes as Example 8→Example 9 using the compound prepared in Example 32 (29.8 mg) and the compound prepared in Example 7 (100 mg).

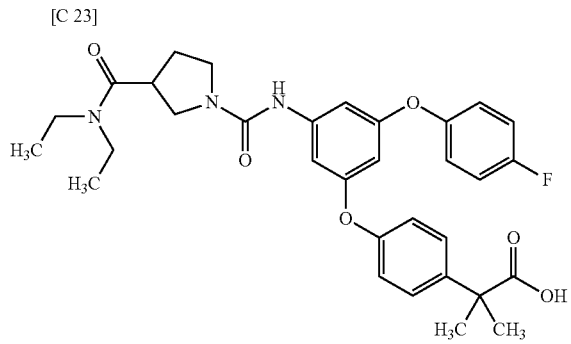

[C 23]

TLC: Rf 0.60 (chloroform:methanol=9:1);

$^1$H-NMR (CDCl$_3$): δ 7.31 (m, 2H), 7.98-6.88 (m, 7H), 6.68 (m, 1H), 6.44 (m, 1H), 6.30 (m, 1H), 3.74-3.12 (m, 8H), 2.25-2.00 (m, 2H), 1.55 (s, 6H), 1.19 (t, 3H), 1.09 (t, 3H).

Example 33(1): 2-{4-[3-(4-fluorophenoxy)-5-({[3-(isopropylcarbamoyl)-1-pyrrolidinyl]carbonyl}amino)phenoxy]phenyl}-2-methylpropanoic Acid The titled compound (63.6 mg) having the following physical properties was obtained by carrying out the process with the same purpose as Example 33 using the compound prepared in Example 7 (100 mg) and a corresponding pyrrolidine derivative (27.4 mg) in the place of the compound prepared in Example 32.

TLC: Rf 0.54 (chloroform:methanol=9:1);

$^1$H-NMR (CDCl$_3$): δ 7.31 (m, 2H), 7.04-6.80 (m, 7H), 6.68 (m, 1H), 6.48 (m, 1H), 6.30 (m, 1H), 5.64 (d, 1H), 4.03 (m, 1H), 3.62-3.50 (m, 3H), 3.33 (m, 1H), 2.79 (m, 1H), 2.09 (m, 2H), 1.56 (s, 6H), 1.11 (m, 6H).

Example 34: Methyl 3,5-dinitrobenzoate

In methanol (100 mL) was dissolved 3,5-dinitrobenzoyl chloride and diisopropylethylamine (4.53 mL) was added thereto while cooling with ice. The reaction solution was stirred for 1 hour and then the solvent was distilled off. The resulting substance was diluted with ethyl acetate, sequentially washed with water and a saturated sodium chloride solution and dried over anhydrous magnesium sulphate before distillation of the solvent to give the titled compound (4.73 g) having the following physical properties.

TLC: Rf 0.31 (hexane:ethyl acetate=5:1).

Example 35: Methyl 3-(4-fluorophenoxy)-5-nitrobenzoate

The compound prepared in Example 34 (4.73 g) was dissolved in DMF (40 mL), added with 4-fluorophenol (2.34 g) and potassium phosphate (5.32 g) and stirred overnight at 80° C. The reaction solution was diluted with ethyl acetate, sequentially washed with water and a saturated sodium chloride solution and dried over anhydrous magnesium sulphate before distillation of the solvent. The resulting residue was purified by silica gel chromatography (hexane:ethyl acetate=9:1→1:1) to give the titled compound (4.81 g) having the following physical properties.

TLC: Rf 0.47 (hexane:ethyl acetate=5:1).

Example 36: Methyl 3-(4-fluorophenoxy)-5-{[(4-hydroxy-4-isobutyl-1-piperidinyl)carbonyl]amino}benzoate The titled compound (495 mg) having the following physical properties was obtained by carrying out the processes with the same purposes as Example 6→Example 7→Example 8 using the compound prepared in Example 35 and 4-isobutyl-4-piperidinol.

$^1$H-NMR (CDCl$_3$): δ 7.40-7.20 (m, 7H), 5.13 (s, 2H), 3.94 (m, 2H), 3.22 (m, 2H), 2.46 (m, 1H), 1.83 (m, 2H), 1.57 (m, 6H).

Example 37: 3-(4-fluorophenoxy)-5-{[(4-hydroxy-4-isobutyl-1-piperidinyl)carbonyl]amino}benzoic Acid The compound prepared in Example 36 (495 mg) was dissolved in methanol (5 mL), added with a 2 N sodium hydroxide aqueous solution (1.11 mL) and stirred at 45° C. for 2 hours. The reaction solution was neutralized with the equivalent amount of hydrochloric acid before distillation of the solvent, dilution with ethanol, filtration and desalting to give the titled compound (490 mg). The resulting titled compound was used for the next reaction without further purification.

Example 38: 2-(4-{[3-(4-fluorophenoxy)-5-{[(4-hydroxy-4-isobutyl-1-piperidinyl)carbonyl]amino}benzoyl]oxy}phenyl)-2-methylpropanoic Acid

[C 24]

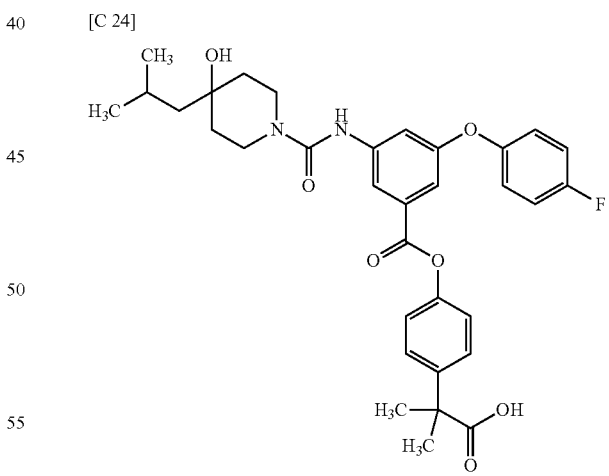

Under an argon atmosphere, the compound prepared in Example 37 (75 mg) was dissolved in DMF (1 mL), added with EDC (55.5 mg), HOBt (39.1 mg), diisopropylethylamine (0.05 mL) and benzyl 2-(4-hydroxyphenyl)-2-methylpropanoate (56.5 mg) and stirred overnight at room temperature. The reaction solution was diluted with ethyl acetate, sequentially washed with water and a saturated sodium chloride solution and dried over anhydrous magnesium sulphate before distillation of the solvent. The resulting residue was dissolved in methanol (1 mL) and ethyl acetate (1 mL), added with 5% palladium carbon (50 mg) and stirred at room temperature for 2 hours in a hydrogen atmosphere. The reaction solution was filtered with celite and the solvent was distilled off. The resulting residue was purified by thin layer chromatography (chloroform:methanol=5:1) to give the titled compound (59.1 mg) having the following physical properties.

TLC: Rf 0.62 (chloroform:methanol=5:1);
$^1$H-NMR (CDCl$_3$) δ 7.58 (m, 2H), 7.32 (m, 3H), 7.18-6.90 (m, 6H), 3.79 (m, 2H), 3.24 (m, 2H), 1.80 (m, 1H), 1.70-1.45 (m, 4H), 1.52 (s, 6H), 1.37 (d, 2H), 0.95 (d, 6H).

Example 39: 4-cyclopropyl-N-[3-(4-fluorophenoxy)-5-(hydroxymethyl)phenyl]-4-hydroxy-1-piperidinecarboxamide Under an argon atmosphere, methyl 3-{[(4-cyclopropyl-4-hydroxy-1-piperidinyl)carbonyl]amino}-5-(4-fluorophenoxy)benzoate (201 mg) which was obtained with the same procedure as Example 36 using the compound prepared in Example 35 and 4-cyclopropyl-4-piperidinol in the place of 4-isobutyl-4-piperidinol was dissolved in THF (10 mL), added with diisobutylaluminium hydride (1.407 mL, 1.0 M, a solution in toluene) and stirred at 0° C. for 1.5 hours. The reaction solution was added with a sodium sulphate aqueous solution and filtered with celite and the solvent was distilled off. The reaction solution was further diluted with ethyl acetate, sequentially washed with water and a saturated sodium chloride solution and dried over anhydrous magnesium sulphate before distillation of the solvent. The resulting residue was purified by silica gel chromatography (hexane:ethyl acetate=95:5→0:1) to give the titled compound (161 mg) having the following physical properties.

$^1$H-NMR (CDCl$_3$): δ 7.06 (m, 1H), 7.00-6.88 (m, 5H), 6.79 (m, 1H), 6.58 (m, 1H), 4.52 (s, 2H), 3.78 (m, 2H), 3.18 (m, 2H), 1.68-1.44 (m, 4H), 0.89 (m, 1H), 0.39-0.32 (m, 4H).

Example 40: 2-(4-{[3-{[(4-cyclopropyl-4-hydroxy-1-piperidinyl)carbonyl]amino}-5-(4-fluorophenoxy)benzyl]oxy}phenyl)-2-methylpropanoic Acid Under an argon atmosphere, the compound prepared in Example 39 (153 mg) was dissolved in THF (12 mL), added with the compound prepared in Example 3 (89.2 mg), diisopropyl azodicarboxylate (0.114 mL) and triphenylphosphine (110 mg) and stirred overnight at room temperature. The reaction solution was diluted with ethyl acetate, sequentially washed with water and a saturated sodium chloride solution and dried over anhydrous magnesium sulphate before distillation of the solvent. The resulting residue was purified by silica gel chromatography (hexane:ethyl acetate=9:1→0:1). The resulting product was further dissolved in methanol (2 mL), added with a 2 N sodium hydroxide aqueous solution (0.575 mL) and stirred at 45° C. for 2 hours. The reaction solution was neutralized with the equivalent amount of hydrochloric acid before concentration and the resulting residue was purified by thin layer chromatography (chloroform:methanol=5:1) to give the titled compound (99.0 mg) having the following physical properties.

TLC: Rf 0.58 (chloroform:methanol=5:1);
$^1$H-NMR (CDCl$_3$): δ 7.30-6.70 (m, 10H), 6.67 (m, 1H), 6.51 (s, 1H), 4.96 (s, 2H), 3.80 (m, 2H), 3.24 (m, 2H), 1.70-1.48 (m, 4H), 1.56 (s, 6H), 0.93 (m, 1H), 0.44-0.32 (m, 4H).

Example 41: N-[3-(4-fluorophenoxy)-5-hydroxyphenyl]-4-hydroxy-4-isobutyl-1-piperidinecarboxamide The titled compound having the following physical properties was obtained by carrying out the processes with the same purposes as Example 4→Example 5→Example 6→Example 7→Example 8 using 1,3-difluoro-5-nitrobenzene, phenylmethanol, 4-fluorophenol and 4-isobutyl-4-piperidinol.

TLC: Rf 0.52 (hexane:ethyl acetate=1:2).

Example 42: Ethyl {4-[3-(4-fluorophenoxy)-5-{[(4-hydroxy-4-isobutyl-1-piperidinyl)carbonyl]amino}phenoxy]phenyl}(oxo)acetate The compound prepared in Example 41 (100 mg) and ethyl 2-(4-fluorophenyl)-2-oxoacetate (73 mg) were dissolved in DMF (0.7 mL), added with cesium carbonate (79 mg) and stirred at 60° C. After 2 hours and 4 hours from the initiation of the reaction, ethyl 2-(4-fluorophenyl)-2-oxoacetate (73 mg), and ethyl 2-(4-fluorophenyl)-2-oxoacetate (73 mg) and cesium carbonate (132 mg) were respectively added and stirring was continued for in total 18 hours. The reaction solution was allowed to cool to room temperature, added with water and extracted with ethyl acetate. The organic layer was sequentially washed with water and a saturated sodium chloride solution and dried over anhydrous magnesium sulphate. The residue obtained after distillation under reduced pressure was purified by silica gel chromatography (hexane:ethyl acetate=90:10→50:50) to give the titled compound (43 mg) having the following physical properties.

TLC: Rf 0.28 (hexane:ethyl acetate=1:1).

Example 43: Ethyl {4-[3-(4-fluorophenoxy)-5-{[(4-hydroxy-4-isobutyl-1-piperidinyl)carbonyl]amino}phenoxy]phenyl}(hydroxy)acetate The compound prepared in Example 42 (43 mg) was dissolved in methanol (1 mL) and stirred at 0° C. The reaction solution was added with sodium borohydride (3 mg), stirred for 15 minutes, added with water and extracted with ethyl acetate. The organic layer was sequentially washed with water and a saturated sodium chloride solution and dried over anhydrous magnesium sulphate. The residue obtained after distillation under reduced pressure was purified by silica gel chromatography (hexane:ethyl acetate=75:25→50:50) to give the titled compound (24 mg) having the following physical properties.

TLC: Rf 0.12 (hexane:ethyl acetate=1:1).

Example 44: {4-[3-(4-fluorophenoxy)-5-{[(4-hydroxy-4-isobutyl-1-piperidinyl)carbonyl]amino}phenoxy]phenyl}(hydroxy)acetic Acid The compound prepared in Example 43 (24 mg) was dissolved in methanol (0.4 mL), added with a 2 N sodium hydroxide aqueous solution (52 μL) and stirred at 35° C. for 13 hours. The solution was added with 1 N hydrochloric acid for neutralization at 0° C. and added with water and ethyl acetate for extraction. The organic layer was sequentially washed with water and a saturated sodium chloride solution and dried over anhydrous magnesium sulphate. Distillation under reduced pressure gave the titled compound (21.6 mg) having the following physical properties.

TLC: Rf 0.16 (dichloromethane:methanol:acetic acid=100:10:1);

$^1$H-NMR (CDCl$_3$): δ 7.38 (d, 2H), 7.03-6.90 (m, 6H), 6.78 (s, 1H), 6.64 (s, 1H), 6.27 (t, 1H), 5.08 (s, 1H), 3.67 (d, 2H), 3.30-3.18 (m, 2H), 1.77 (td, 1H), 1.63-1.46 (m, 4H), 1.34 (d, 2H), 0.92 (d, 6H).

Example 45: N-[3-(4-fluorophenoxy)-5-(4-{2-methyl-1-[(methylsulphonyl)amino]-1-oxo-2-propanyl}phenoxy)phenyl]-4-hydroxy-4-isobutyl-1-piperidinecarboxamide The compound prepared in Example 9 (320 mg), methanesulphonamide (80 mg), EDC (160 mg) and 4-dimethylaminopyridine (104 mg) were suspended in dichloromethane (12 mL) and the suspension was heated to 70° C. for 2 hours with a microwave. The reaction solution was subjected to distillation under reduced pressure, then dissolved in ethyl acetate and washed twice with 1 N hydrochloric acid and once with a saturated sodium chloride solution. The organic layer was subjected to distillation of the solvent and the resulting residue was purified by silica gel chromatography (dichloromethane:methanol=16:1). The resulting residue was further washed with hexane and t-butyl methyl ether to give the titled compound (215 mg) having the following physical properties.

TLC: Rf 0.45 (dichloromethane:methanol=8:1);

$^1$H-NMR (CD$_3$OD): δ 7.32 (d, 2H), 7.16-6.97 (m, 6H), 6.85 (t, 1H), 6.79 (t, 1H), 6.21 (t, 1H), 3.88-3.72 (m, 2H), 3.27-3.15 (m, 5H), 1.98-1.76 (m, 1H), 1.54 (s, 6H), 1.66-1.47 (m, 4H), 1.39 (d, 2H), 0.97 (d, 6H).

[Method for Preparing Crystals of the Present Compound]

The compounds of Examples in the present invention can be crystallized according to the methods described in Examples or similar methods thereto.

The crystals were subjected to measurement under the following conditions and the physical properties described in Examples were obtained.

[1] X-Ray Powder Diffraction Spectrum
<Measurement Conditions>
Instrument: BRUKER D8 DISCOVER with GADDS from BRUKER axs;
Target: Cu;
Filter: none;
Voltage: 40 kV;
Current: 40 mA;
Exposure time: 3 min.
[2] Differential Scanning Calorimetry (DSC)
<Measurement Conditions>
Instrument: DSC 822e from METTLER TOLEDO;
Sample amount: 1 to 2 mg;
Sample cell: 40-µL aluminium pan;
Nitrogen gas flow: 40 mL/min;
Heating rate: 10° C./min (25 to 220° C., 25 to 240° C., 25 to 250° C.)

Example A: Crystal of 2-{4-[3-(4-fluorophenoxy)-5-{[(4-hydroxy-4-isobutyl-1-piperidinyl)carbonyl]amino}phenoxy]phenyl}-2-methylpropanoic Acid (Type A Crystal)

In Example 9, the obtained purified product was added with ethyl acetate (7 v/w) and stirred at 0 to 30° C. The solution was filtered once, added with toluene (3 v/w), added with a seed crystal and stirred at 25° C. for 3 hours. The mixture was added with toluene (10 v/w), cooled to 0° C. and stirred for 1.5 hours. The resulting crystal was filtered and washed with toluene (2 v/w) to give the titled crystal. The X-ray powder diffraction spectrum and the differential scanning calorimetry (DSC) chart of the resulting crystal are shown in FIGS. 1 and 2, respectively. The diffraction angle 2θ and relative intensity in the X-ray powder diffraction spectrum are shown in the following table.

X-Ray Powder Diffraction Spectrum:

TABLE 1

| Diffraction angle 2θ (degree) | Relative intensity (%) |
| --- | --- |
| 6.6 | 100 |
| 7.9 | 14.8 |
| 9.5 | 91.9 |
| 10.1 | 25.4 |
| 13.0 | 46 |
| 13.4 | 42.9 |
| 14.0 | 24.2 |
| 15.3 | 18.5 |
| 16.6 | 39.5 |
| 17.3 | 44.6 |
| 18.3 | 49.5 |
| 19.0 | 47.8 |
| 19.6 | 50.1 |
| 20.0 | 31.3 |
| 21.1 | 18 |
| 22.8 | 23.6 |
| 23.5 | 23 |
| 23.8 | 23.8 |
| 24.4 | 14 |

The present crystal showed the onset of the endothermic peak at about 143° C.

Example B: Crystal of 2-{4-[3-({[4-(2-ethylbutyl)-4-hydroxy-1-piperidinyl]carbonyl}amino)-5-(4-fluorophenoxy)phenoxy]phenyl}-2-methylpropanoic Acid (Type A Crystal)

The compound prepared in Example 9(20) was added with ethanol (35 v/w) and water (10 v/w). The mixture was heated in an oil bath at 70° C. for dissolution. The solution was allowed to cool from 70° C. to 25° C. and the resulting crystal was then collected by filtration and dried under reduced pressure to give the titled crystal. The resulting crystal was analyzed and the X-ray powder diffraction spectrum and the differential scanning calorimetry chart thereof are shown in FIGS. 3 and 4, respectively. The diffraction angle 2θ and relative intensity in the X-ray powder diffraction spectrum are shown in the following table.

X-Ray Powder Diffraction Spectrum:

TABLE 2

| Diffraction angle 2θ (degree) | Relative intensity (%) |
| --- | --- |
| 5.8 | 17.4 |
| 7.3 | 100 |
| 8.8 | 10.5 |
| 9.7 | 9.7 |
| 10.5 | 10.5 |
| 11.4 | 16.6 |
| 11.6 | 17.3 |
| 12.4 | 11.3 |
| 13.7 | 14.6 |
| 14.3 | 14.1 |
| 15.1 | 32.9 |

TABLE 2-continued

| Diffraction angle 2θ (degree) | Relative intensity (%) |
| --- | --- |
| 15.7 | 15 |
| 16.7 | 63.1 |
| 17.3 | 27 |
| 18.3 | 31 |
| 19.5 | 40.5 |
| 20.3 | 23 |
| 21.0 | 35 |
| 21.4 | 38.6 |
| 22.7 | 23.6 |
| 23.5 | 11.5 |
| 24.7 | 40.1 |

The present crystal showed the onset of the endothermic peak at about 170° C.

Example C: Crystal of 1-{4-[3-(4-fluorophenoxy)-5-({[4-hydroxy-4-(3-pentanyl)-1-piperidinyl]carbonyl}amino)phenoxy]phenyl}cyclopropanecarboxylic Acid (Type A Crystal)

The compound prepared in Example 13 was added with 15 μL of ethanol (15 v/w). The mixture was heated in an oil bath at 70° C. for dissolution. The solution was allowed to cool from 70° C. to 25° C. and the resulting crystal was then collected by filtration and dried under reduced pressure to give the titled crystal. The resulting crystal was analyzed and the X-ray powder diffraction spectrum and the differential scanning calorimetry (DSC) chart thereof are shown in FIGS. 5 and 6, respectively. The diffraction angle 2θ and relative intensity in the X-ray powder diffraction spectrum are shown in the following table.

X-Ray Powder Diffraction Spectrum:

TABLE 3

| Diffraction angle 2θ (degree) | Relative intensity (%) |
| --- | --- |
| 7.7 | 82.5 |
| 11.9 | 35.2 |
| 14.0 | 22.7 |
| 15.6 | 40.8 |
| 16.3 | 42.2 |
| 16.7 | 100 |
| 17.8 | 94.9 |
| 18.3 | 39.6 |
| 18.9 | 54.3 |
| 19.4 | 27.9 |
| 19.9 | 36.7 |
| 20.2 | 74.2 |
| 21.3 | 73.3 |
| 21.7 | 41.6 |
| 22.4 | 37.4 |
| 22.9 | 47.9 |
| 23.3 | 40.3 |
| 24.1 | 26 |

The present crystal showed the onset of the endothermic peak at about 182° C.

EXPERIMENTAL EXAMPLES

The effects of the present compounds were verified based on the experimental methods shown hereinbelow as the biological experimental example and physical experimental example.

Biological Experimental Example 1: Evaluation of S1P$_2$ Antagonistic Activity by Monitoring the Change in Intracellular Calcium Ion Concentration Chinese hamster ovary (CHO) cells overexpressing the human S1P$_2$ gene were cultured in a Ham's F12 medium containing 10% fetal bovine serum (FBS), an antibiotic/antifungal agent and G418. CHO cells overexpressing the rat S1P$_2$ gene were cultured in a Ham's F12 medium containing 10% FBS, penicillin/streptomycin and blasticidin S. The cultured cells were incubated in a Fura2-AM solution (5 μM) [a Ham's F12 medium containing FBS (10%), HEPES buffer (20 mM, pH 7.2 to 7.5) and probenecid (2.5 mM)] at 37° C. for 60 minutes. The cells were washed twice with a Hanks' balanced saline containing HEPES buffer (20 mM, pH 7.2 to 7.5) and probenecid (2.5 mM) and immersed in the same solution. A plate was mounted on a fluorescence-based drug screening system and the intracellular calcium ion concentration was measured for 30 seconds without stimulation. A test substance (the final concentration of human S1P$_2$: 0.25 nM to 25 μM and the final concentration of rat S1P$_2$: 0.25 nM to 2.5 μM) or a dimethyl sulphoxide (DMSO) solution was added and after 3 minutes SIP (final concentration: 300 nM) was added and the increase in the intracellular calcium ion concentration before and after the addition of SIP was measured with an interval of 3 seconds (excitation wavelength: 340 nm and 380 nm, fluorescence wavelength: 540 nm).

The S1P$_2$ antagonistic activity was calculated using the suppression obtained from the following formula, wherein A is a control value which was a peak value after addition of SIP (final concentration: 300 nM) in the wells added with DMSO without a test substance and B is an increased amount after addition of SIP in the cells treated with the test substance:

$$\text{Suppression (\%)} = [(A-B)/A] \times 100 \qquad [\text{E 1}]$$

IC$_{50}$ value was calculated as the concentration of the present compound which showed the 50% suppression.

Comparative compounds used were the compounds disclosed in Example 1(64) (hereinafter referred to as comparative compound A) and Example 1(85) (hereinafter referred to as comparative compound B) in Patent Document 3 (WO 2004/002531). The structural formulae of the comparative compounds are shown below respectively.

[C 25]

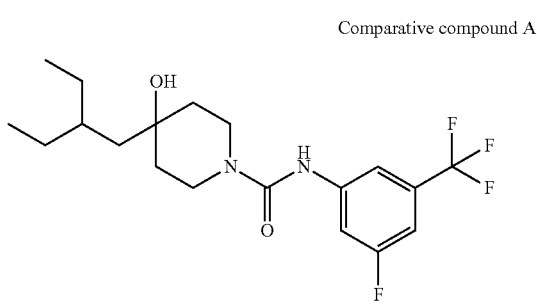

Comparative compound A

[C 26]

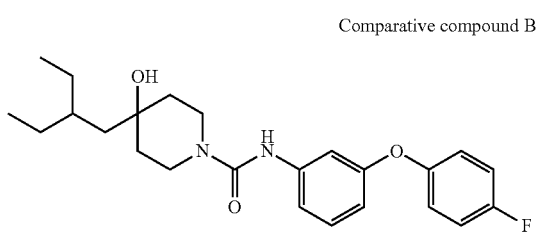

Comparative compound B

The human and rat $S1P_2$ antagonistic activities of the present compounds and comparative compounds are shown in the following Table 4.

TABLE 4

| Compound | $S1P_2$ antagonistic activity $IC_{50}$ (nM) | |
|---|---|---|
| | Human | Rat |
| Comparative compound A | 1600 | 72 |
| Comparative compound B | 1200 | 27 |
| Example 15 (1) | 7.0 | 9.6 |
| Example 9 (3) | 6.2 | 3.3 |
| Example 15 (6) | 5.1 | 5.0 |
| Example 9 | 2.3 | 2.5 |
| Example 13 | 3.0 | 3.0 |
| Example 19 | 9.4 | 1.7 |
| Example 38 | 3.4 | 1.0 |

As a result, it was found that the present compounds have significantly improved human $S1P_2$ antagonistic activity compared to the comparative compounds. In addition, the present compounds also have improved difference in the $S1P_2$ antagonistic activity between species, i.e. between human and rat and thus may allow extrapolation of the efficacy obtained in rat pathological models to human.

Physical Experimental Example 2: Solubility Measurement

A solution for obtaining a calibration curve was prepared by diluting a test substance (10 mmol/L, DMSO solution) in acetonitrile and adding acetonitrile containing an internal standard substance (warfarin) to adjust to 0.1, 0.4 and 2 μmol/L. A sample solution was prepared by adding to 495 μL (pH 6.8) of the second solution defined in Japanese Pharmacopoeia (a solution used was obtained by adding water to 250 mL of a 0.2 mol/L potassium dihydrogen phosphate reagent solution and 118 mL of a 0.2 mol/L sodium hydroxide reagent solution to adjust to 1000 mL) 5 μL of a test substance (10 mmol/L, DMSO solution), stirring at room temperature for 5 hours, transferring the obtained solution to a plate with a filter for vacuum filtration, diluting 20 μL of the filtrate with acetonitrile and adding acetonitrile containing the internal standard. The solution for obtaining a calibration curve and the sample solution (5 μL each) were injected to LC-MS/MS (Discovery Max from Thermo Scientific) for quantification (quantification range: 0.1 to 2 μmol/L). The solubility was calculated by multiplying the quantified value by 50. When the calculated value was outside of the quantification range, the solubility was expressed as <5 μmol/L or 100 μmol/L.

The solubility of the present compounds and the comparative compounds is shown in the following Table 5.

TABLE 5

| Compound | Solubility (μmol/L) |
|---|---|
| Comparative compound A | <5 |
| Comparative compound B | <5 |
| Example 9 (1) | 80.3 |
| Example 9 (3) | 90.1 |
| Example 9 | 77.2 |
| Example 19 | 78.3 |
| Example 38 | 70.0 |

As a result, it was found that the present compounds have superior solubility than the comparative compounds.

FORMULATION EXAMPLES

Formulation Example 1

The following components were mixed and then compressed to make tablets according to the conventional method to obtain 10,000 tablets respectively containing 10 mg of the active ingredient.

| | |
|---|---|
| 4-(2-ethylbutyl)-N-[3-(4-fluorophenoxy)-5-{4-[(4-hydroxy-1-piperidinyl)carbonyl]phenoxy}phenyl]-4-hydroxy-1-piperidine carboxamide | 100 g |
| Carboxymethylcellulose calcium (disintegrating agent) | 20 g |
| Magnesium stearate (lubricant) | 10 g |
| Microcrystalline cellulose | 870 g |

Formulation Example 2

The following components were mixed according to the conventional method, then filtered through a dust removal filter, divided at 5 ml per ampoule, sterilized by heating in an autoclave to obtain 10,000 ampoules respectively containing 20 mg of the active ingredient.

| | |
|---|---|
| 1-{4-[3-(4-fluorophenoxy)-5-({[4-hydroxy-4-(3-pentanyl)-1-piperidinyl]carbonyl}amino)phenoxy]phenyl}cyclopropanecarboxylic acid | 200 g |
| Mannitol | 20 g |
| Distilled water | 50 L |

INDUSTRIAL APPLICABILITY

The present compound has high human $S1P_2$ antagonistic activity and thus is useful for therapy of $S1P_2$-mediated diseases such as diseases resulting from vascular constriction and fibrosis.

The invention claimed is:

1. A method of preparing a compound of formula (I-A):

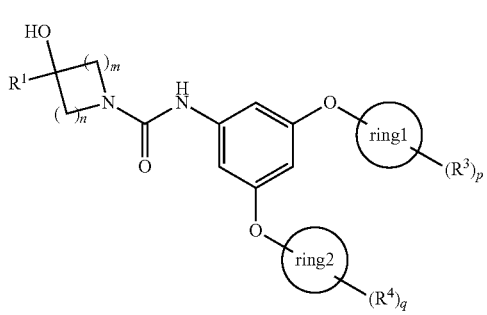

wherein
R$^1$ is (1) a C1-8 alkyl group which may be substituted with 1 to 5 R$^{21}$ groups, (2) a C2-8 alkenyl group which may be substituted with 1 to 5 R$^{21}$ groups, (3) a C2-8 alkynyl group which may be substituted with 1 to 5 R$^{21}$ groups, (4) a C3-7 carbocycle which may be substituted with 1 to 5 substituents selected from the group consisting of a C1-4 alkyl group, a C1-4 haloalkyl group, a C1-4 alkoxy group and a halogen atom, or (5) —CONR$^{31}$R$^{32}$;

R$^{21}$ is (1) a halogen atom, (2) —OR$^{22}$ (wherein, R$^{22}$ is (1) a hydrogen atom, (2) a C1-4 alkyl group or (3) a C1-4 haloalkyl group), (3) —NR$^{23}$R$^{24}$ (wherein, R$^{23}$ and R$^{24}$ each independently are (1) a hydrogen atom or (2) a C1-4 alkyl group) or (4) an oxo group;

R$^{31}$ and R$^{32}$ each independently are (1) a hydrogen atom or (2) a C1-4 alkyl group;

R$^3$ and R$^4$ each independently are (1) a halogen atom, (2) a C1-4 alkyl group, (3) a C1-4 haloalkyl group, (4) a C1-4 alkoxy group, (5) a hydroxy group, (6) -L-CONR$^6$R$^7$, (7) -L-SO$_2$R$^8$ or (8) -L-COOR$^9$;

L is (1) a bond, (2) a group represented by the formula:

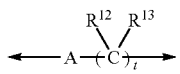

wherein A is (1) a bond or (2) an oxygen atom; R$^{12}$ and R$^{13}$ each independently are (1) a hydrogen atom, (2) a C1-4 alkyl group, (3) a hydroxy group or (4) NH$_2$ or (5) R$^{12}$ and R$^{13}$ together with the carbon atom to which they are attached may form a C3-7 carbocycle; and the arrow on the right hand side binds to —CONR$^6$R$^7$, —SO$_2$R$^8$ or —COOR$^9$, (3) a C2-4 alkenylene group, (4) a —O-C2-4 alkenylene group, (5) an oxygen atom or (6) a nitrogen atom which may be substituted with a C1-4 alkyl group;

R$^6$ and R$^7$ each independently are (1) a hydrogen atom, (2) a C1-4 alkyl group, (3) a C1-4 haloalkyl group, (4) a hydroxy group, (5) —CONR$^{15}$R$^{16}$, (6) —SO$_2$NR$^{15}$R$^{16}$, (7) —COR$^{17}$ or (8) —SO$_2$R$^{17}$, or R$^6$ and R$^7$ together with the nitrogen atom to which they are attached may form a 4- to 7-membered nitrogen-containing saturated heterocycle that may be substituted with a hydroxy group;

R$^8$ is (1) a C1-4 alkyl group, (2) a C1-4 haloalkyl group or (3) NR$^{10}$R$^{11}$;

R$^9$ is (1) a hydrogen atom or (2) a C1-8 alkyl group;

R$^{10}$ and R$^{11}$ each independently are (1) a hydrogen atom, (2) a C1-4 alkyl group, (3) —CONR$^{15}$R$^{16}$, (4) —SO$_2$NR$^{15}$R$^{16}$, (5) —COR$^{17}$ or (6) —SO$_2$R$^{17}$;

the ring 1 and the ring 2 each independently are benzene or pyridine ring;

R$^{15}$ and R$^{16}$ each independently are (1) a hydrogen atom, (2) a C1-4 alkyl group or (3) a 5- to 7-membered cyclic group;

R$^{17}$ is (1) a C1-4 alkyl group or (2) a 5- to 7-membered cyclic group;

n is an integer of 1 to 2;
m is an integer of 1 to 2;
p is an integer of 0 to 5;
q is an integer of 0 to 5;
r is an integer of 0;
t is an integer of 1 to 4;

when p is 2 or more, a plurality of R$^3$ groups may be the same or different;

when q is 2 or more, a plurality of R$^4$ groups may be the same or different; and when t is 2 or more, a plurality of R$^{12}$ and R$^{13}$ groups may be respectively the same or different, or a salt thereof, wherein the method comprises:
reacting a compound of formula (E):

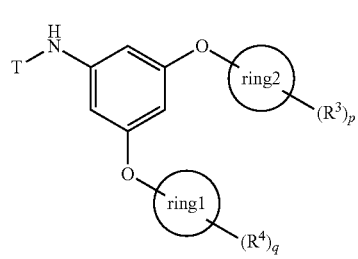

wherein T is a 2,2,2-trichloroethoxycarbonyl (Troc) group, a phenoxycarbonyl group, or a p-nitrophenoxycarbonyl group; and the other symbols have the same definitions as above, in the presence of a base with a compound of formula (V)

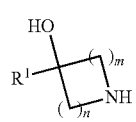

wherein all symbols have the same definitions as above, in an organic solvent.

2. The method according to claim 1, wherein the compound of formula (I-A) is 2-{4-[3-(4-fluorophenoxy)-5-{[(4-hydroxy-4-isobutyl-1-piperidinyl)carbonyl]amino}phenoxy]phenyl}-2-methylpropanoic acid or a salt thereof.

3. The method according to claim 1, wherein the ring 1 and the ring 2 each independently are a benzene.

4. The method according to claim 1, wherein the base is selected from the group consisting of pyridine, triethylamine, dimethylaniline, dimethylaminopyridine, diisopropylethylamine, or a mixture thereof.

5. The method according to claim 1, wherein the organic solvent is selected from N,N-dimethylacetamide, chloroform, dichloromethane, diethyl ether, tetrahydrofuran, and a mixture thereof.

6. The method according to claim 2, wherein the base is selected from the group consisting of pyridine, triethylamine, dimethylaniline, dimethylaminopyridine, diisopropylethylamine, or a mixture thereof.

7. The method according to claim 2, wherein the organic solvent is selected from N,N-dimethylacetamide, chloroform, dichloromethane, diethyl ether, tetrahydrofuran, and a mixture thereof.

8. The method according to claim 3, wherein the base is selected from the group consisting of pyridine, triethylamine, dimethylaniline, dimethylaminopyridine, diisopropylethylamine, or a mixture thereof.

9. The method according to claim 3, wherein the organic solvent is selected from N,N-dimethylacetamide, chloroform, dichloromethane, diethyl ether, tetrahydrofuran, and a mixture thereof.

* * * * *

UNITED STATES PATENT AND TRADEMARK OFFICE
CERTIFICATE OF CORRECTION

PATENT NO.        : 10,835,520 B2
APPLICATION NO.   : 16/148647
DATED             : November 17, 2020
INVENTOR(S)       : Naganawa et al.

Page 1 of 1

It is certified that error appears in the above-identified patent and that said Letters Patent is hereby corrected as shown below:

On the Title Page

Related U.S. Application Data, delete "(60)" and insert --(62)-- therefor.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*